United States Patent
Hu et al.

(10) Patent No.: US 8,128,607 B2
(45) Date of Patent: Mar. 6, 2012

(54) DEVICES AND METHODS FOR TREATMENT OF DAMAGED TISSUE

(75) Inventors: Dean Hu, San Leandro, CA (US);
Moshe Pinto, Mountain View, CA (US);
Kenton Fong, Mountain View, CA (US)

(73) Assignee: Spiracur Inc., Sunnyvale, CA (US)

( * ) Notice: Subject to any disclaimer, the term of this patent is extended or adjusted under 35 U.S.C. 154(b) by 183 days.

(21) Appl. No.: 12/760,406

(22) Filed: Apr. 14, 2010

(65) Prior Publication Data

US 2010/0198173 A1 Aug. 5, 2010

Related U.S. Application Data

(63) Continuation of application No. 12/372,661, filed on Feb. 17, 2009.

(60) Provisional application No. 61/028,835, filed on Feb. 14, 2008.

(51) Int. Cl.
*A61M 35/00* (2006.01)
(52) U.S. Cl. .................................. 604/313; 604/319
(58) Field of Classification Search .................. 604/133, 604/134, 218, 313, 317, 319, 403; 141/26, 141/67
See application file for complete search history.

(56) References Cited

U.S. PATENT DOCUMENTS

| | | |
|---|---|---|
| 2,198,666 A | 4/1940 | Gruskin |
| 2,472,116 A | 6/1949 | Maynes |
| 2,660,342 A | 11/1953 | Ruf |
| 2,863,452 A | 12/1958 | Ogle, Sr. |
| 3,334,628 A | 8/1967 | Saemann et al. |
| 3,583,399 A | 6/1971 | Ritsky |
| 3,628,325 A | 12/1971 | Morita |
| 3,680,560 A | 8/1972 | Pannier, Jr. et al. |
| 3,779,243 A | 12/1973 | Tussey et al. |
| 3,809,086 A | 5/1974 | Schachet et al. |
| 3,809,087 A | 5/1974 | Lewis, Jr. |
| 3,833,030 A | 9/1974 | Waldbauer, Jr. et al. |
| 3,841,331 A | 10/1974 | Wilder et al. |
| 3,982,546 A | 9/1976 | Friend |
| 4,041,934 A | 8/1977 | Genese |
| 4,080,970 A | 3/1978 | Miller |
| 4,278,089 A * | 7/1981 | Huck et al. .................. 604/134 |
| 4,287,819 A | 9/1981 | Emerit |

(Continued)

FOREIGN PATENT DOCUMENTS

CN 2851641 Y 12/2006

(Continued)

OTHER PUBLICATIONS

Anonymous. (Feb. 10, 2000). "Drain and Suture Line Care for Wounds," *The Cleveland Clinic Foundation*, located at <http://www.clevelandclinic.org/health/health-info/docs/2200/2205.asp?i . . .>, last visited Oct. 15, 2007, four pages.

(Continued)

*Primary Examiner* — Melanie Hand
(74) *Attorney, Agent, or Firm* — Morrison & Foerster LLP

(57) ABSTRACT

Methods and devices for treatment of damaged tissue are disclosed, including treatment of wounds by employing non-electrically powered, reduced pressure therapy devices. Maintenance and control of the sub atmospheric pressure exerted may be provided by such devices while minimizing discomfort to the user. The devices may be configured to be worn inconspicuously underneath clothing.

35 Claims, 38 Drawing Sheets

U.S. PATENT DOCUMENTS

| | | | |
|---|---|---|---|
| 4,333,456 A | 6/1982 | Webb | |
| 4,333,458 A | 6/1982 | Margulies et al. | |
| 4,382,441 A | 5/1983 | Svedman | |
| 4,404,924 A | 9/1983 | Goldberg et al. | |
| 4,525,167 A | 6/1985 | Goldberg et al. | |
| 4,549,554 A | 10/1985 | Markham | |
| 4,578,060 A | 3/1986 | Huck et al. | |
| 4,648,870 A | 3/1987 | Goldberg et al. | |
| 4,664,128 A | 5/1987 | Lee | |
| 4,743,232 A | 5/1988 | Kruger | |
| 4,758,232 A | 7/1988 | Chak | |
| 4,867,748 A | 9/1989 | Samuelsen | |
| 4,882,337 A | 11/1989 | Sweet et al. | |
| 4,889,250 A * | 12/1989 | Beyer | 215/228 |
| 4,969,880 A | 11/1990 | Zamierowski | |
| 5,071,409 A | 12/1991 | Rosenberg | |
| 5,100,396 A | 3/1992 | Zamierowski | |
| 5,116,310 A | 5/1992 | Seder et al. | |
| 5,157,808 A | 10/1992 | Sterner, Jr. | |
| 5,261,893 A | 11/1993 | Zamerowski | |
| 5,263,922 A | 11/1993 | Sova et al. | |
| 5,266,476 A | 11/1993 | Sussman et al. | |
| 5,395,345 A | 3/1995 | Gross | |
| 5,527,293 A | 6/1996 | Zamerowski | |
| 5,636,643 A | 6/1997 | Argenta et al. | |
| 5,645,081 A | 7/1997 | Argenta et al. | |
| 5,701,917 A | 12/1997 | Khouri | |
| 5,704,905 A | 1/1998 | Jensen et al. | |
| 5,711,969 A | 1/1998 | Patel et al. | |
| 6,071,267 A | 6/2000 | Zamerowski | |
| 6,142,982 A * | 11/2000 | Hunt et al. | 604/313 |
| 6,235,964 B1 | 5/2001 | Kadash et al. | |
| 6,261,276 B1 * | 7/2001 | Reitsma | 604/319 |
| 6,345,623 B1 | 2/2002 | Heaton et al. | |
| 6,458,109 B1 | 10/2002 | Henley et al. | |
| 6,461,467 B2 | 10/2002 | Blatchford et al. | |
| 6,553,998 B2 | 4/2003 | Heaton et al. | |
| 6,685,681 B2 | 2/2004 | Lockwood et al. | |
| 6,695,823 B1 | 2/2004 | Lina et al. | |
| 6,695,824 B2 | 2/2004 | Howard et al. | |
| 6,752,794 B2 | 6/2004 | Lockwood et al. | |
| 6,800,074 B2 | 10/2004 | Henley et al. | |
| 6,814,079 B2 | 11/2004 | Heaton et al. | |
| 6,825,246 B1 | 11/2004 | Fattman | |
| 6,855,135 B2 | 2/2005 | Lockwood et al. | |
| 6,979,324 B2 | 12/2005 | Bybordi et al. | |
| 6,986,234 B2 | 1/2006 | Liedtke | |
| 7,070,584 B2 | 7/2006 | Johnson et al. | |
| 7,117,869 B2 | 10/2006 | Heaton et al. | |
| 7,198,046 B1 | 4/2007 | Argenta et al. | |
| 7,216,651 B2 | 5/2007 | Argenta et al. | |
| 7,273,054 B2 | 9/2007 | Heaton et al. | |
| 7,316,672 B1 | 1/2008 | Hunt et al. | |
| 7,461,158 B2 | 12/2008 | Rider et al. | |
| 7,485,112 B2 | 2/2009 | Karpowicz et al. | |
| 7,520,872 B2 | 4/2009 | Biggie et al. | |
| 2001/0031943 A1 | 10/2001 | Urie | |
| 2001/0043943 A1 | 11/2001 | Coffey | |
| 2002/0150720 A1 | 10/2002 | Howard et al. | |
| 2002/0173808 A1 | 11/2002 | Houser et al. | |
| 2002/0183702 A1 | 12/2002 | Henley et al. | |
| 2003/0050594 A1 | 3/2003 | Zamierowski | |
| 2004/0249353 A1 | 12/2004 | Risks, Jr. et al. | |
| 2004/0261642 A1 | 12/2004 | Hess | |
| 2005/0101940 A1 | 5/2005 | Radl et al. | |
| 2005/0261642 A1 | 11/2005 | Weston | |
| 2006/0253090 A1 | 11/2006 | Bradley et al. | |
| 2006/0282028 A1 | 12/2006 | Howard et al. | |
| 2007/0027414 A1 | 2/2007 | Hoffman et al. | |
| 2007/0219512 A1 | 9/2007 | Heaton et al. | |
| 2007/0219532 A1 | 9/2007 | Karpowicz et al. | |
| 2008/0004559 A1 | 1/2008 | Riesinger | |
| 2008/0063615 A1 | 3/2008 | MacDonald et al. | |
| 2008/0082059 A1 | 4/2008 | Fink et al. | |
| 2008/0108977 A1 | 5/2008 | Heaton et al. | |
| 2008/0306448 A1 | 12/2008 | Lee | |
| 2008/0306456 A1 | 12/2008 | Riesinger | |
| 2009/0012482 A1 | 1/2009 | Pinto et al. | |
| 2009/0076467 A1 | 3/2009 | Pinto et al. | |
| 2010/0042021 A1 | 2/2010 | Hu et al. | |
| 2010/0137775 A1 | 6/2010 | Hu et al. | |

FOREIGN PATENT DOCUMENTS

| | | |
|---|---|---|
| DE | 20 2005 019 670 U1 | 6/2006 |
| GB | 2 195 255 A | 4/1988 |
| GB | 2 306 107 A | 4/1997 |
| GB | 2 431 351 A | 4/2007 |
| WO | WO-80/02182 A | 10/1980 |
| WO | WO2008/112304 A1 | 9/2008 |

OTHER PUBLICATIONS

Bagautdinov, N.A. (1986). "Variant of External Vacuum Aspiration in the Treatment of Purulent Diseases of Soft Tissues," in *Current Problems in Modern Clinical Surgery*, Volkov, V.Y. et al. eds., Cheboksary: Chuvashia State University, 14 pages. (includes English translation and translation certifications).

Chariker, M.E. et al. (Jun. 1989). "Effective Management of Incisional and Cutaneous Fistulae with Closed Suction Wound Drainage," *Contemporary Surgery* 34:59-63.

Davydov, Y.A. et al. (Sep. 1986). "Vacuum Therapy in the Treatment of Purulent Lactation Mastitis," *The Kremlin Papers: Perspectives in Wound Care* pp. 5-7. (English Translation of *Vestnik Khirurgii* article.).

Davydov, Y.A. et al. (Oct. 1988). "The Bacteriological and Cytological Assessment of Vacuum Therapy of Purulent Wounds," *The Kremlin Papers: Perspectives in Wound Care* pp. 11-14. (English Translation of *Vestnik Khirurgii* article.).

Davydov, Y.A. et al. (Feb. 1991). "Concepts for Clinical Biological Management of the Wound Process in the Treatment of Purulent Wounds Using Vacuum Therapy," *The Kremlin Papers: Perspectives in Wound Care* pp. 15-17. (English Translation of *Vestnik Khirurgii* article.).

Herrmann, L.G. et al. (1934). "The Conservative Treatment of Arteriosclerotic Peripheral Vascular Diseases: Passive Vascular Exercises (Pavaex Therapy)," *Ann. Surgery* pp. 750-760.

International Search Report mailed Jul. 28, 2008, for PCT Application No. PCT/US08/03412, filed Mar. 13, 2008, three pages. (4.40).

International Search Report mailed May 29, 2009, for PCT Application No. PCT/US2009/034158, filed Feb. 13, 2009, 2 pages. (1.40).

International Preliminary Report on Patentability mailed Sep. 24, 2009, for PCT Application No. PCT/US2008/003412, filed Mar. 13, 2008, 7 pages. (4.40).

International Search Report mailed on Jan. 21, 2010, for PCT Application No. PCT/US09/65959, filed on Nov. 25, 2009, 5 pages. (5.40).

International Search Report mailed on May 4, 2010, for PCT Application No. PCT/US2010/026269, filed on Mar. 4, 2010, 3 pages. (8.40).

Kostiuchenok, B.M. et al. (Sep. 1986). "The Vacuum Effect in the Surgical Treatment of Purulent Wounds," *The Kremlin Papers: Perspectives in Wound Care* pp. 3-4. (English Translation of *Vestnik Khirurgii* article.).

Meyer, D.C. et al. (Jun. 2005). "Weight-Loaded Syringes as a Simple and Cheap Alternative to Pumps for Vacuum-Enhanced Wound Healing," *Plastic and Reconstructive Surgery* 115(7):2174-2176, located at <http://gateway.tx.ovid.com.laneproxy.stanford.edu/gw2/ovidweb.cgi>, last visited on Oct. 15, 2007.

Svedman, P. (Sep. 3, 1983). "Irrigation Treatment of Leg Ulcers," *The Lancet* pp. 532-534.

Svedman, P. et al. (Aug. 1986). "A Dressing System Providing Fluid Supply and Suction Drainage Used for Continuous or Intermittent Irrigation," *Annals of Plastic Surgery* 17(2):125-133.

Ubbink, D.T. et al. (2009). "Topical Negative Pressure for Treating Chronic Wounds," *The Cochrane Collaboration* 3:1-32.

Urschel, J.D. et al. (1988). "The Effect of Mechanical Stress on Soft and Hard Tissue Repair; a Review," *British Journal of Plastic Surgery* 41:182-186.

Usupov, Y.N. et al. (Apr. 1987). "Active Wound Drainage," *The Kremlin Papers: Perspectives in Wound Care* pp. 8-10. (English Translation of *Vestnik Khirurgii* article.).

Written Opinion of the International Searching Authority mailed on Jan. 21, 2010, for PCT Application No. PCT/US09/65959, filed on Nov. 25, 2009, 7 pages.

Written Opinion mailed on May 4, 2010, for PCT Application No. PCT/US2010/026269, filed on Mar. 4, 2010, 7 pages.

Final Office Action mailed on Apr. 21, 2010, for U.S. Appl. No. 12/047,739, filed on Mar. 13, 2008, 16 pages.

Final Office Action mailed on Apr. 22, 2010, for U.S. Appl. No. 12/234,530, filed on Sep. 19, 2008, 14 pages.

Non-Final Office Action mailed on Oct. 29, 2009, for U.S. Appl. No. 12/234,530, filed on Sep. 19, 2008, 14 pages.

Non-Final Office Action mailed on Nov. 27, 2009, for U.S. Appl. No. 12/047,739, filed on Mar. 13, 2008, 18 pages.

International Preliminary Report on Patentability mailed Jun. 9, 2011, for PCT Application No. PCT/US2009/065959, filed Nov. 25, 2009, 9 pages.

Notice of Allowance mailed on Jun. 24, 2011, for U.S. Appl. No. 12/234,530, filed on Sep. 19, 2008, 11 pages.

US 7,186,244, 03/2007, Hunt et al. (withdrawn)

* cited by examiner

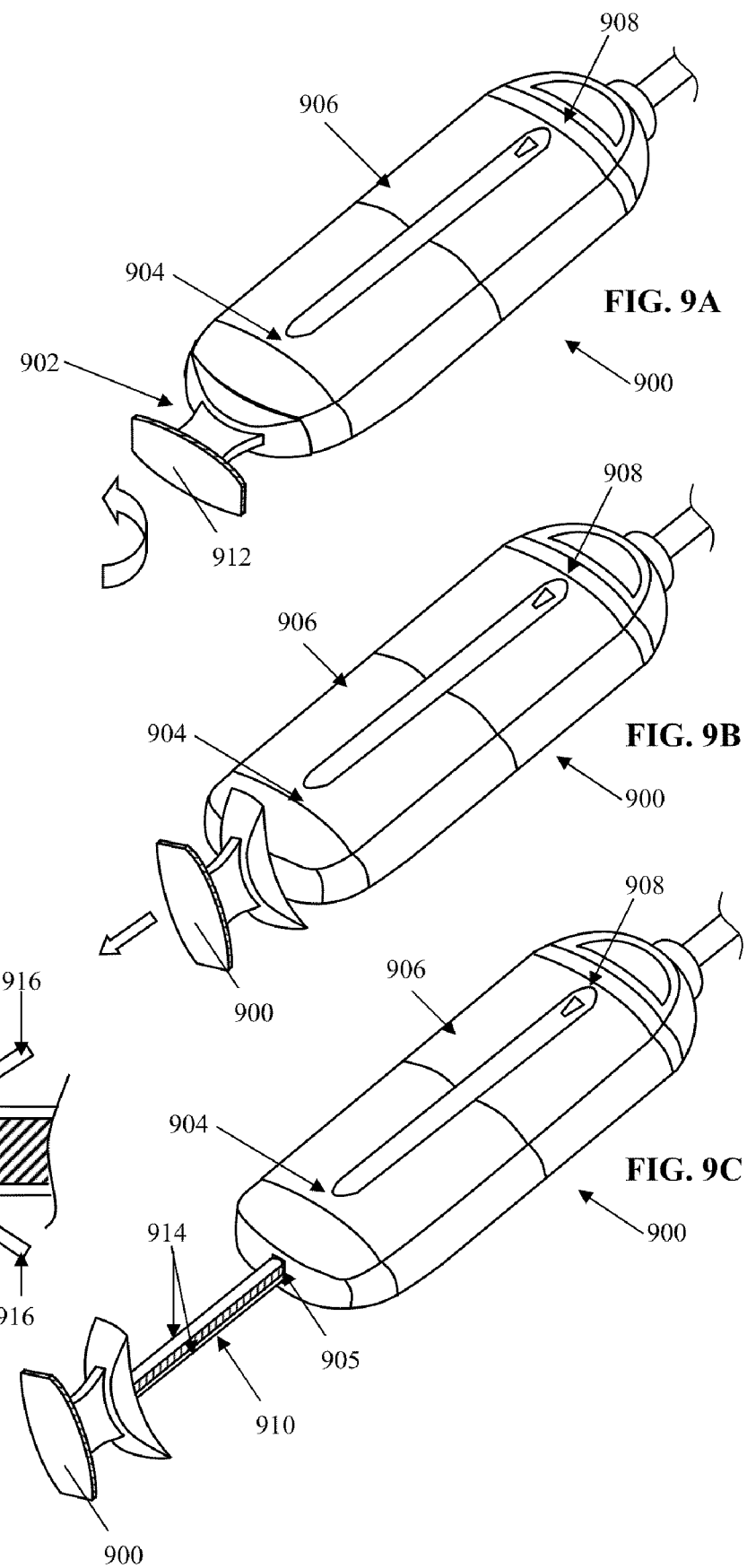

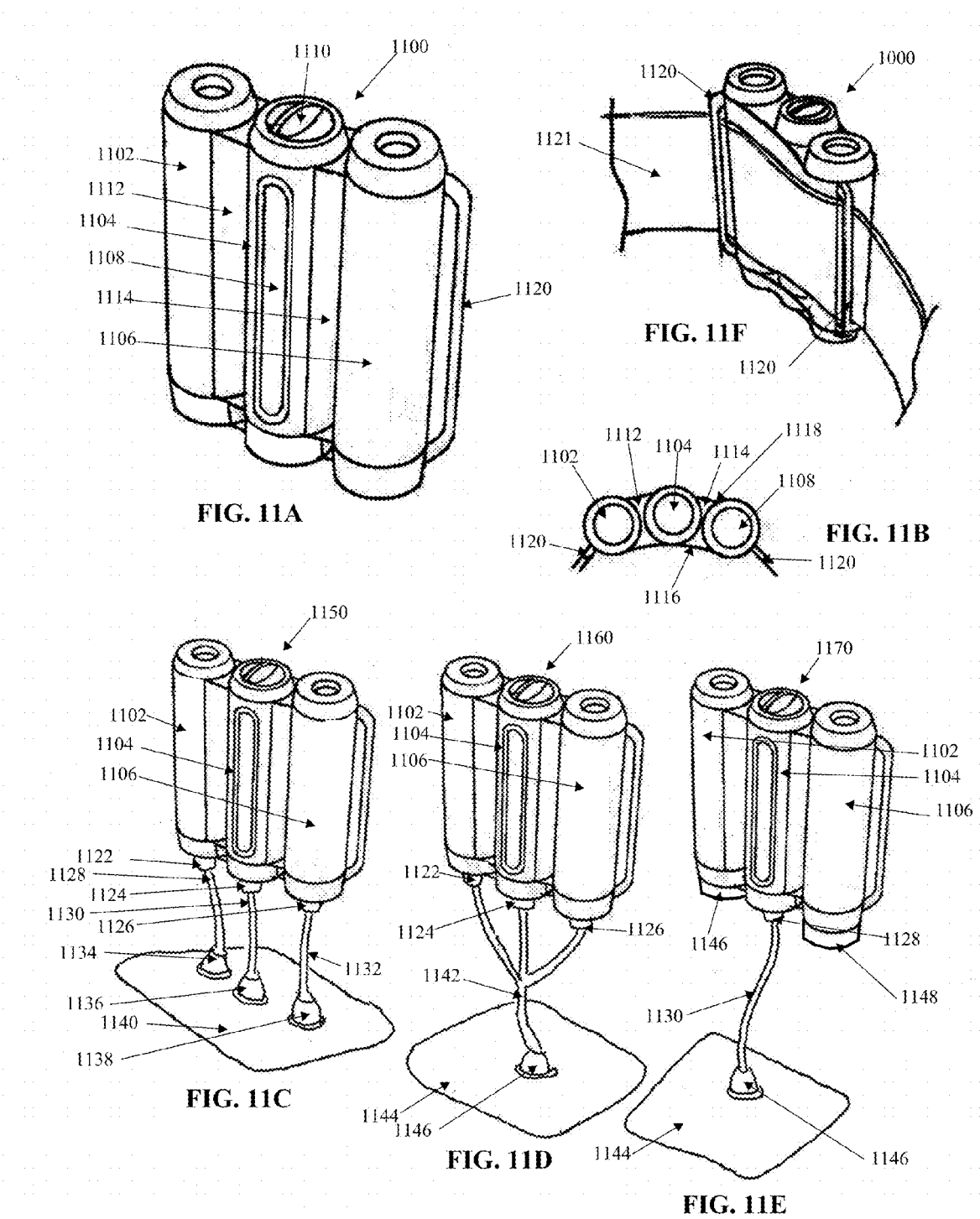

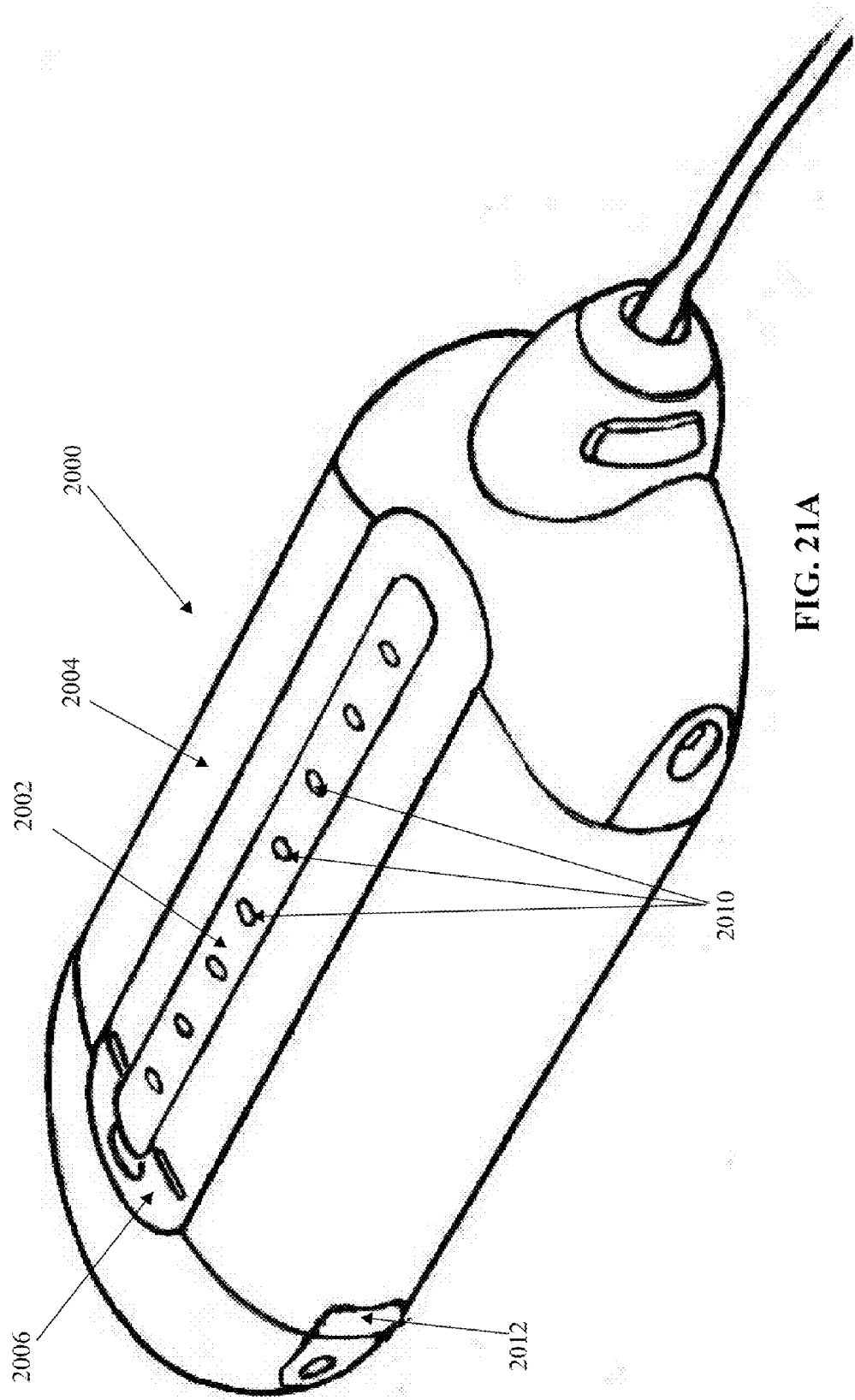

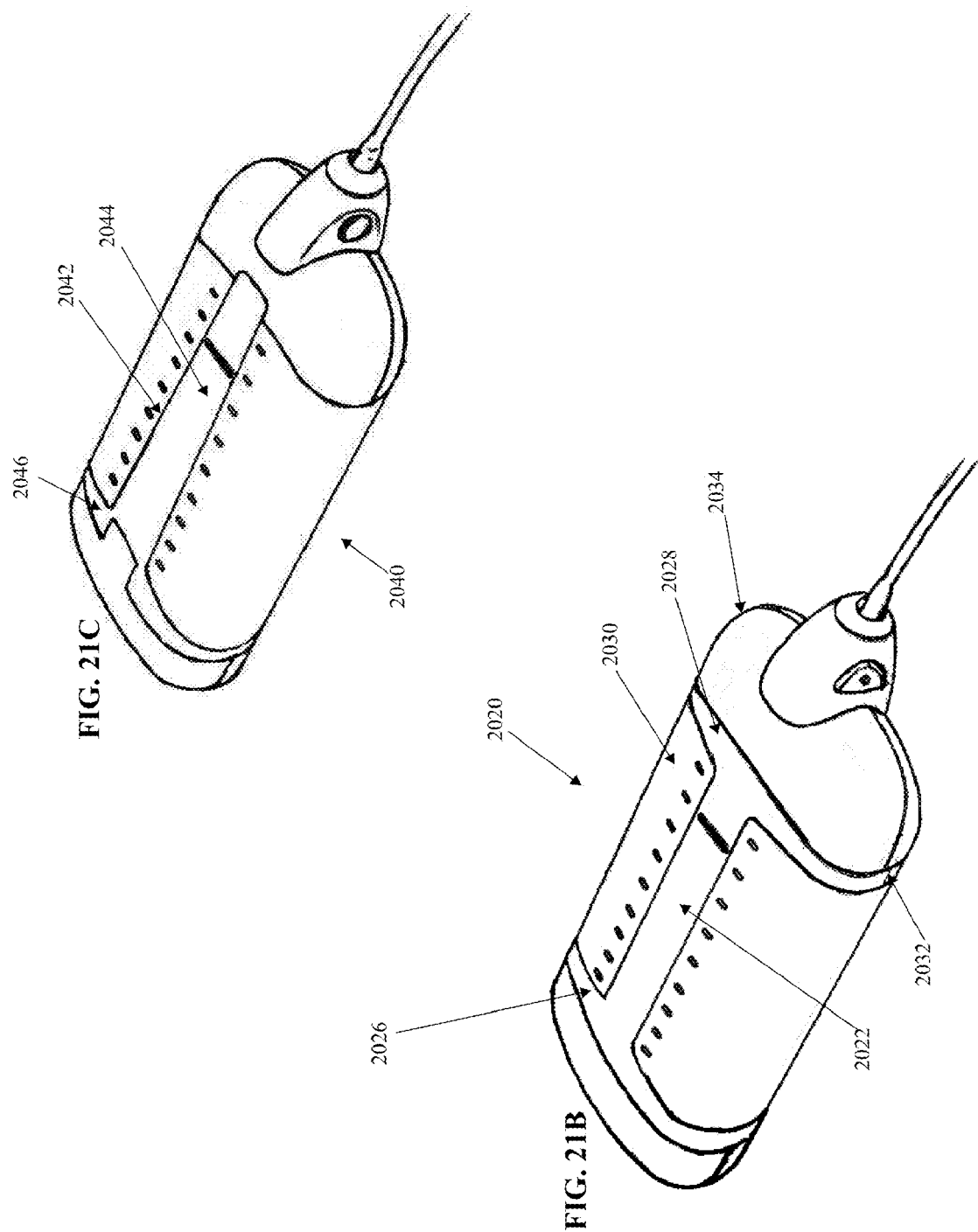

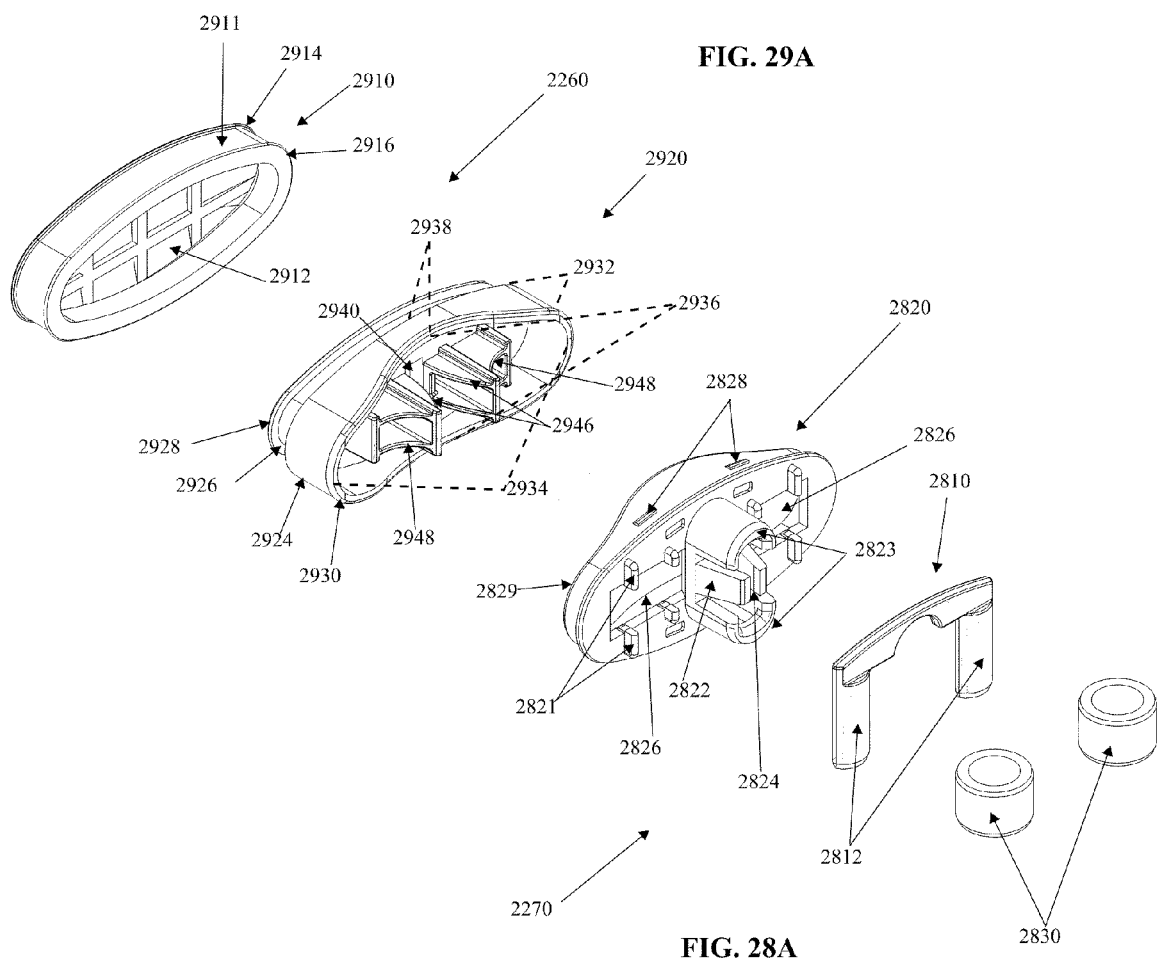

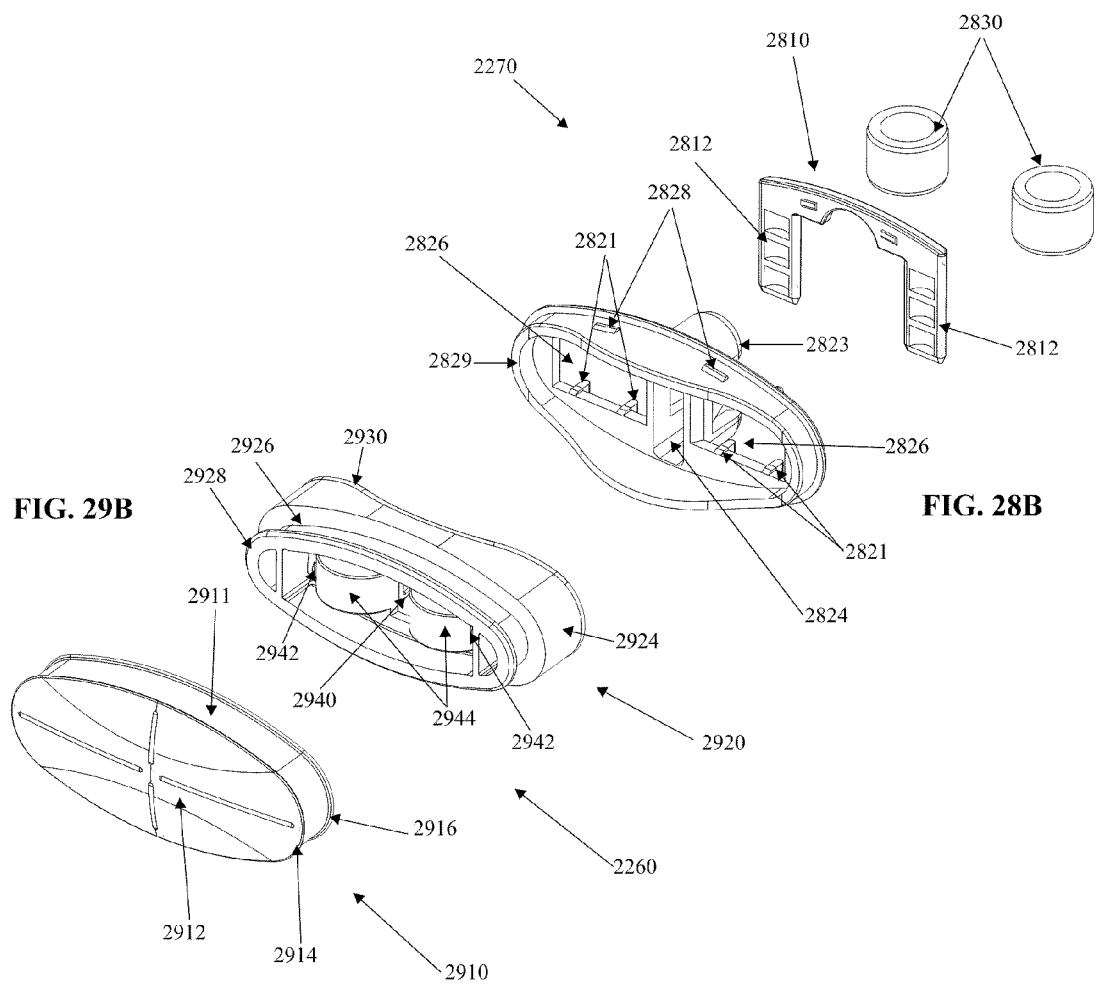

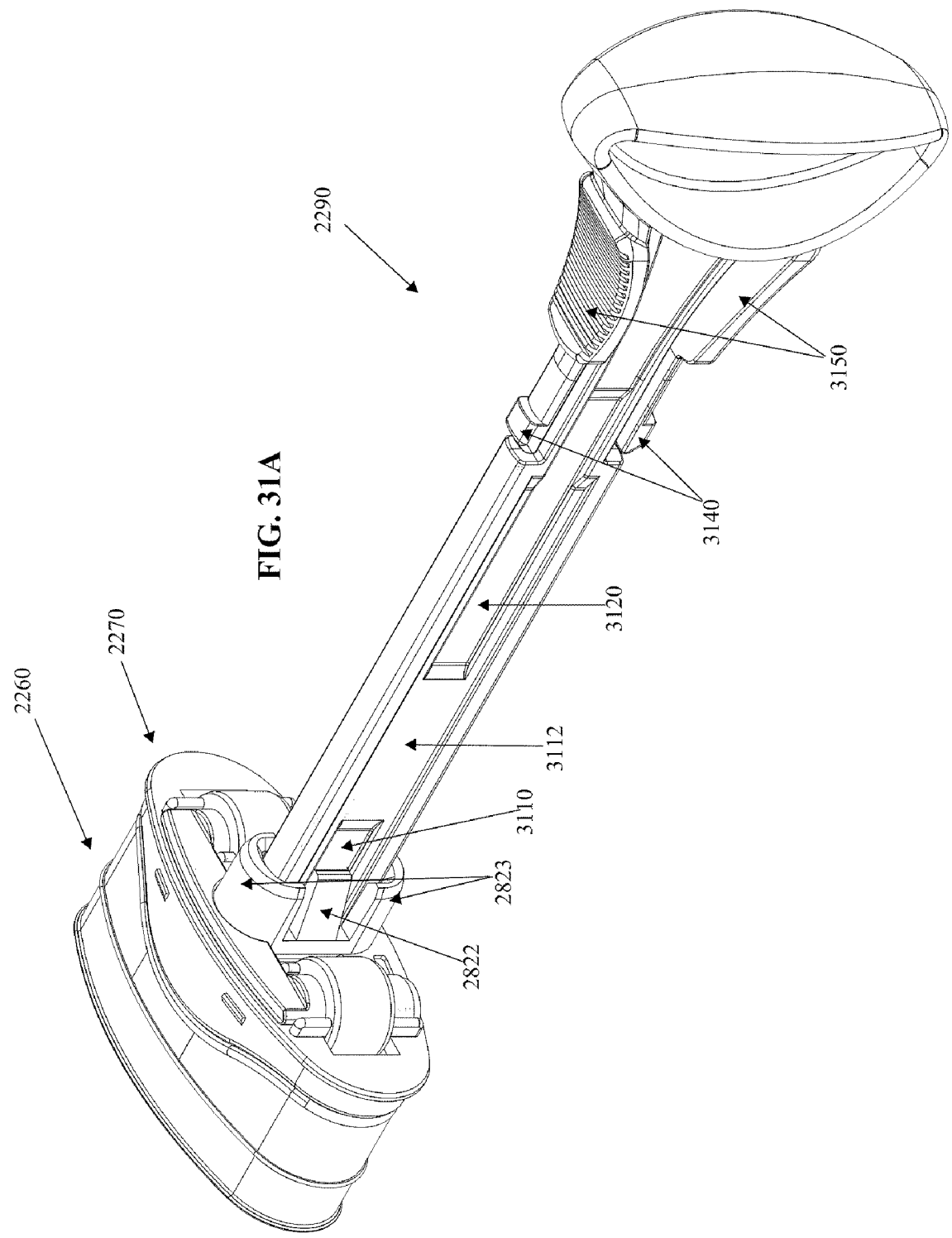

DEVICES AND METHODS FOR TREATMENT OF DAMAGED TISSUE

CROSS-REFERENCE TO RELATED APPLICATIONS

This application is a continuation of U.S. patent application Ser. No. 12/372,661, filed on Feb. 17, 2009, which claims the benefit of priority to U.S. Provisional Patent Application Ser. No. 61/028,835, entitled "Devices and Methods for Treatment of Damaged Tissue," filed on Feb. 14, 2008, which are hereby incorporated by reference herein in their entirety.

BACKGROUND

The use of sub-atmospheric pressure to treat wounds can be traced back to ancient civilizations. For example, the ancient Chinese used "Cupping," a technique that creates reduced pressure environment by flaming a glass chamber to draw out bad humors from the body. Modern research has revealed that applying reduced pressure to a damaged tissue may have several beneficial effects: 1) a reduced pressure level may lead to retraction of the damaged tissue edges and thus may reduce the defect size and may expedite healing by facilitating wound contraction; 2) the reduced pressure may provide mechanical stimulation to the damaged tissue which may release growth factors at the wound bed to promote healing; 3) the reduced pressure may create suction in the damaged tissue cavity which may remove necrotic tissue from the damaged tissue cavity and may reduce bacterial load; 4) the application of reduced pressure may increase blood flow to the damaged tissue and, which may expedite healing; and 5) reduced pressure may remove granulation inhibiting metalloproteinase enzymes, which may enhance tissue remodeling and healing.

In light of the many benefits of reduced pressure tissue therapy, reduced-pressure wound treatment systems and methods are desirable.

BRIEF SUMMARY

Methods and devices for treatment of damaged tissue are disclosed, including treatment of wounds by employing non-electrically powered reduced pressure therapy devices. Maintenance and control of the sub-atmospheric pressure generated may be provided by such devices while minimizing usage discomfort to the user. In some embodiments, the reduced pressure therapy device comprises a suction apparatus, a sealant layer, a contact matrix and optional extension tubing. The suction apparatus may be a non-electrically powered device, which may be configured to be silent and/or wearable. In some embodiments, the suction apparatus may have a low-profile so that it may be worn inconspicuously under clothing. The sealant layer may create a substantially airtight enclosure over the damaged tissue to provide fluid communication between the suction apparatus and the enclosure containing the damaged tissue. Fluid communication may be provided by a direct connection between the suction apparatus and the sealant layer, or may be provided through extension tubing connecting the suction apparatus and the attachment port. In some embodiments, the sealant layer may be flexible, but in other embodiments the sealant layer may be semi-rigid or rigid. In some examples, a semi-rigid or rigid sealant layer may facilitate handling or application of the sealant layer to a treatment site while reducing or eliminating the risk that the sealant layer may fold and adhere on itself. The extension tubing may be coupled to the sealant layer and/or suction apparatus using a connector or fitting. The connector may optionally comprise a releasable locking mechanism to facilitate attachment and detachment of the extension tubing, and/or to prevent accidental disconnection. For example, the releasable locking mechanism may comprise a release button or other actuator which serves as a locking mechanism which may be manipulated during attachment and/or detachment of the tubing. In other embodiments, the suction apparatus may be connected directly to the sealant layer attachment port, and may comprise a connector with the same or similar connector as the extension tubing, to permit both direct attachment of the suction apparatus and remote attachment using the tubing.

In some embodiments the therapy device comprises a variable volume chamber configured to generate reduced pressure and to collect any aspirated fluid or materials. The chamber may be actuated using constant force springs which are coupled to a movable portion of the variable volume chamber. By expanding or biasing the variable volume chamber to an increased volume, the volume of air enclosed by the variable volume chamber and the enclosure sealed by the containing the damaged tissue may be expanded, thereby reducing the pressure of the air.

In some embodiments, the reduced pressure therapy device comprises a non-circular suction chamber design which may provide the therapy device with a low or reduced profile. In some examples, the low profile permits placement of the reduced pressure system on the body near the wound, with or without the use of extension tubing. This ergonomic chamber design coupled with the integrated system configuration may permit discrete wearing of the devices to enhance life quality. In one particular example, the suction apparatus comprises a variable volume chamber with an oval cross-sectional geometry that provides a substantial exudate handling capacity while also providing a low profile. This permits improved mobility, discretion, flexibility, and/or comfort during treatment. The low-profile geometry may also streamline the workflow of using the reduced pressure therapy system by locating the suction apparatus at or adjacent to the treatment site, rather than a remote site, and may also eliminate the use of extension tubing to maintain fluid communication between a treatment site and a separate suction apparatus.

The sealant layer may also comprise an attachment port to facilitate attachment and/or detachment of the suction apparatus or extension tubing to the sealant layer. In some examples, the attachment port may have a variety of relative configurations and/or relative positions with respect to the sealant layer and the suction apparatus. In some instances, the attachment port may be articulated and/or flexible. For example, an attachment port may be configured with a swivel base, which may permit the attachment port to rotate. An articulated and/or flexible attachment port may also reduce the transmission of torsion or other forces that may be transmitted between the suction apparatus and the sealant layer. The attachment port may be integrally formed with sealant layer at the point of manufacture, or may be provided separately and attached to the sealant layer at the point of use. The latter embodiments may permit clinician flexibility or customization of the relative location of the attachment port with respect to the sealant layer. The attachment port configuration may also provide improved patient comfort as the attachment port design minimizes communication of torsion forces to the wound bed, which may be caused by the suction apparatus movements, while allowing quick integration. Furthermore, ability to bend and/or rotate allows independent placement of the sealant layer with respect to the attachment port orientation. The flexibility of the attachment port may also reduce the risk of pressure point induced injury. The attachment port may allow for simple snap-in attachment of the vacuum source. The connection of the attachment port nozzle to the dressing interface may have a small footprint and/or a low profile to reduce the possibility of pressure point injury. In some embodiments, the swivel base of the attachment port may have a thin elastomeric base which is integrated into the sealant layer. The swivel base is configured to allow maximal sealant layer moldability while maintaining integration with the more rigid system elements to form a seal around body surfaces. In some embodiments, a reduced pressure therapy device with an attachment port may reduce or eliminate one or more steps that are used to attach the reduced pressure source to the sealant layer and to create fluid communication between the wound and reduced pressure source. Unlike existing reduced pressure therapy systems, the attachment port may be configured to attach the vacuum source without adhesives and/or without cutting the sealant layer.

In some embodiments, the reduced pressure therapy device may be configured with one or more actuators to facilitate activation of the suction apparatus and/or release of the suction apparatus from the skin or tissue. For example, the suction apparatus may comprise an activation mechanism. In some embodiments, the suction apparatus contains a button or other actuator which initiates the application of reduced pressure at the treatment site. The activation mechanism may be provide with indicia, such as the word "ACTIVATE" or a color green, or any other word or coding with similar meaning, is provided thereon or nearby. Pressing the said button may open a valve and allow fluid communication between the enclosure formed adjacent to the wound bed and the suction chamber, or may unlock a sliding seal to permit movement. More specifically, the activation may cause constant force springs to retract in order to expand the combined volume of the space below the sliding seal and within the wound enclosure. The reduced pressure created therein may exert a force on the sliding seal substantially equal to that of the springs.

In some embodiments, the reduced pressure therapy device may further comprise an additional button or actuator which is configured to close the valve and/or decouple the suction apparatus from the extension tubing or sealant layer enclosing the wound. Pressing the additional button may allow detachment of the suction apparatus from the attachment port or the extension tubing and activate a one way valve which traps the exudates within the suction chamber or otherwise closes any pathway out of the suction chamber.

In some embodiments, the therapy device may be primed or charged prior to applying the reduced pressure. In some configurations of the device, the charging and activating method may be performed in a single continuous step. While in other configurations, the charging and the activating method may be performed in distinctly separate steps. In one example, the sliding seal within the suction apparatus may be primed by being positioned at the distal end of the suction apparatus. The positioning of the sliding seal may be performed by any of a variety of priming mechanisms, such as a slider or push rod, for example. In some embodiments, the sliding seal may automatically begin to slide back to generate a pressure differential in the reduced pressure chamber after priming. In other embodiments, the suction apparatus may comprise an activating mechanism which is actuated separately from a priming mechanism to initiate the generation of the pressure differential. In some configurations, the activating mechanism may directly block or restrict movement of the sliding seal, while in other configurations, the activating mechanism may restrict or limit flow of fluid and/or materials into the chamber of the suction apparatus. In one example, the release mechanism may comprise a separate button or lever that is configured to alter communication or flow through a valve coupled to the reduced pressure chamber. The valve may be a blade valve or rotatable valve, for example. Pressing the activation button may lift a blade valve or turn the lever of a rotatable valve to permit fluid flow into the reduced pressure chamber.

In certain embodiments, the priming mechanism comprises a priming key or tool configured extend the force mechanism or displace the sliding seal into its primed position. In some examples, the priming tool comprises an elongate rigid member that is configured to be positioned in an opening in the body of the suction apparatus and may be used as a lever or push rod to prime the reduced pressure generation mechanism. In some embodiments, the priming tool can be used to mechanically press the sliding seal towards the distal end of the suction apparatus until a latch, embedded within the shaft of the priming tool, locks into place. In some embodiments the priming tool is integrated into the body of the suction apparatus and may also serve as a cap to close the suction apparatus. In some embodiments, the priming tool may be configured to hold and maintain the suction apparatus in a non-charged state. For example, the priming tool may be releasably locked to the body of the suction apparatus to provide safe storage of noncharged suction apparatus, with the locked priming tool preventing or limiting a non-charged spring mechanism from retracting during storage and/or handling. In some instances, without the priming tool in place, retraction from storage and/or handling may occur, due to micro-leaks out of the suction chamber that may cause the springs to lose the energy stored in them, for example. In other embodiments, the priming tool enables re-charging of the spring or other force mechanism that has been depleted or otherwise lost some charge. For example, recharging may be performed when accidental discharge or an undetected leak causes the springs to lose the energy stored in them, or after emptying the collection chamber.

Provided here is a tissue therapy device for treating a damaged tissue. In one embodiment, the device comprises a sealable wound covering and a reduced pressure generating device. In some embodiments, the reduced pressure generating device may be wearable and configured to substantially maintain its external dimensions over a range of collection volumes. In addition, the reduced pressure generating device may have a non-circular cross-sectional shape. In some embodiments, the reduced pressure generating device may be non-electrically powered. In such an embodiment, the reduced pressure generating device may further comprise an elastic force member. For example, the force member may be a constant force spring. In an embodiment where an elastic force member is used, the reduced pressure generating device may be adapted to be mechanically charged with potential energy. In some embodiments, the reduced pressure generating device may comprise a substantially non-cylindrical shape. In such an embodiment, the device may comprise at least two suction chambers. In some instances, these multiple suction chambers may operate independently. In some embodiments where the reduced pressure generating device comprises more than one suction chamber, the device may further comprise at least one collection chamber that is separate from the suction chambers.

Also provided herein is a device for treating a patient. In one embodiment, the device comprises a sealable wound covering and a non-circular reduced pressure generating apparatus. In some embodiments, the sealable wound covering may further comprise a cover and an integrated flexible attachment port, which may be configured to swivel around a swivel axis perpendicular to the cover. In some instances, the attachment port may be configured to permit fluid communication through the sealable wound covering and with the reduced pressure generating apparatus. In some embodiments, the non-circular reduced pressure generating apparatus may further comprise a suction chamber, which may be configured to generate reduced pressure. In addition, the suction chamber may be further configured to self-maintain a constant level of reduced pressure across a volume range. In some embodiments, the reduced pressure generating apparatus may be configured to maintain a constant external configuration over a range of collection chamber volumes. In some embodiments the volume of the suction chamber may be at least 50 cc, but in other embodiments, the volume of the suction chamber may be at least 100 cc. In some further embodiments of the device described herein, the reduced pressure generating apparatus may comprise an elastic force member. In such an embodiment, the reduced pressure generating apparatus may be configured to mechanically recharge the elastic force member. In some embodiments, the reduced pressure generating apparatus may be non-electronically powered.

Also provided herein is a device for treating a patient. In one embodiment, the device comprises a sealable wound covering and a non-circular reduced pressure generating device. In some embodiments, the sealable wound covering may further comprise an integrated flexible attachment port, which may be configured to provide fluid communication through the wound covering and to seal around a wound to form a wound enclosure. In some embodiments, the attachment port may be configured to swivel substantially parallel to the sealable wound covering. In some embodiments, the non-circular reduced pressure generating device may further comprise an elastic force member and a rigid member configured to charge the elastic force member with potential energy. In such an embodiment, the elastic force member may be a constant force spring. In some embodiments, the reduced pressure generating device may be non-electrically powered. In addition, the reduced pressure generating device may be further configured to maintain a substantially constant pressure level irrespective of the orientation of the reduced pressure generating device with respect to gravity. In some further embodiments, the reduced pressure generating device may be configured to maintain fixed external dimensions irrespective of the suctioned or collected volume in the reduced pressure generating device.

Further provided herein is a system for treating a patient. In one embodiment, the system provided herein comprises a sealable wound covering and a non-electronically powered reduced pressure generating assembly. In some embodiments, the sealable wound covering may further comprise a sealant layer and a flexible attachment port, which is configured with a lumen that passes through the sealant layer. In some embodiments, the system may further comprise at least one substantially constant force member. In other embodiments, the system may further comprise at least two substantially constant force members. In some instances, at least one force member is elastic. In some examples, at least one elastic force member is a constant force spring. In an embodiment where a constant force member is used, the reduced pressure generating assembly may further comprise an elongate rigid member that is configured to mechanically charge at least one constant force member. In a further embodiment of the reduced pressure generating assembly described herein, the reduced pressure generating assembly comprises a seal assembly, which may be configured to slide in the suction chamber along a movement axis. In such an embodiment, the reduced pressure generating assembly may be configured to maintain a fixed outer dimension along the movement axis independent of suction chamber content. In addition, the reduced pressure generating assembly may be configured to maintain a fixed outer configuration independent of suction chamber content. In an embodiment where a seal assembly is used, the non-planar proximal perimeter of the seal assembly may be a curved non-planar proximal perimeter. The reduced pressure generating assembly may comprise at least one variable force member, and in some further examples, at least one variable force member is configured to offset at least some friction acting on the seal assembly. In further examples, the reduced pressure generating assembly comprises at least one ribbon spring, which may be a substantially constant force ribbon spring or a variable force ribbon spring.

In a further embodiment of a system for treating a patient where the system comprises a reduced pressure generating assembly, the reduced pressure generating assembly may comprises a first dimension, a second dimension perpendicular to the first dimension, and a third dimension perpendicular to the first and second dimensions. In some instances, the first dimension is the largest dimension of the reduced pressure generating assembly. In other instances, the second dimension is greater than the third dimension. In some embodiments the third dimension may be no greater than about 5 cm, but in other embodiments, the third dimension may be no greater than about 4 cm, about 3 cm, about 2 cm, or about 1 cm. In some embodiments where the reduced pressure generating assembly comprises a suction chamber, the suction chamber may have a volume of about 500 cc or less. In other embodiments, the suction chamber may have a volume of about 250 cc or less. In still other embodiments, the chamber may have a volume of about 100 cc or less. In some embodiments, the reduced pressure generating assembly may be configured to reduce the pressure under the sealable wound covering by at least about 75 mm Hg. In other embodiments, the reduced pressure generating assembly may be configured to reduce the pressure by at least about 100 mm Hg. In still other embodiments, the reduced pressure generating assembly may be configured to reduce the pressure by at least about 125 mm Hg.

In a further embodiment where the system for treating a patient comprises an elongate rigid member, such elongate rigid member may comprise a releasable locking mechanism. In some instances, the releasable locking mechanism may comprise a latch and a release button couple to the latch. In an embodiment where the system for treating a patient comprises a seal assembly, the seal assembly may comprise at least one curved surface that is configured to push against at least one constant force member. In such an embodiment, the seal assembly may further comprise at least one convex structure that is different from the above mentioned curved surface. In another embodiment, a system for treating a patient may comprise a sealable wound covering and a non-electrically powered reduced pressure generating assembly, wherein the reduced pressure generating assembly further comprises a valve. In some instances, the valve is configured to control fluid communication with a suction chamber contained in the reduced pressure generating assembly. In some embodiments, the valve may be coupled to a rotatable knob. In yet another embodiment, the system for treating a patient may further comprise a connector tube that is configured to be coupled to the sealable wound covering and to the reduced pressure generating assembly.

Further provided herein is a system for treatment of a patient, where the system comprises a reduced pressure generating assembly and a sealable wound covering, which further comprises a sealant layer and a flexible attachment port configured with a lumen that passes through the sealant layer. In some embodiments, the reduced pressure generating assembly comprises a removable suction chamber with a longitudinal axis and a non-circular cross-sectional shape transverse to the longitudinal axis and a volume of 150 cc or less. The reduced pressure generating assembly may further comprise a piston assembly that is configured to slide in the suction chamber along the longitudinal axis. In some instances, the piston assembly may have a non-circular cross-sectional shape transverse to the longitudinal axis and a non-planar proximal perimeter. The reduced pressure generating assembly may further comprise at least two substantially constant force spring coils, which are coupled to the piston assembly and configured to reduce pressure in the suction chamber by at least about 50 mm Hg. In some embodiments, the reduced pressure generating assembly may further comprise a priming tool that is configured to push the piston assembly. In some instances, the priming tool may have a locking mechanism. In still other embodiments, the reduced pressure generating assembly may further comprise a connector tube that is configured to releasably attach to the sealable wound covering and to releasably attach to the removable reduced pressure chamber.

In another embodiment, a method for treating a patient is provide, where the method comprises steps of (a) detaching a non-electrically powered and non-circular reduced pressure generating device from a wound covering, (b) charging the reduced pressure generating device with potential energy without generating a reduced pressure, (c) attaching the recharged reduced pressure generating device to the wound cover, and (d) activating the recharged reduced pressure generating device to generate reduced pressure in an enclosure underneath the wound covering.

Further provided herein is a method for treating a patient, where the method comprises steps of (a) sealing a wound cover to a body site, and (b) reducing the pressure level at the body site using a vacuum generating device that has an elongate length and a non-circular cross-sectional shape transverse to the elongate length. In some embodiments, the vacuum generating device may be configured to maintain substantially constant reduced pressure level at the wound site without changing its external dimensions and independent of its orientation with respect to the body site. In such an embodiment, the method may further comprise a step of sliding a non-circular seal along a movement axis in a non-circular reduced pressure chamber, wherein the seal and the suction chamber have non-circular configurations transverse to the movement axis.

BRIEF DESCRIPTION OF THE DRAWINGS

A better understanding of various features and advantages of the embodiments described herein may be obtained by reference to the following detailed description that sets forth illustrative examples and the accompanying drawings of which:

FIG. 9A to 9D are schematic illustrations of a reduced pressure therapy device in various configurations; FIG. 9A depicts the device in a primed and locked configuration; FIG. 9B depicts the device in a primed and unlocked configuration; FIG. 9C depicts the device in an activated configuration; FIG. 9D is a cross-sectional view of a portion of the priming tool in FIG. 9C.

FIG. 11A is a perspective view of another embodiment of a reduced pressure therapy device comprising multiple chambers; FIG. 11B is an end view of the device in FIG. 11A; FIG. 11C-11E illustrate various embodiments of a reduced pressure therapy device with multiple chambers with respect to a sealant layer. FIG. 11F is a perspective view of the embodiment from FIG. 11A with a body strap.

FIG. 21A is a perspective view of a reduced pressure therapy device comprising a viewing window and a vacuum indicator; FIGS. 21B and 21C are perspective views of other examples of reduced pressure therapy devices with various window configurations.

FIGS. 28A and 28B are posterior and anterior component views of one embodiment of a spring assembly, respectively.

FIGS. 29A and 29B are posterior and anterior perspective component views, respectively, of one embodiment of a piston assembly and spring assembly.

FIGS. 31A to 31C are schematic perspectives views depicting one example of a priming procedure using a priming tool.

DETAILED DESCRIPTION

Figure 1:
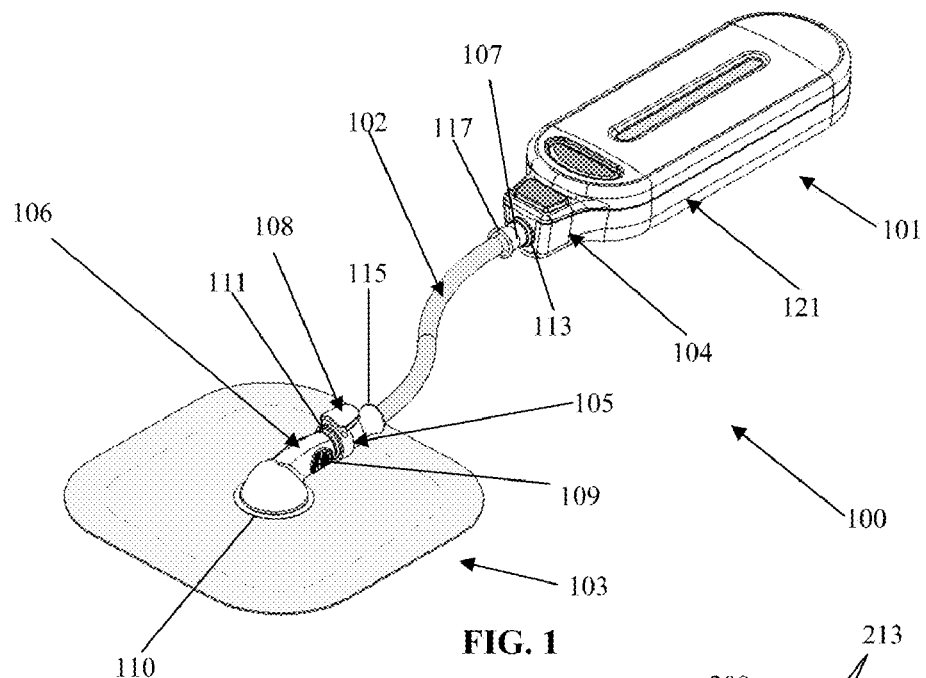
FIG. 1 is a perspective view of one embodiment of the reduced pressure therapy device comprising a suction apparatus, an extension tube and a sealant layer.

While embodiments have been described and presented herein, those embodiments are provided by way of example only. Variations, changes and substitutions may be made without departing from the invention. It should be noted that various alternatives to the exemplary embodiments described herein may be employed in practicing the invention. For all of the embodiments described herein, the steps of the methods need not to be performed sequentially.

Modern adaptations of techniques to provide reduced pressure to wounds have been developed recently. There are several commercially available models of these types of reduced pressure dressing systems. These devices may comprise an interface layer that is placed into the wound, an occlusive layer that creates a seal around the wound, connection tubing that is in fluid communication with the interface layer and the wound, a separate exudates collection canister, and an electric pump that provides a source of vacuum. However, the electric pumps are bulky and heavy thereby reducing patients' mobility especially during prolonged treatment periods. These electrical pumps, in operation, can be noisy and conspicuous. Further, the placement of the interface layer, the occlusive layer, and the connection tubing is labor intensive and time consuming increasing patient dependence on health care professionals and further leading to higher health care costs. These systems typically have non-disposable pumps and systemic components that require significant maintenance and servicing and that carry the risk of spreading contamination and infection. Although these systems can be used to treat smaller wounds, they are designed to treat large wounds and are not usually used to treat smaller wounds. Since current systems depend on electrical power for their operation, they further constrain patient movement to areas having electricity or rely on limited battery power where no electricity is available.

Described herein are devices configured to apply reduced air pressure (i.e., a vacuum) to a treatment site, such as a damaged tissue cavity or other type of wound. In some embodiments, the device may also be used to apply reduced pressure to otherwise undamaged tissue. In one embodiment, the tissue therapy device may comprise a sealant layer and a suction apparatus. The sealant layer may be used to create a seal around an area of tissue requiring therapy. The suction apparatus fluidly communicates with the sealed enclosure formed by the sealant layer and reduces pressure within the enclosure adjacent to the damaged tissue. In some embodiments, the suction apparatus may be non-electrically powered. For example, the suction apparatus may be configured to self-generate reduced pressure, i.e., without requiring a separate power or vacuum source. A reduced pressure therapy device comprising a self-generating reduced pressure mechanism may provide a patient with freedom and mobility without concerns of running out of battery power or having access to an electrical outlet or vacuum generator. The sealant layer and the suction apparatus may be used to form a closed reduced pressure system to resist the backflow of gas into the system.

The reduced pressure may be self-generated by expanding the volume of air initially located in the sealed enclosure and/or suction apparatus from a smaller volume of the enclosure to a larger volume shared between the sealed enclosure and the suction apparatus. Upon expansion of the air within the sealed enclosure, the density of the air molecules is decreased and the pressure within the sealed enclosure is reduced to a sub-atmospheric level.

In one embodiment the tissue therapy device comprises a contact layer matrix that is placed into or over the wound bed or other tissue defect. In some embodiments, the contact layer matrix may be used to distribute the reduced pressure more evenly through the wound bed, and may also provide a scaffold or contact surface which promotes healing. In another embodiment, the damaged tissue cavity, packed with the contact layer matrix, is then placed under a sealant layer to produce a sealed enclosure containing the contact layer and the wound bed. Fluid communication to the interior of enclosure is provided by an attachment port of the sealant layer.

In some embodiments, the attachment port may comprise a collar with an inlet opening, a soft elastomeric body, and an outlet port. In some examples, the collar may comprise a rigid or flexible material, and the collar may be oriented at any of a variety of angles with respect to the sealant layer, including a perpendicular angle. The outlet port of the attachment port may also be flexible or rigid, and may be oriented at any of a variety of angles with respect to the sealant layer or collar. In some examples, the outlet port may be oriented generally parallel to the plane of the sealant layer, or even below the parallel plane of the sealant layer, depending upon the height of the collar, but in other examples, the outlet port may be bent or angle above the plane of the sealant layer. The various components of the attachment port may or may not be directly connected to one another, and the inlet and the outlet may have some degree of freedom of movement relative to one another.

In some embodiments of the device, the device may comprise a sealant layer made of a hydrocolloid material or any other material known to those skilled in the art. The hydrocolloid sealant layer may be semi-porous and breathable to absorb moisture from the wound while protecting the skin. In addition, the hydrocolloid sealant layer is typically thicker than other materials such as acrylic adhesives to allow for easier placement with less folding and wrinkling and to seal potential fluid leak paths.

In one embodiment of the device disclosed herein, the attachment port is directly mounted to a distal portion of the suction apparatus. In other embodiments the attachment port is connected to the suction apparatus via an extension tube. In some embodiments, the extension tube may be adapted to mitigate entanglement. The suction apparatus and the extension tubing may have similar fittings and release buttons to prevent accidental disconnection. In embodiments in which extension tubing is used, the distal end of the extension tubing is connected to the distal end of the suction apparatus with similar fitting.

Some embodiments of the device disclosed herein comprise a pressure gauge integrated into the attachment port or another component. The mounting of the pressure gauge into the attachment port enables accurate measurement of pressure level within the enclosure adjacent to the wound and formed by the sealant layer. The pressure gauge described herein may less susceptible to incorrect pressure readings that are typically caused by clots in the tubing connecting the reduced pressure source to the wound.

In some embodiments of the reduced pressure system disclosed herein, the suction apparatus reduces the air pressure within the enclosure adjacent to the damaged tissue by forcefully expanding the volume of air within the enclosure without changing the external dimensions of the reduced pressure generating unit. In other embodiments, the tissue therapy device may self-regulate the pressure to a substantially constant level.

In one embodiment, the suction apparatus comprises a chamber, a sliding seal, a valve, and an activation system. The suction cartridge may comprise a release button and an activation button in a distal portion. The activation button may be connected to a sliding blade valve which prevents fluid communication from the enclosed area adjacent to the wound to the chamber when in the "off" position. When the activation button is depressed, the sliding blade valve may switch to an "on" position to permit fluid communication from the enclosure to the chamber. The activation button may be spring loaded to be biased to the "off" position but once it is depressed, a spring-loaded latch may engage to remain in the "on" position. The release button may be adapted and configured to allow detachment of any article (e.g., extension tubing or sealant layer attachment port) from the suction apparatus and to terminate fluid communication between the suction chamber and the enclosed area. The release button may engage the interlock segment to pull the latch away from the activation button. If the activation button is in the "on" position, it will revert back to the "off" position by virtue of the spring loading.

In one embodiment of the reduced pressure system, the suction chamber comprises an ellipsoidal cylinder having a sliding seal concentrically disposed therein. The chamber has a variable effective volume defined by the distance between the distal end of the chamber, which is located adjacent to the opening connected to the sliding blade valve and a current position of the sliding seal. In the primed state, the seal is closest to the distal end of the suction cartridge, and the effective volume of the chamber is zero or nearly zero. The sliding seal may be connected to one or a series of springs which may be used to bias the seal towards an activated state where the effective volume of the chamber is the maximum. The springs may have any of a variety of configurations, including ribbon springs. The ribbon spring may be a substantially constant force spring or a variable force spring. In some examples, a combination of spring types may be used. In still other examples, a single ribbon may be configured with a coil at each end and attached to a slidable seal at a middle region of the single ribbon. In one embodiment of the device, the spring(s) may exert a force of less than 0.5 pounds. In other embodiments of the present invention the constant force spring(s) may exert a force of less than 1 pound. In some embodiments of the reduced pressure system the constant force spring(s) may exert a force of less than 5 pounds. In other embodiments of the device disclosed herein the substantially constant force spring(s) may exert a force of less than 20 pounds. In other examples, the force per square inch exerted across the collection volume of the device may be in the range of about 0.1 psi to about 50 psi, in some examples about 0.5 to about 20 psi, and in other examples about 1.5 psi to about 5 psi. This pressure may be exerted by a single force member or may be the aggregate pressure from two or more force members. The force or pressure may be selected based on the type, size, location, or another suitable characteristic of the wound being treated.

In some embodiments of the tissue therapy system the suction cartridge is fabricated from a rigid polymer adapted to maintain the external shape of the suction chamber shape under reduced pressure. The suction chamber can be made of any suitable polymer such as, but not limited to polycarbonate, co-polyester, polyethylene, polypropylene, acrylic, ABS, glass, medical-grade polymers, or a combination thereof.

In other embodiments of the reduced pressure system, the sliding seal is fabricated from a material adapted to create an airtight separation between the portion of the suction apparatus below it and the remainder of the suction apparatus. The material may be elastomeric or non-elastomeric. The sliding seal can be made of materials such as: silicone, fluorosilicone, nitrile, natural rubber, thermoplastic elastomer, thermoplastic urethane, butyl, polyolefin, polyurethane, styrene, polytetrafluoroethylene, any other suitable material, or a combination thereof.

In some embodiments of the tissue therapy system, the suction cartridge may be coated using a friction mitigating lubricant to reduce movement of the sliding seal due to friction within the suction chamber and to reduce the likelihood of the seal sticking after being in a static position for prolonged periods. The lubricant coating material may be polydimethysiloxane, perfluoropolyether, mineral spirits, synthetic oils, polyxylene, any other suitable lubrication polymer or material, or any combination thereof.

In one embodiment of the reduced pressure system disclosed herein the suction apparatus springs are placed in a high potential energy extended state prior to activation. In other embodiments of the device, prior to activation, the sliding blade valve is closed and the chamber is completely sealed. In such embodiments, the springs are prevented from retracting because the extremely small volume of air in the chamber resists the expansion that would be caused by the constant force springs' retraction of the sliding seal. The device is ready to be activated once the wound bed is sealed with the sealant layer, and the sealant layer is connected to the suction cartridge either directly or via an extension tube.

When the tissue therapy system disclosed herein is activated, fluid communication is established between the suction chamber and the sealed wound enclosure. Since there is a finite amount of air within the enclosure (which is initially at atmospheric pressure), upon activation, the constant force springs will retract the sliding seal and expand the effective volume of the suction chamber. As known by the ideal gas law, as a volume of air expands adiabatically, the pressure of the air will be reduced, and subject the sealed wound enclosure to reduced pressure.

In some embodiments, the tissue therapy system may be used to maintain a substantially constant level of reduced pressure despite the presence of exudates and air leaked into the system. The sliding seal is a mechanical system wherein the seal position is adapted and configured to be in equilibrium based on the traction of the substantially constant force springs, other traction elements in the system, and/or the pressure differential across the chamber seal. Other traction elements in the system may include frictional forces (i.e. static and/or kinetic frictional forces). If the reduced pressure were to recover towards atmospheric within the chamber, the pull of the springs would be greater than the pull due to the pressure differential. This, in turn, will force the springs to retract and cause a simultaneous increase in the volume of the chamber. This increase in volume will result in a reduction of pressure away from atmospheric pressure within the chamber, until a new equilibrium is reached where the pressure differential and the substantially constant spring force reach a new equilibrium. In some embodiments, the walls of the suction chamber are straight thereby ensuring that the level of reduced pressure stays constant regardless of the actual position of the seal within the chamber.

In some embodiments, the suction apparatus may be configured to generate a reduced pressure which may be generally characterized by the absolute pressure level and/or by a pressure level reduction relative to the atmospheric pressure. In some embodiments, the device is configured to generate a level of reduced pressure between about 0 and about 760 mmHg. In some embodiments, the generated amount of reduced pressure in the enclosure formed by the sealant layer and treatment site is more than about 10 mmHg, about 20 mmHg, about 50 mmHg, about 80 mmHg, about 100 mmHg, about 150 mmHg, about 200 mmHg, about 500 mmHg, about 700 mmHg, or even about 750 mmHg or more. The device may generate an absolute reduced pressure underneath the sealant layer where the reduced pressure is anywhere between about 0 and about 760 mmHg. In some embodiments, the generated level of reduced pressure in the enclosure formed by the sealant layer is less than about 700 mmHg, sometimes less than about 600 mmHg, other times less than about 400 mmHg, or even less than about 250 mmHg, about 125 mmHg, about 75 mmHg, about 50 mmHg, less than about 25 mmHg, or less than about 10 mmHg. In some embodiments, the sealant layer generally follows the perimeter of the area of tissue being treated. The tissue therapy devices may have different collection chamber sizes which allow for treatment of larger, more exudative wounds while maintaining the smallest configuration possible for enhanced usage comfort. This may be particularly advantageous for small wounds or treatment sites, as a smaller reduced pressure source can be partially or fully integrated into the dressing or sealant layer. In some embodiments, the cavity of the suction apparatus is about 50 cc or less in volume, while in other embodiments, the cavity may be about 100 cc in volume. In other embodiments, the collection chamber is less than about 150 cc in volume. In some embodiments, the collection chamber is less than about 200 cc in volume. In other embodiments, the collection chamber is smaller than about 300 cc in volume. In some embodiments, the collection chamber is less than about 500 cc in volume. In other embodiments, the collection chamber is less than about 1000 cc in volume. In other embodiments, the cavity of the suction apparatus may be at least about 50 cc, about 100 cc, about 150 cc, about 200 cc, about 300 cc, about 500 cc or about 1000 cc or more.

In certain embodiments, the device comprises an elongated rigid member that fits into an opening the proximal end of the suction apparatus and serves as a lever that charges the constant force springs with potential energy by pressing the springs towards the device's distal end until the latch, embedded within said lever, locks into place. In some embodiments, the elongated member is integrated into the suction apparatus body and serves as a cap to the suction apparatus. In some embodiments, the elongated lever enables safe storage of the suction apparatus as it prevents the springs from retracting due to micro-leaks that may cause the springs to lose the energy stored in them. In other embodiments, it enables recharging of the spring mechanism when accidental discharge occurs or an undetected leak is present while the device is in use.

In some embodiments, the suction apparatus comprises an elongated rigid member adapted and configured to be inserted into a mating opening in the proximal end of the suction generating unit. The elongated rigid member contacts the rigid portion of the chamber seal and thus can be used to mechanically push the seal down the chamber against the constant force springs thereby imparting potential energy into the constant force springs. This pushing motion is completed with the suction cartridge disconnected from the extension tubing or attachment port, and with the activation button and the sliding blade valve in the off position. Once the sliding seal reaches a point close to maximum spring extension, a latch tab on the elongate rigid member will engage a slot in the suction apparatus body and prevent spring retraction. At this point, the sliding blade valve should be closed by depressing the release button thereby sealing the chamber. The elongate member can then be removed by pressing the latch tab leaving the suction apparatus ready for activation.

FIG. 1 illustrates one embodiment of a reduced pressure therapy device 100, comprising a suction apparatus 101, an extension tube 102, and a sealant layer 103. The sealant layer 103 may further comprise an integrated attachment port 106 configured to connect the sealant layer 103 to the extension tube 102 and/or directly to the suction apparatus 101. In some embodiments, the connector of the extension tube 102 or suction apparatus 101 may be configured to rotate about an axis of attachment port 106. In some embodiments, the attachment port 106 may be configured to rotate around its base 110 and/or to bend toward and/or away from the sealant layer 103. For example, the attachment port 106 may be configured to freely rotate about 360 degrees or more, or to provide a limited rotation range less than about 360 degrees, including but not limited to about 315 degrees, about 270 degrees, about 225 degrees, about 180 degrees, about 135 degrees, about 90 degrees, or about 45 degrees, for example. In other embodiments, the tubing connector and/or the connector interface of the attachment may be configured to rotate with respect to the longitudinal lumen axis. The attachment port 106 may have a fixed orientation that is generally parallel to the plane of the sealant layer, but in other configurations, may be angled below the parallel plane or above the parallel plane. In still other examples, the attachment port 106 may be configured to bend or pivot relative to the sealant layer 103. The range of bending or pivoting may be from about 0 degrees to about 45 degrees or about 90 degrees, from about 0 degrees to 135 degrees or about 180 degrees, or from about −15 degrees or about −30 degrees to about 45 degrees, about 90 degrees, about 135 degrees, about 180 degrees, 195 degrees or about 210 degrees. In certain embodiments, the attachment port 106 may be configured to rotate and pivot.

The extension tube may be coupled to the attachment port by any of a variety of mechanisms. For example, the attachment port may comprise a resistance or interference fitting which may be inserted into the lumen of the extension tube. The resistance fitting may comprise one or more flanges configured to resist decoupling of extension tube. In other examples, the extension tube may be inserted into the lumen or opening of the attachment port, and the attachment port may comprise a push-in fitting, such as a John Guest fitting (Middlesex, UK). In other embodiments, connectors on both components may be used, including threaded or mechanical interlocking fits. The connectors may be configured to facilitate both coupling and decoupling of the components.

In the example depicted in FIG. 1, one end of the extension tube 102 comprises a port connector 105 configured to couple to a connector interface 111 of the attachment port, and the other end may comprise a suction apparatus connector 107 configured to couple to a connector interface 113 of the suction apparatus 101. In the depicted embodiment, the connector interface 111 of the attachment port 106 and the suction apparatus connector 107 of the extension tube 102 may comprise male-type connectors, while the connector interface 113 of the suction apparatus 101 and the port connector 105 of the extension tube 102 may comprise female-type connectors. The particular male-female configuration described above is merely exemplary, and in other embodiments, the male/female configuration may be reversed, any other type of complementary interface may be used, including interfaces which are non-directional and permit the connector of the extension tube 102 in any direction. These or other complementary configurations may be used to permit both the direct connection of the suction apparatus 101 and the sealant layer 103, as well as the optional use of the extension tube 102. In some embodiments, the extension tube(s) and/or the extension tube connector(s) may be configured so that multiple extension tubes may also be joined together, either in a specific order or in any order. The extension tube may also comprise one or more stress-relief or anti-kink structures, e.g. a helical winding or other tubular support, which may resist pinching or other deformations of the tube. In FIG. 1, for example, the port connector 105 and the suction apparatus connector 107 of the extension tube 102 comprises a flared openings 115 and 117, respectively, which permit at least some deflection of the tube 102 relative to the connectors 105 and 107 while distributing the bending stress along the length of the flared opening 115 and 117 to resist pinching. In other embodiments, the stress relief structures of the connectors comprise one or more bendable or deformable projections, which may or may not be flared.

One or more connectors of the extension tube may also comprise a locking mechanism to facilitate decoupling and/or attachment of the extension tube. In some examples, a locking mechanism may resist inadvertent decoupling from the sealant layer and/or suction apparatus. In the example depicted in FIG. 1, the port connector 105 of the extension tube 102 comprises a locking mechanism with a connector release button 108 configured to resist decoupling until the button 108 is pressed. The connector release button 108 may be coupled to a movable structure that forms an interlocking or resistance fit with a complementary structure or surface on the attachment port 106. In some embodiments, the connector release button 108 may be spring loaded or otherwise biased, and may or may not provide additional sealing and/or locking force between the connector 105 and the attachment port 106. In other variations, other locking interfaces, including sliders, levers or knobs, may be used. The attachment port 106 may comprise one or more gripping materials or textured gripping surfaces 109. The gripping surface 109 on the exterior of the attachment port 106 may facilitate manual connection and disconnection of the connectors on the extension tube 102 or the suction apparatus 101. The grip surface 109 may comprise one or more flanges or ridges, for example, and/or a high traction material such as rubber or a block copolymer with polystyrene and polybutadiene regions, e.g., KRATON® polymers by Kraton Polymers, LLC (Houston, Tex.). Gripping materials or structures may also be provided on the connectors 105 and 107 and/or the suction apparatus 101. In FIG. 1, for example, the suction apparatus 101 comprises a nosepiece 104 having a reduced width relative to the body 121 of the suction apparatus 101. The nosepiece 104 may facilitate gripping of the suction apparatus 101 when detaching or pulling it apart the extension tube 102 or attachment port 106.

In some embodiments, the suction apparatus may comprise a rigid polymer configured to generally maintain its shape under reduced pressure. The suction apparatus can be made of any suitable polymer such as polycarbonate, co-polyester, polyethylene, polypropylene, acrylic, ABS, glass, or any other polymer known to those skilled in the art.

Figure 2:
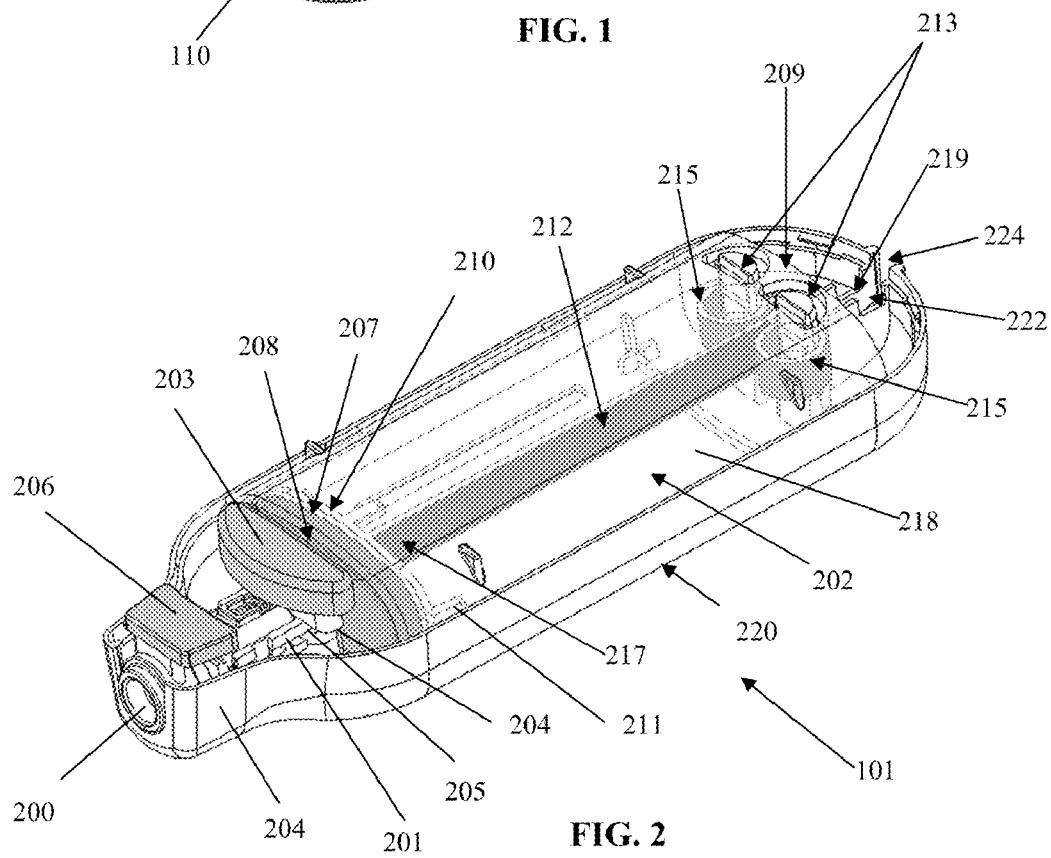
FIG. 2 is a cut-away perspective view of one embodiment of a suction apparatus of FIG. 1 in a primed configuration.
Figure 3:
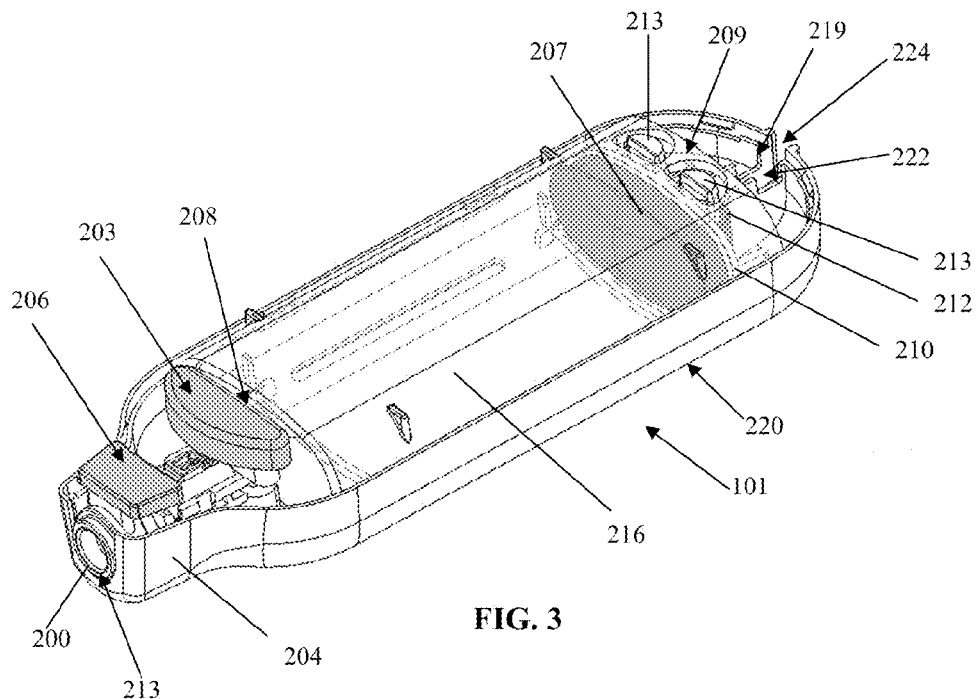
FIG. 3 is a cut-away perspective view of one embodiment of a suction apparatus of FIG. 2 in a depleted configuration.

FIGS. 2 and 3 are detailed views of one embodiment of the suction apparatus 101 in FIG. 1. The connector interface 113 may comprise a connector 200 which may be coupled to the connector 107 at the proximal end of the extension tube 102, and/or the connector interface 111 of the attachment port 106 as depicted in FIG. 1. The suction apparatus 101 may further comprise a sliding seal 207 located inside a suction chamber 202. FIG. 2 depicts the sliding seal 207 in a distal position near the distal end 208 of the suction chamber 202, and FIG. 3 depicts the seal 207 in a proximal position near the proximal end 209 of the suction chamber 202. The sliding seal 207 may be mounted on a seal mount 210 and is configured to traverse between the distal end 208 and proximal end 209 of the chamber 202 while maintaining a substantial airtight seal. The suction chamber 202 may be also be characterized by the portions of the chamber 202 separated by the seal 207. For example, the suction chamber 202 may comprise a collection chamber 216 located between the distal end 208 of the chamber 202 and the seal 207, and a working chamber 218 between the proximal end 209 of the suction chamber 202 and the seal 207. The collection chamber 216 may be configured to generate a reduced pressure and is in fluid communication with the connector 200 to provide reduced pressure under the sealant layer 103. In the particular embodiment depicted in FIGS. 2 and 3, the collection of materials suctioned from a wound and the generation of reduced pressure both occur in the collection chamber 216, but in other embodiments, the collection chamber and reduced pressure generating chamber may be different structures.

The working chamber 218 of the suction apparatus 101 may contain one or more force or bias members, and may also provide access to the seal 207 to permit priming or charging of the force or bias members. A portion of the force or bias members may be attached or fixed to a portion of working chamber 218, while another portion is attached to the seal 207. In the particular embodiment depicted in FIG. 2, the force member comprises two constant force springs 212 with proximal ends 215 mounted in the working chamber 218 using posts or pins 213, while their distal ends 217 are attached a seal mount 210 that is coupled to the seal 207. In some embodiments, the seal 207 and the seal mount 210 may be integrally formed. The sliding seal 207 may mounted on a seal mount 210 by methods such as injection over-mold, adhesive bonding, or mechanical bonding, or by a mechanical resistance or interlocking fit. In other embodiments, the force members may be directly coupled to the seal 207. The functionality and structure of the seal 207 is described in greater detail below.

The volumes of the collection chamber 216 and the working chamber 218 may vary, depending upon the position of the seal 207. In FIG. 2, where the seal 207 is in an extended position and in a primed configuration, the effective volume of the collection chamber 216 may be about zero or close to zero. In FIG. 3, wherein the seal 207 is in a retracted position, the effective volume of the collection chamber 216 may be at or near the volume of the suction chamber 202, notwithstanding the volume taken up by the seal 207, seal mount 210 and/or the bias members. In other examples, the volume of the collection chamber may be generally based upon the equilibration of the force generated by the bias members and the counteracting force resulting from the reduced pressure generated in the collection chamber 216. The volume of the working chamber 218 may be inversely related to the volume of the collection chamber 216. In some instances, the maximum volume of the working chamber 218 may be less than the volume of the suction chamber 202, which may result from volume displacement by the seal 207 or seal mount 210, and/or by other structures located within the working chamber 218 or structures which limit the movement range of the working chamber 218.

Access to the seal 207 may be achieved through the access opening 224 located about the distal end 209 of the housing 220. As the sliding seal 207 traverses from the extended position as depicted in FIG. 2 to the retracted position as depicted in FIG. 3, the interior volume of the collection chamber 216 increases from about zero to about the maximum volume provided in the fully retracted position, the suction apparatus 101 comprises a collection chamber 216 with the maximum effective collecting volume. When the collection chamber 216 is in airtight fluid communication with a sealed wound enclosure and a good dressing seal is obtained within the wound enclosure, expansion of the volume of the collection chamber 216 will reduce the pressure level in the sealed wound enclosure to a point where an equilibrium between the restoring force applied on the sliding seal 207 by the constant force springs 212 and the pressure differential across the sliding seal 207 is reached.

Some embodiments of the suction apparatus 101 may further comprise a valve 201 which may be configured to selectively permit fluid communication between the connector 200 to a collection chamber 216. The valve 201 may have any of a variety of configurations, including a rotating cylinder valve or a blade valve, for example. The valve may also be a multi-directional valve, a bi-directional valve or a one-way valve. The configuration of the valve 201 may be controlled by an activation button 203 or other type of actuator (e.g. a knob, switch, lever or slider). In some embodiments, the activation button 203 may comprise a first configuration where the chamber valve 201 closes or blocks fluid communication between the collection chamber 216 and the connector 200, and a second position where the valve 201 is open or allows passage of air and/or exudates to flow from the connector to the collection chamber 216. In some further embodiments, some valves may have additional configurations to selectively permit infusion of materials into the suction apparatus 101 and/or into the sealant layer, and/or configurations to selectively permit removal of air and/or materials from the collection chamber.

In further embodiments, a spring mechanism 204 may bias the valve 201 or its actuator to a closed or open position. For example, the spring mechanism 204 may be configured to bias the valve 201 to a closed position which blocks fluid communication between connector 200 and the collection chamber 216. When the valve 201 is actuated to open the fluid communication, a latch mechanism 205 or other type of locking mechanism may be used to engage the valve 201 and prevent the spring mechanism 204 from closing the valve 201. The locking mechanism may also comprise a release mechanism configured to permit selective disconnection or separation of an extension tube or sealant layer. For example, the connector 200 may be configured to prevent or resist disconnection of any components connected to the suction apparatus 101 through the connector 200 until a release button 206 or other actuator is depressed or manipulated. The release mechanism may comprise one or more displaceable or movable resistance or interlocking structures, for example. In other embodiments, the lock and/or release mechanism may be located on the extension tube or the attachment port of the sealant layer.

In some embodiments, the release button 206 may comprise a mechanism to control the valve 201. For example, the release button 206 may be configured to disengage the latch 205 from the valve 201, which permits the spring mechanism 204 to reposition the valve 201 to the closed position blocks permit fluid communication between the connector 200 and the collection chamber 216. In other embodiments, the release button 206 may be configured to control a second valve in the fluid communication pathway.

In some embodiments, the suction apparatus 101 may comprise a suction chamber 202 with a non-circular cross-sectional shape, with respect to a transverse or perpendicular plane to the movement axis of the seal 207. The non-circular cross-sectional shape may include but is not limited to a generally rectangular or generally ellipsoidal shape, for example. The suction apparatus 101 may comprise a first transverse dimension that is greater than a second transverse dimension, wherein each transverse dimension is transverse to the movement axis of the sliding seal 407. In some embodiments, the ratio of the first transverse dimension and the second transverse dimension is at least about 1.5, sometimes at least about 2, and other times at least about 3, or about 5 or more.

To prepare the suction apparatus 101 for generating a reduced pressure level in the sealed wound enclosure, the device is primed, i.e., the sliding seal 207 and the substantially constant force springs 212 may be placed in a distal or extended position within suction chamber 202. Priming of suction apparatus 101 may be performed using a push mechanism or tool inserted through an opening 224 configured to provide access to the seal 207 or seal mount 210. Examples of a push mechanism including the priming tool 400 depicted in FIG. 4, which is described in greater detail below. Referring back to FIG. 2, the sliding seal 207 is placed at an extended position, with the constant force springs 212 also in an extended state and charged with potential energy. In some embodiments, when the suction apparatus 101 is primed, the blade valve 201 is closed to seal the collection chamber 216. In these embodiments, retraction of the seal 207 by the constant force springs 212 is resisted or prevented because the small volume of air in the collection chamber 216 resists the expansion that would be caused by the retraction of the constant force springs 212. The suction apparatus 101 may comprise a locking mechanism to keep the sliding seal 207 in the primed position. In some embodiments, the priming mechanism or tool may also be used to keep the sliding seal 207 in position and resist retraction by the constant force springs 212

Once the wound bed is sealed with a sealant layer and the primed therapy device is connected to the suction apparatus, the primed therapy device may be activated to generate reduced pressure in the wound bed. In some embodiments, a user of the therapy device described herein may activate the therapy device by pressing down the activation button 203. In some examples, prior to activation, the activation button 203 may be biased to the "off" position. Pressing down or otherwise manipulating the activation button causes the valve 201 to open fluid communication between the collection chamber 216 and the sealed enclosure. Once the activation button 203 is pressed down, a spring-loaded latch on the interlock piece may engage to keep the activation button 203 in the "on" position.

When the reduce pressure therapy device is activated, fluid communication is established between the sealed wound enclosure and the collection chamber 216. If a sufficient dressing seal is obtained within the sealed enclosure, there should be a finite amount of air and/or exudate within the sealed enclosure which is initially at atmospheric pressure. Upon activation of the suction apparatus 101, the charged constant force springs 212 that are will then retract the sliding seal 207 and expand the volume of the collection chamber 216. Movement of the sliding seal 207 will stop at an equilibrium position where the traction force of constant force springs 212 is equal to the pressure differential across the sliding seal 207.

As the collection chamber is filled with exudates and/or air from potential air leakage into the sealed wound enclosure or other location in the system, the sliding seal 207 will retract towards the proximal end 209 of the suction chamber 202 until the constant force springs 212 reach a retracted position, as depicted in FIG. 3. Further retraction may be stopped either by a limit structure (if any) in the suction chamber 202, or as a result of the decreasing counterbalancing force as the reduced pressure collection chamber 216 returns to atmospheric pressure from increases in the joint volume shared by the wound enclosure and the collection chamber 216. The therapy device may then be removed from the treatment site, or the suction apparatus 101 may be disconnected from the sealant layer 103. As mentioned previously, disconnection may be achieved by pressing or actuating the release button 206. Once the release button 206 is pressed down or actuated, the blade chamber valve 201 will be engaged in its "off" position which will terminate or block any fluid communication between the sealed wound enclosure and the collection chamber 216. Also, the spring-loaded latch 205 on the interlock piece that forces or maintains the activation button 203 in the "on" position will be pulled away or otherwise manipulated to permit the activation button 203 will revert to its "off" position.

Figure 4:
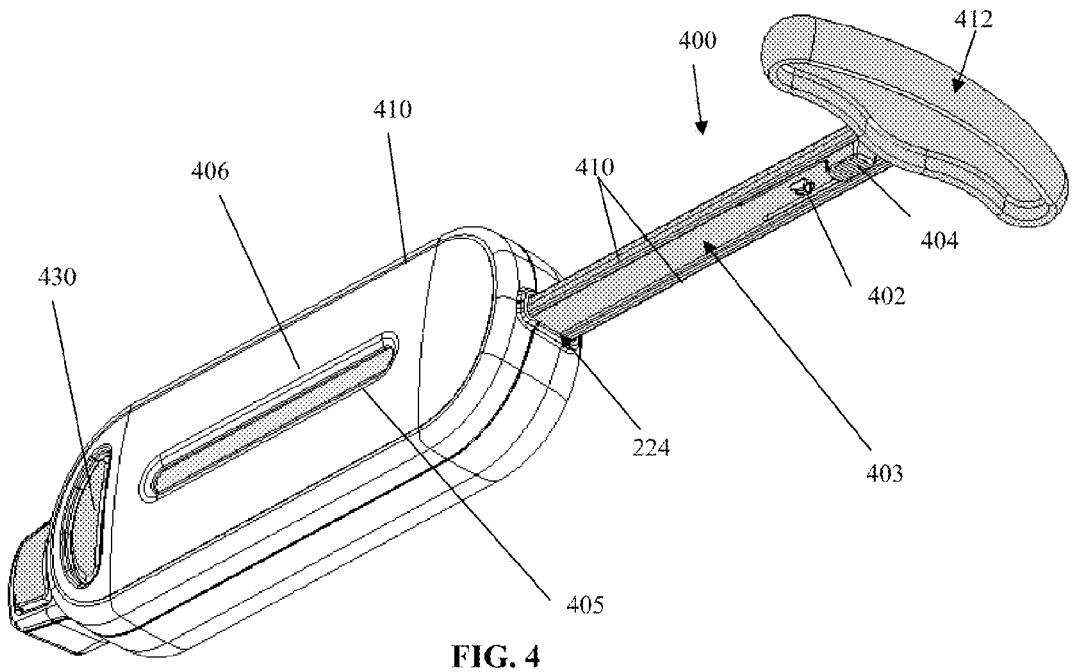
FIG. 4 is a perspective view of the embodiment of FIGS. 2 and 3 with a priming tool.

As depicted in FIG. 4, some embodiments of the tissue therapy system may comprise a priming tool or rod 400 which may be inserted into the suction apparatus 101. The rod 400 may be pushed through an opening 224 of the housing 220 to push the sliding seal towards the distal end 208 of the suction chamber 202 and to charge the constant force springs with potential energy. In some embodiments, the suction apparatus 101 may be configured so that the priming tool 400 contacts or engages the seal mount (210 in FIG. 2) at or adjacent to where the constant force springs 212 are coupled to the seal mount 210. In other embodiments, the suction apparatus 101 may be configured such that the priming tool 400 directly pushes against the springs 212, in addition to or in lieu of pushing against the seal mount 210. In some embodiments, once the sliding seal is moved to the primed configuration, a locking structure or latch 402 located on the shaft 403 of the priming tool 400 may engage a complementary structure (e.g. slot 219 in FIG. 3) of the housing 220. Thus, the priming tool 400 may be used to lock the seal into its primed configuration and resist the constant force springs from retracting and losing its potential energy. The priming tool 400 may also comprise a handle 412 to facilitate gripping and use of the tool 400.

In other examples, the priming mechanism may be used without removing the priming tool from the device. In these embodiments, as the seal retracts, the priming tool will extend out of the accessing opening of the housing. In still other examples, a priming mechanism other than a linear push-based mechanism may be used, including but not limited to one or more rotatable knobs that may be used to unwind and extend the substantially constant force springs or other bias members to prime the device. In some other examples, where the force required to overcome the springs and prime the device may be excessive, the priming tool may be threaded and the priming tool opening may be configured with a screw drive coupled to a handle that may provide a mechanical advantage to a user priming the device. In still other examples, embodiments comprising a rotatable knob may comprise a slide-out handle, a swing out handle or an attachable handle to provide the user with greater torque when winding the knob.

Referring back to FIGS. 2 and 3, the access opening 224 may be configured to restrict or limit pivoting or angulation of the priming tool 400 during insertion. The housing 220 may also comprise guides 222 that may further restrict or limit the motion of the priming tool 400 during insertion. The priming tool 400 may also comprise guide structures. FIG. 4, for example, depicts the priming tool 400 with ridges or raised edges 410 which may facilitate tracking of the shaft 403 along the constant force springs 212 as the springs 212 are extended. The distal end of the priming tool 400 and/or the seal mount 210 may be configured with complementary interfaces to resist decoupling as force is being applied using the priming tool 400.

In some embodiments, the priming procedure described above may be performed when the suction apparatus disconnected from any other components, e.g., extension tubing, attachment port or sealant layer. After priming the suction apparatus, the suction apparatus is attached to a sealant layer, directly or through extension tubing, the priming tool is removed, and the activation button on the suction apparatus is pressed to apply a reduced pressure within the sealed wound enclosure created by the sealant layer. In other embodiments, this priming process is completed with the activation button in the "off" position. Such design may prevent elevated pressure from being applied onto the damaged tissue inadvertently. A one-way valve in communication with the collection chamber may also be provided to expel air from the collection chamber during the priming procedure. Referring still to FIGS. 3 and 4, in some embodiments, once the suction apparatus 101 is primed, a latch tab 404 or other actuator on the shaft 403 of the priming tool 400 can be pressed or manipulated to disengage the latch 402 from the interlocking slot 215, thereby allowing the priming tool 400 to be withdrawn from the suction apparatus 101. In some embodiments, the priming tool 400 may be left in the suction apparatus to ensure safe storage of the suction apparatus since it prevents the constant force springs from retracting due to micro-leaks. In some examples, the priming procedure may be performed at the point-of-manufacture, while in other examples, the suction apparatus may be provided in an unprimed state and primed at the point-of-use.

In some embodiments, the seal mount 210 may further comprise stabilizers 211 which prevent or resist excessive angular displacement of the sliding seal 207 with respect to the primary axis of the suction apparatus 101. The stabilizers 211 may comprise longitudinal extensions or projections from the seal mount 210. The stabilizers 211 may or may not have an orientation that is generally parallel to the longitudinal movement axis of the seal 207. Also, a stabilizer 211 may be configured to be in sliding contact with the wall of the suction chamber 202 along its entire length, or may be configured to only partially contact the wall of the suction chamber 202. For example, a portion of the stabilizer may curve or angle away from wall of the suction chamber. In some embodiments, the interior of the suction apparatus 101 further comprises a friction-reducing lubricant or a lubricous coating. In other examples, the seal and/or seal mount may have a variable thickness along its perimeter or contact with the wall of the suction chamber. In some instances, an increased thickness may increase the stability of the seal along a dimension of the seal. In some examples, the portion of the seal and/or seal mount with the increased thickness may vary depending upon the transverse dimension intersecting a) the portion of the perimeter and b) the central movement axis of the seal and/or seal mount. Other examples of seals and/or seal mounts with a variable thickness are provided in greater detail below.

Figure 5:
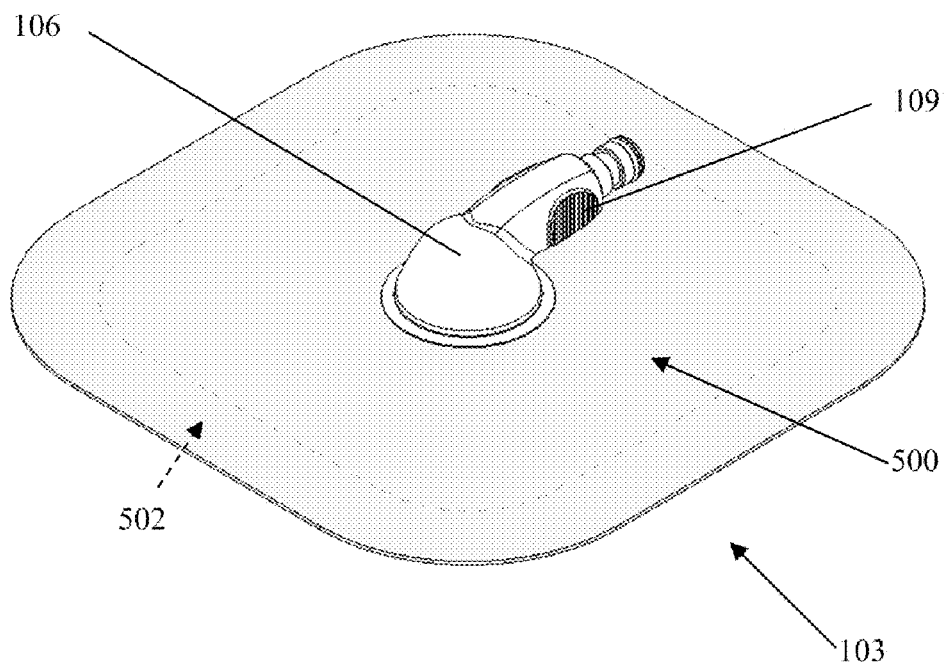
FIG. 5 is a perspective view of a sealant layer with an attachment port.

FIG. 5 depicts the sealant layer 103 of FIG. 1 without an attached extension tube. The main body 500 of the sealant layer 103 may comprise a substantially flat, flexible material which is configured to form an airtight seal over a portion of tissue to be treated by adhering to the skin circumferentially to the damaged tissue section or wound. In some embodiments, the bottom surface of sealant layer 103 comprises a pressure sensitive adhesive (PSA) layer 502, including but not limited to any of a variety of silicone PSAs. The main body 500 of the sealant layer 103 may comprise an average thickness between 0.001 and 0.5 inches thick and may or may not be of sufficient thickness to resist wrinkling or inadvertent folding onto itself. As mentioned previously, the attachment port 106 may be configured to swivel about the axis normal to the plane which approximates the surface of sealant layer 103. In some embodiments, the swivel range may be limited, but in other embodiments, the attachment port 106 is able to swivel 360 degrees or more. In some embodiments, attachment port 106 further comprises gripping surfaces which facilitate connection and disconnection of attachment port 106 to appropriate fittings.

Figure 6:
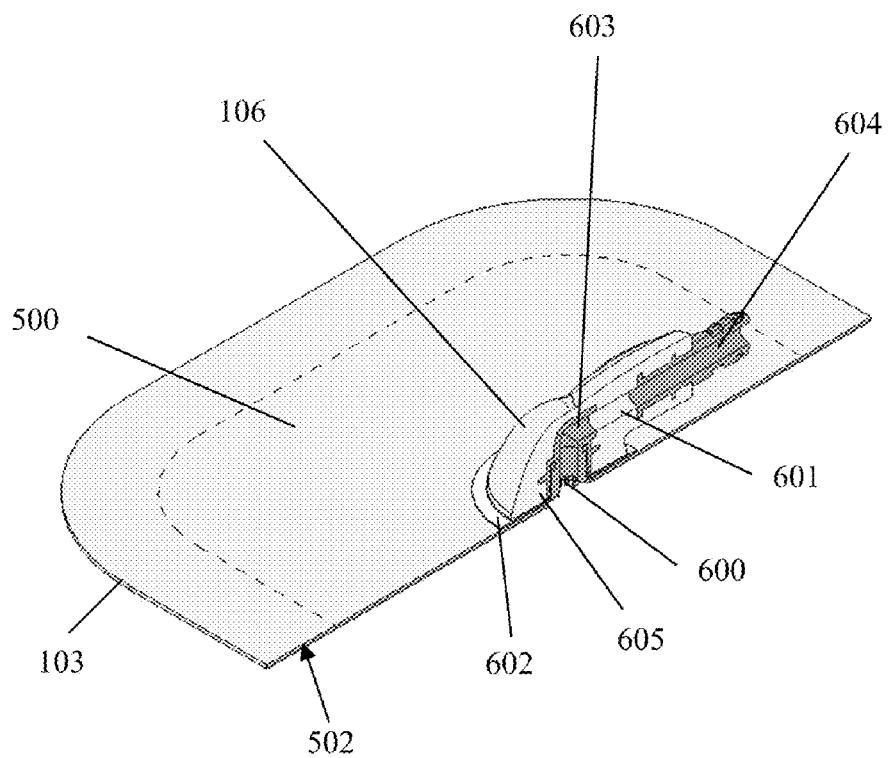
FIG. 6 is a cross-sectional perspective view of the sealant layer and the attachment port of FIG. 5.

FIG. 6 depicts a cross sectional view of the sealant layer 103. In this embodiment, attachment port 106 further comprises a fenestration or opening 600 in the main body 500 of sealant layer 103 which is in fluid communication with a conduit 601 in the attachment port 106. In some embodiments, the sealant layer 103 further comprises a fixed swivel fitting base 602 which is adhered or attached to the main body 500 of the sealant layer 103. The attachment port 106 further comprises swivel fitting collar 603 which is mated to swivel fitting base 602 in an airtight manner and allows attachment port 106 to rotate about swivel fitting base 602. The attachment port 106 may further comprise a connector 604 to facilitate airtight connection to other components, such as the extension tubing or the suction apparatus. In some embodiments, the connector 604 and/or the swivel fitting collar 603 of the attachment port 106 may be coupled to in flexible elastomeric body 605. The conduit 601 passes through swivel fitting collar 603, a hollow section of the elastomeric body 605 and the connector 604. In some embodiments, the swivel fitting collar 603 and connector 604 may comprise a rigid material but the flexible elastomeric body 605 permits relative movement between the collar 603 and the connector 604. In some examples, the flexible body 605 may be configured to permit some bending while resisting pinching comprise one or more conduit support structures to resist pinching of the flexible body that may result in blockage of conduit 601.

In some embodiments, the device may be used for the treatment of lower extremity wounds. The suction apparatus may be configured with a low profile with respect to its placement against the skin or body of a patient, e.g. the suction apparatus has a first outer dimension that is smaller than that is perpendicular to the surface that facilitates its placement on the leg or thigh underneath a normal pant leg, that low profile is achieved through non circular suction chamber design which lowers the apparatus' profile while enabling the suction chamber to handle large amounts of exudates. In some embodiments of the device it comprises an attachment mechanism configured to attach the device to the user's limb or torso, or to a belt or other article of clothing. In some embodiments of the device the attachment mechanism is a fabric leg strip with adjustable self gripping fasteners. The fabric leg strip can be constructed from cotton or foam or any other material known to those skilled in the art. In other embodiments of the device the attachment mechanism is a flexible pocket adapted to contain the suction apparatus and attach to the body.

Figure 7:
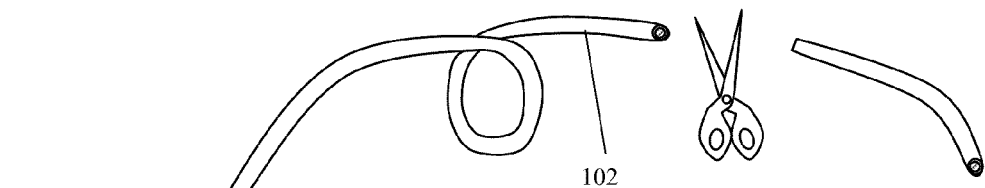
FIG. 7 is a perspective view of an extension tube connected to the sealant layer and attachment port of FIG. 5.
Figure 8A:
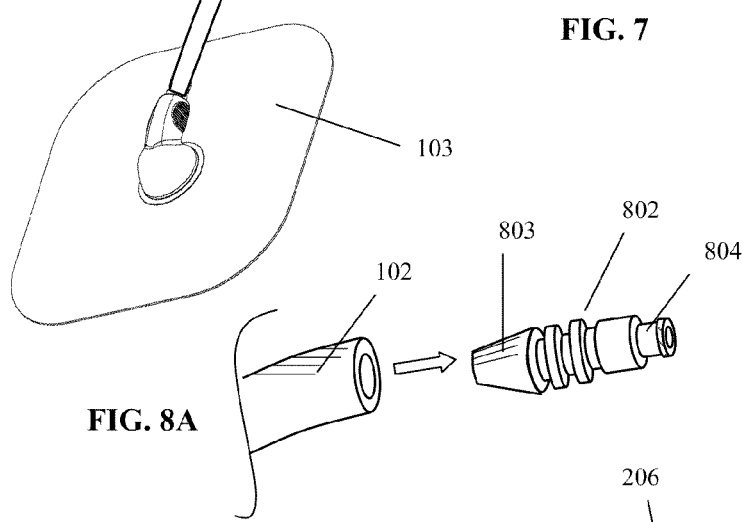
FIGS. 8A to 8C depict an exemplary method for connecting an extension tube to a suction apparatus.
Figure 8B:
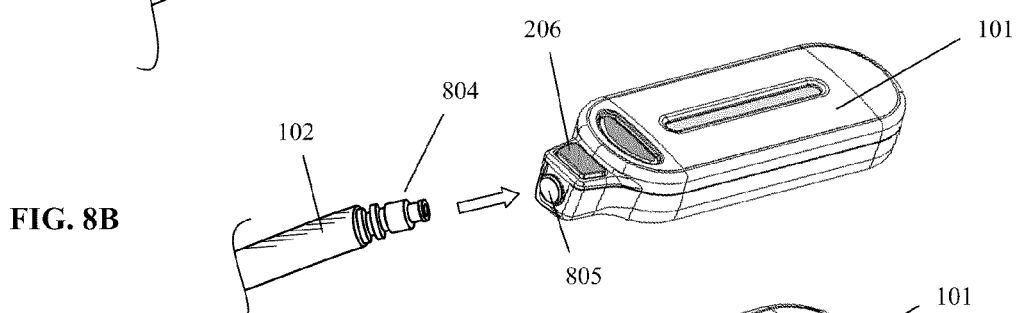
Figure 8C:
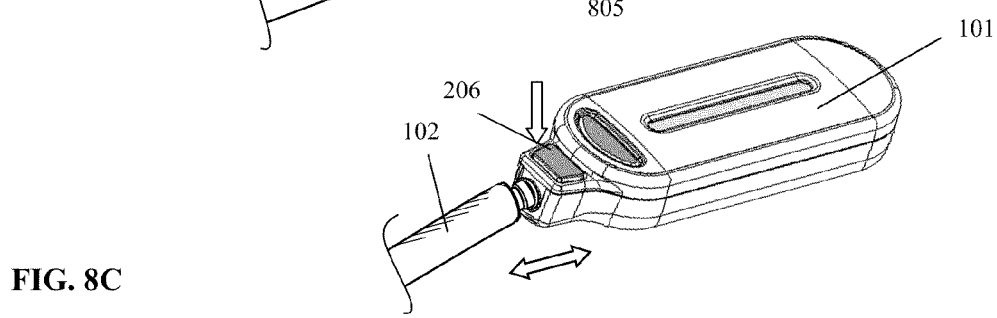

As mentioned previously, the reduced pressure therapy device may be used with an extension tube, and in some examples, the extension tube may be custom sized. The desired length of the extension tube 102 may be determined either by assessing the distance to the suction apparatus placement location using the extension tube. As illustrated in FIG. 7, an extension tube 102 may be first attached to a sealant layer 103 before cutting, but in other examples, the extension tube 102 may be attached or unattached to the sealant layer and/or suction apparatus when cut. Also, the sealant layer and suction apparatus may or may not be applied to the treatment site or placement location when assessing the extension tube length. Once the desired length of the extension tube is determined, the extension tube 102 may be cut to remove a proximal tubing segment. As shown in FIGS. 8A to 8C, the extension tube 102 may be connected to the suction apparatus 101 using a connector 802. A first end 803 of the connector 802 may be configured for coupling or insertion into a bare end of the extension tube, and in some examples, may comprise one or more tapered structures 810, flanges 812 and/or barbs to facilitate coupling and/or to resist decoupling. A second end 804 of the connector 802 may be configured to connect to the complementary connector 805 of the suction apparatus 101. In other embodiments, a connector is not required and the bare end or cut end of the extension tube may be directly coupled to the suction apparatus 101. In still other examples, both ends of the extension tube may be pre-attached with connectors and a middle section of the extension tube may be cut out and the two remaining sections can be joined together using a connector where both ends are configured to attach to bare tubing.

Although the reduced pressure therapy device depicted in FIGS. 1 to 4 comprises a suction apparatus 101 with separate "activation" and "release" actuators, in other embodiments, a single actuator with an "activation" and a "release" position may be provided. In still other embodiments, no actuators may be provided. In some of the latter embodiments, the suction apparatus may begin to generate reduced pressure once the force from the priming tool is no longer applied. In other examples, the suction apparatus may be configured with activation and/or release mechanisms that may open or close a valve from the coupling or decoupling of the extension tube. For example, the suction apparatus may comprise a slit valve which opens when the extension tube or a connector is inserted into it.

FIGS. 9A to 9D illustrate another embodiment of a reduced pressure therapy device 900 with a priming tool 902. FIGS. 9A and 9B depict the priming tool 902 engaged in two positions: a primed position and an activated position, respectively. To initially prime the reduced pressure therapy device 900, a user may insert and push the priming tool 902 into an opening 905 in the body 906 of the device 900. As the priming tool 900 contacts the seal mount of the sliding seal, the sliding seal is displaced towards the distal end 908 of the device 900, which extends the constant force springs attached to the seal mount and thus impart potential energy into the springs. In some examples, the opening 905 and/or the body 906 of the device 900 is configured to facilitate the contact or engagement of the tool 902 to the seal or seal mount. For example, the opening 908 may be configured with a complementary cross-sectional shape to the shaft 910 of the tool 902, and/or the body 906 of the device 900 may be configured with a passageway in communication with the opening 905, such that translational or angular displacement of the tool 902 is reduced. In some examples, the tool may also be configured to track along the edges and/or surfaces of the internal springs to facilitate contact or engagement to the seal or seal mount. For example, the shaft 910 of the tool 902 may be configured with one or more projecting edges 914. The edges 914 may be configured to track along the edge(s) of the internal springs. The distal end of the tool 902 may be configured with a structure complementary to a structure on the seal or seal mount which may reduce the risk of decoupling between the tool 902 as force is exerted by the user and/or by the springs.

In FIG. 9A, the priming tool 902 has pushed the sliding seal (not shown) from the proximal end 905 towards the distal end 908 of the device 900. The device 900 and the priming tool 902 may also be configured to releasably lock the tool 902 and/or the sliding seal in its primed position. In some examples, a device 900 with a locking mechanism permits priming without requiring that the device 900 be attached to the sealant layer, or that the operator continue to exert force using the tool 902 until it is ready for activation. Any of a variety of locking structures or locking mechanisms may be provided, including but not limited to interlocking fits or resistance fits between the device 900 and the tool 902. For example, the handle 912 of the tool 902 may be configured with a locking flange (not shown) that may engage the opening 905 of the device 900 to resist displacement of the tool 902 away or out of the body 906. Upon rotation, the flange may be disengaged to permit passage of the flange out of the opening 905, along with the shaft 910 of the tool 902. In the particular embodiment depicted in FIG. 9B, the priming tool 902 may be configured so it may be rotated between a locked and an unlocked configuration, but in other examples, a movable latch, locking pin or other interfering mechanism may be used instead of a locking flange. As shown in FIGS. 9B and 9C, once in the unlocked position, the tool 902 may be removed to permit activation of the device 900, or the force of the springs or bias mechanisms may push the tool 902 out of the device 900 without requiring the user to pull the tool 902.

In some embodiments, the reduced pressure therapy device may be configured to permit repriming of the device by re-actuating the tool. In other embodiments, the tool may be configured to permit limited repriming of the device, or no repriming of the device. As depicted in FIGS. 9C and 9D, for example, the tool 902 may be configured with one or more projections 916 on the shaft 910. When the device 900 is activated, the internal springs may begin to bias the seal back to a proximal position. In some instances, where a large volume of air exists under the sealant layer, or the device 900 is improperly connected to the sealant layer, and/or the sealant layer is improperly applied to a treatment site, air may be immediately drawn into the device 900, such that the tool 902 quickly extends back out of the opening 905. The projections 916 may be configured to resist further retraction of the seal by the spring, while also remaining partially inserted into the opening 905. In some instances, this may be used by the user as an indicator to recheck the connections or sealant layer seal. After correcting or addressing the cause of an air leak, if any, the user may push the tool 902 back into the body to re-prime the seal and then to regenerate the reduced pressure. In some examples, re-priming of the device using the tool may be repeated until the desired sealant layer seal is achieved. Once achieved, the tool 902 may be separated from the body 906 of the device by exerting a pulling and/or twisting force to deform the projections 916 to allow removal of the tool 902. The increased force required to remove the tool 902 may reduce the risk of inadvertent removal of the tool 902. Once removed, the projections 916 may resist reinsertion of the tool 902 back into the device 900. In some examples, limiting re-use of the device may reduce the risk of contamination that may be associated with aspiration of wound material into the device.

In some embodiments, the suction apparatus may comprise a separate or separatable collection chamber which may be coupled or contained within a housing. The housing may be configured to interface with the collection chamber and self-generate a reduced pressure level within the collection chamber. In some embodiments, the housing further comprises at least one force member that is configured to couple to the seal or seal mount located in the collection chamber. In some embodiments, a priming tool may be used to facilitate the coupling of the collection chamber and the housing and/or to prime the seal. In some embodiments, the collection chamber of the suction apparatus may be separated from the housing, disposed and a new collection chamber may be coupled to the housing. In other embodiments, the collection chamber may be separated from the housing, emptied and/or cleaned, and then re-coupled with the housing. During long-term use of the reduced pressure therapy device, the housing may also be replaced due to wear and tear of the housing or the force member(s).

Figure 10A:
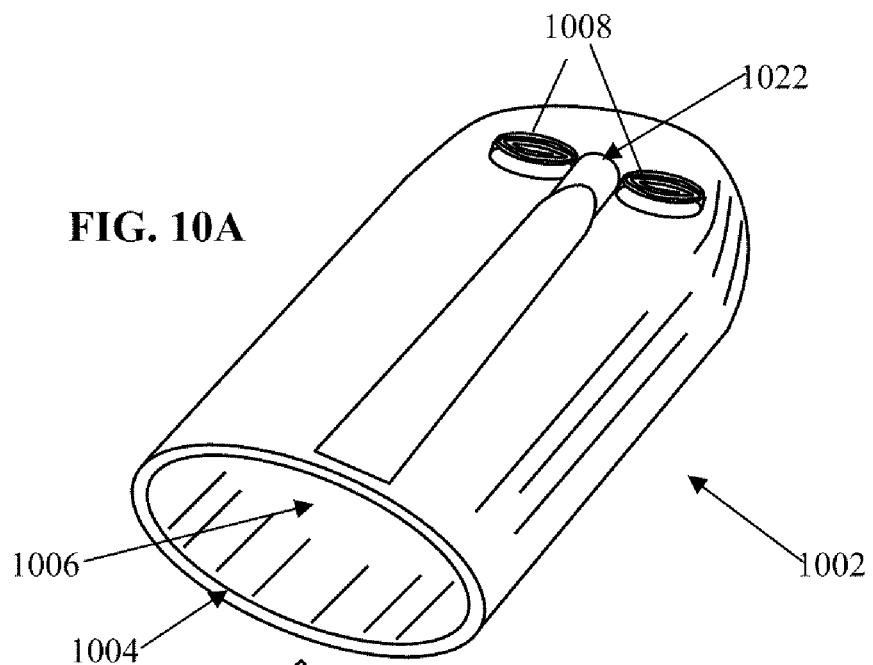
FIGS. 10A and 10B are schematic component views of another embodiment of a reduced pressure therapy device, comprising a housing chamber and a collection chamber, respectively.
Figure 10B:
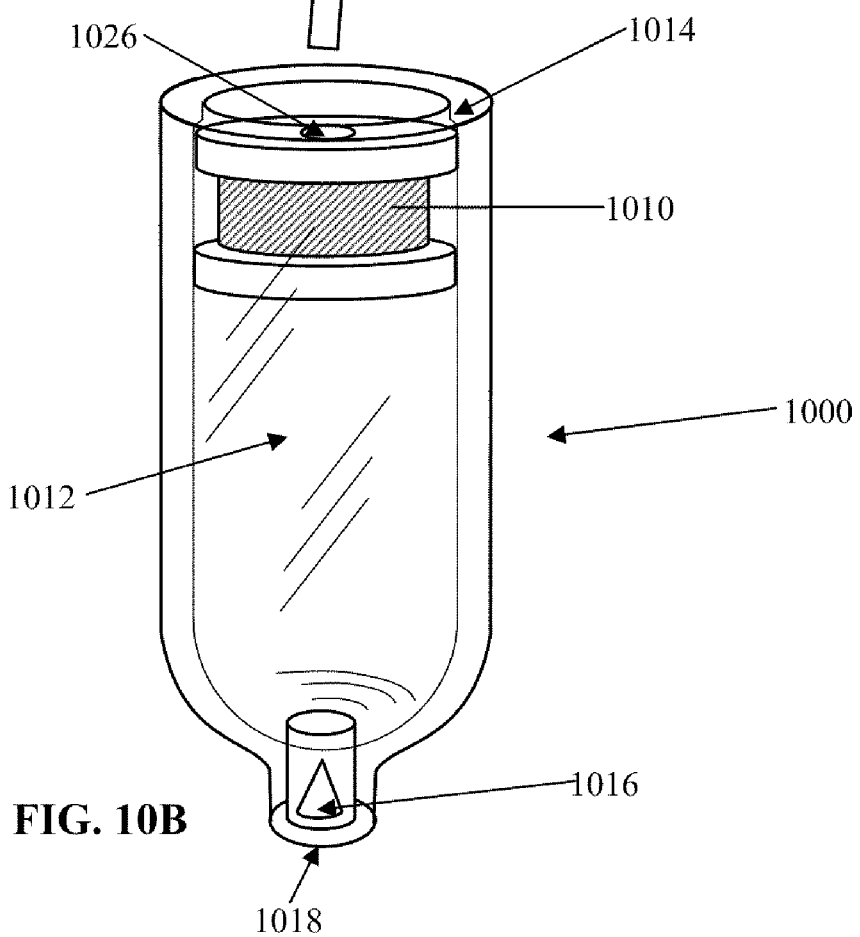

FIGS. 10A and 10B illustrate one another embodiment of a reduced pressure therapy device, comprising a housing 1002 and a collection chamber 1000. The housing 1002 may comprising a housing opening 1004, a housing cavity 1006, and at least one force member, e.g., a pair of constant force springs 1008, located in the housing cavity 1006, which may be configured to coupled to a seal 1010 located in a slidable arrangement in the collection cavity 1012 of the collection chamber 1000. The springs 1008 may access the seal 1010 through a proximal opening 1014 of the chamber 1000. The seal 1008 may comprise a seal interface 1026 that is configured to accept either the distal end(s) of the spring(s), and/or the distal end of a priming tool. The collection cavity 1012 may comprise a flange or lip 1014 to resist separation of the seal 1010 from the cavity 1012. In some variations, a one-way valve 1016 may be provided about the inlet 1018 of the collection cavity 1010. In some embodiments, the springs may be configured to attach to the seal as the collection chamber is inserted into the housing. For example, the distal ends of the springs may be configured to form a threaded fit with the seal by rotating the housing with respect to the collection chamber. In other embodiments, the distal ends of the spring may be coupled to the seal using the priming tool, in addition to the use of the priming tool to prime the suction apparatus.

Figure 10C:
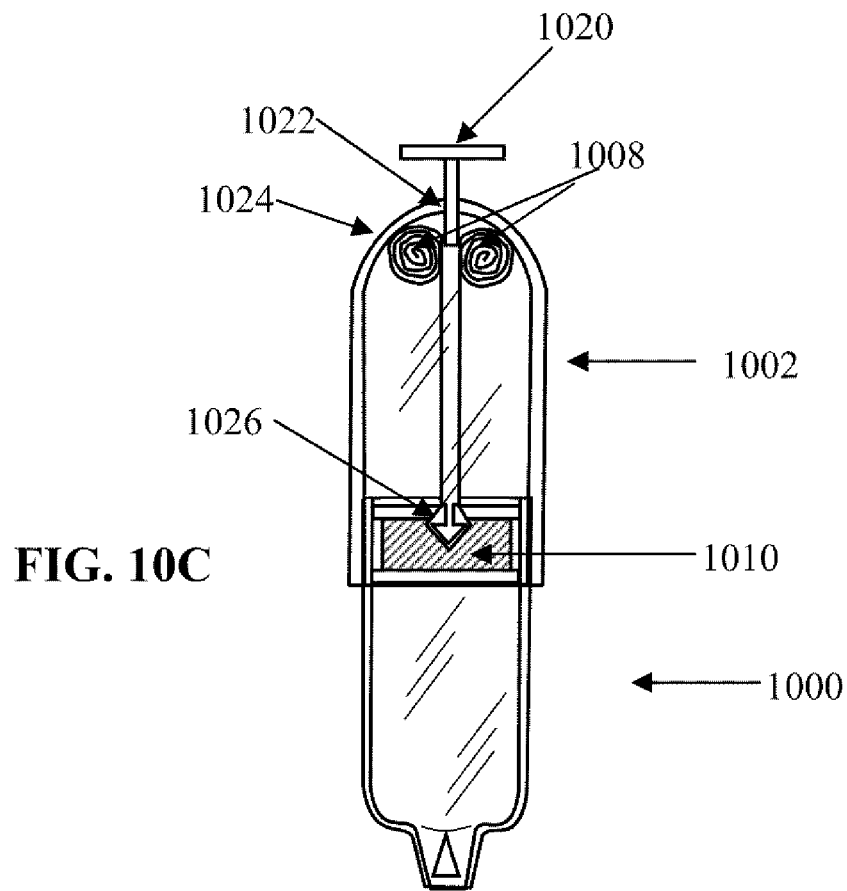
FIGS. 10C and 10D, illustrate the reduced pressure therapy device of FIGS. 10A and 10B in non-primed and primed configurations, respectively.
Figure 10D:
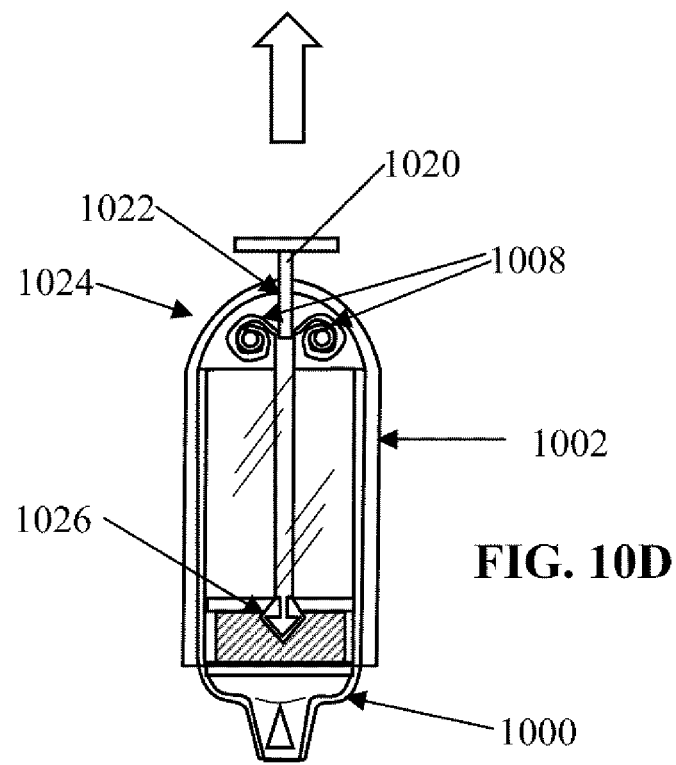

FIGS. 10C to 10D illustrate one example using the housing 1002 and collection chamber 1000 of FIGS. 10A and 10B. A priming tool 1020 is inserted into the housing 1002 through an opening 1022 at the proximal end 1024 of the housing 1002. The tool 1020 may be used to push or extend the spring(s) 1008 or other bias member(s) located in the housing 1002 into an extended configuration. The collection chamber 1000 and the housing 1002 are then coupled together to engage the springs 1008 to the seal interface 1026 of seal 1010 while the springs 1008 are in the extended configuration. The engagement may be achieved by an interlocking interfit or other type of complementary interfit. With the tool 1020 still in place, the collection chamber 1000 is then further pushed into the housing 1002, which pushes the seal 1010 into a distal position in the collection cavity 1008, as illustrated in FIG. 10D. The springs 1008 and the seal 1010 are then primed and may be activated by removal of the priming tool 1020.

Once the collection chamber 1000 is filled with exudates from the damaged tissue and/or the potential energy in the springs 1008 is exhausted, the collection chamber 1000 may then be separated from the housing 1002 by decoupling the springs 1008 from the seal 1010. In some examples, the airtight separation provided by the seal 1010 protects the housing 1002 from contamination and permits reuse of the housing 1002 with a new collection chamber. In other examples, the housing 1002 and/or the collection chamber 1000 may be reused, regardless of the sterility or contamination state.

In some embodiments the reduced pressure therapy device comprises a plurality of suction and/or collection chambers. In one embodiment, the multiple chambers may be disposed side by side, or end-to-end, or a combination thereof. In some embodiments, a suction chamber may also serve as a collection chamber. The chambers may have an elongate configuration and any of a variety of axial cross-sectional shape, including but not limited to circular shapes. The plurality of chambers may be arranged such that the average perpendicular dimension (e.g. thickness) of the device with respect to the body surface of the patient where the device is worn is smaller than either of the other orthogonal dimensions of the device (e.g. width, length or diameter). The plurality of chambers may be rigidly or flexibly coupled to each other. In some embodiments, the multiple chambers may be configured to form a generally concave surface, which may conform to a surface of the body site to which the device will be attached. In some embodiments, the concave surface substantially conforms to an arc with a radius that is between about 1 cm and about 1000 cm, sometimes between about 5 cm and about 800 cm, sometimes between 10 cm and about 500 cm, and sometimes between about 50 cm and about 250 cm. The radius of such concave surface may be selected in part on the local topology of the body site to which the tissue therapy will be attached. A multi-chamber reduced pressure therapy device may be used to provide a low-profile device while also providing a large reduced pressure chamber volume and/or exudate handling capacity.

FIGS. 11A and 11B illustrate one example of the reduced pressure therapy device 1100 comprising multiple chambers 1102, 1104 and 1106. Although the depicted example comprises three chambers 1102, 1104 and 1106, in other examples, a fewer or a greater number of chambers may be provided. The chambers may or may not have the same size or shape or feature set. For example, suction chamber 1104 may comprise a viewing window 1108 and an actuating knob 1110 which is configured to actuate reduced pressure generation in all three chambers 1102, 1104 and 1106. In some examples, two or more chambers, or all of the chambers may be configured to be independently actuatable and/or configured identically. The number of chambers may be in the range of about two chambers to about ten chambers or more, but other examples may be in the range of about three chambers to about six chambers. As illustrated in FIG. 11B, the suction chambers 1102, 1104 and 1106 may be arranged to have a generally concave configuration along at least one dimension or surface of the device 1100, but in the same or a different embodiment, at least one dimension or surface may have a generally planar configuration or a convex configuration. Alternatively, the device may have a variable configuration where at least the chambers 1102, 1104 and 1106 are flexibly connected or articulated. As depicted in FIG. 11B, the interconnecting structures 1112 and 1114 of the device 1100 may be sized and shaped to provide at least one generally smooth surface 1116, which may be the surface of the device 1100 configured to be placed against the body site of a patient. In other examples, the upper surface 1118 of the device 1100 may or may not also be smooth. The example depicted in FIGS. 11A and 11B may further comprise at least one attachment structure or mechanism, such as a strap or belt loop 1120 to facilitate wearing of the device with a strap or band 1121, for example, as shown in FIG. 11F. In other examples, the device may comprise a different attachment structure such as a hook, or one or more straps or belts may be integrally formed with the device. The strap or belt may be similar to belts used with a variety of clothing, but may also be configured for attaching the device to a patient's limb or the patient's abdomen or torso. In the example shown in FIGS. 11A to 11F, the loop 1120 has a width that is less than the corresponding dimension of the chambers 1102, 1104 and 1106 and is configured to accept straps or belts of similar width or less, but in other examples, the loop width may be larger than the corresponding chamber dimensions and/or may be open loops. In some further examples, the loops or other attachment mechanism may be articulated or reconfigurable so that the relative orientation of the chambers 1102, 1104 and 1106 to the loops or attachment mechanism may be changed, e.g. rotated. The strap or belt may comprise an attachment mechanism, such as a clip, buckle or hook and loop structures, and may be elastic or inelastic. The width of strap or belt may be in the range of about 1 cm to about 40 cm or more, in some examples about 2 cm to about 30 cm, or in other examples about 5 cm to about 20 cm. The loops may comprise a rigid or a flexible material, and may have a fixed or an articulated attachment to the device.

In some embodiments that comprise multiple chambers, two or more chambers may function independently, or may be in fluid communication with each other in a parallel or serial arrangement. FIGS. 11C and 11D illustrate two embodiments of a reduced pressure therapy system 1150 and 1160 wherein each chamber 1102, 1104 and 1106 has it own inlet 1122, 1124 and 1126, respectively. In FIG. 11C, each inlet 1122, 1124 and 1126 of the system 1150 may be attached to a separate connector tube 1128, 1130 and 1132, which are each connectable to a separate attachment ports 1134, 1136 and 1138 of the sealant layer 1140. In some examples, a sealant layer 1140 with multiple attachment ports or sites may be useful for treating septated or multi-cavity wounds, or treatment sites with multiple tracts. In FIG. 11D, a branching extension tube 1142 maybe a reduced pressure therapy device 1160 and a sealant layer 1144 where the device 1150 has a different number of inlets than the number of attachment ports on the sealant layer. FIG. 11D depicts an example of the three inlets 1120, 1122 and 1124 of the device 1160 are connected using a branching extension tube 1142 to a single attachment port 1146 of a sealant layer 1144. In other examples, only the reduced pressure therapy device may have a fewer number of inlets as than the number of attachment ports on the sealant layer. In still other examples, the multiple suction chambers need not be used simultaneously. As illustrated in FIG. 11E, the suction chambers 1102, 1104 and 1106 of the system 1170 may be used sequentially, where the connector tube 1128 is detached from an expended chamber and reattached to different chamber. Protective removable caps 1146 and 1148 may be used with the inlets 1120 and 1124 of chambers 1102 and 1106 not currently connected to a connector tube. In other embodiments, the device may comprise a multi-port valve which may be used to change the communication between an inlet and a suction chamber, so that separate inlets for each chamber are not required.

Figure 12:
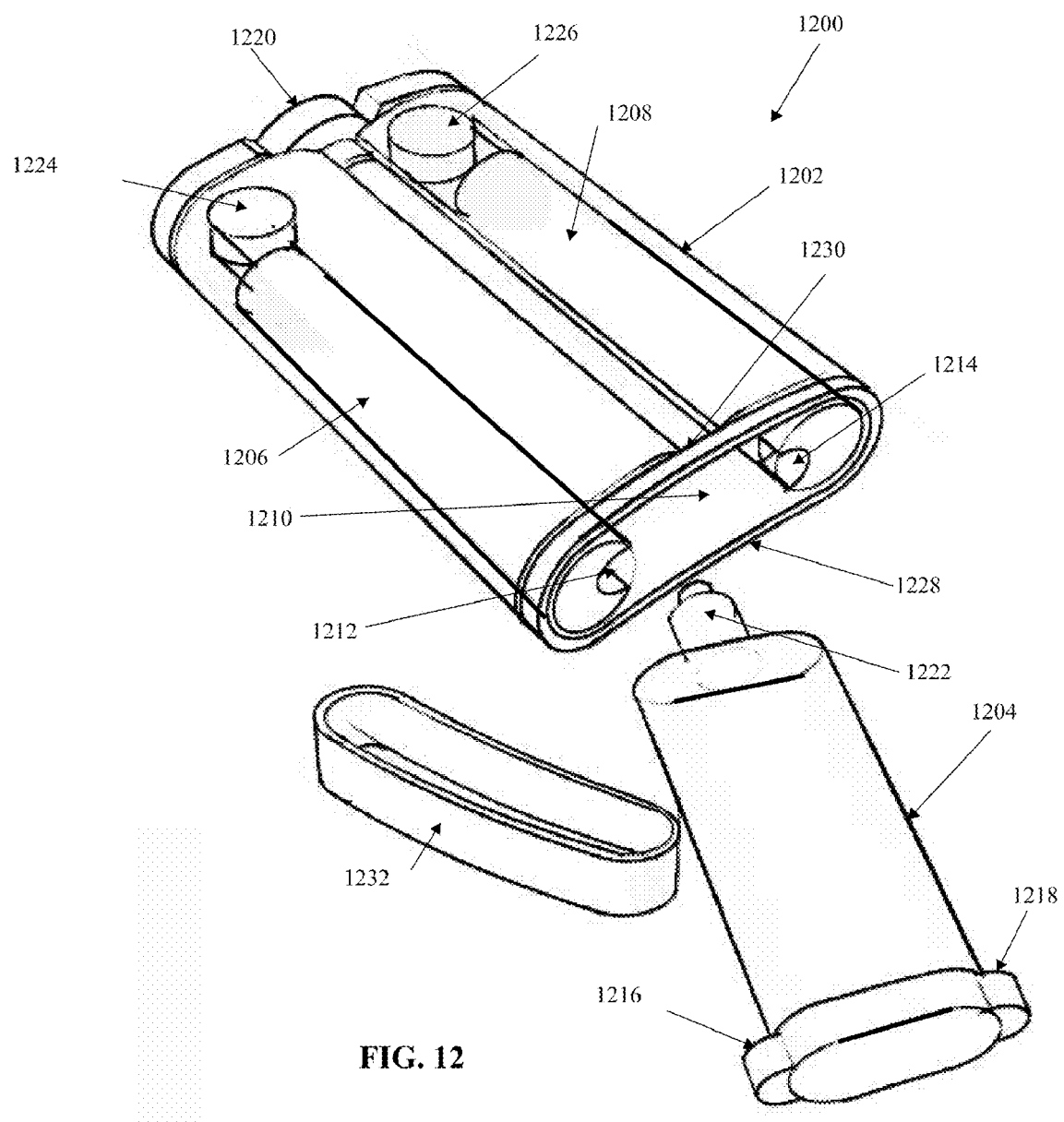
FIG. 12 is a component view of another embodiment of a reduced pressure therapy device, comprising a collection chamber and a housing.

As mentioned previously, a reduced pressure therapy device comprising a plurality of chambers may have chambers with different features and/or functions, including devices with both suction chambers and collection chambers. As depicted in FIG. 12, in some embodiments, the reduced pressure therapy device 1200 may comprise a housing 1202 and a collection chamber 1204. The housing 1202 may comprise one or more suction chambers 1206 and 1208. In this particular example, the housing 1200 comprises two suction chambers 1206 and 1208 which are located to each side of the housing 1202 and with a collection cavity 1210 between the suction chamber 1204 and 1206 configured to receive the collection chamber 1204. The collection cavity 1210 may also be configured to align any openings 1212 and 1214 or channels of the collection chamber 1202 with corresponding openings 1216 and 1218 or channels of the suction chambers 1204 and 1206. In this particular embodiment, the housing 1202 comprises a housing inlet 1220 which may be in fluid communication with a collection inlet 1222 of the collection chamber 1202 when the collection chamber 1202 is inserted into the housing 1200. Each suction chamber 1206 and 1208 may comprise one or more force members, e.g. constant force springs 1224 and 1226 coupled to a movable seal (not shown). In use, the collection chamber 1204 is in fluid communication with the sealed wound enclosure and may be replaced or emptied when it is filled up by exudates from the damaged tissue or when the potential energy of the force members is depleted. The device 1200 may also comprise at least one smooth concave surface 1228 that is designed to conform to the contours of the body site to which the device is secured. The opposing surface 1230 of the device 1200 may or may not have a convex surface, as depicted in FIG. 12. The device 1200 may also comprise a cap or cover 1232, which may be useful to protect dirt entry into the housing 1200, and/or to secure the collection cavity 1202 to the housing 1200. The cover 1222 and housing 1202 may or may not be configured to form an airtight seal. In other examples, the collection chamber 1204 may be configured with an integrated cap or cover. The collection chamber 1204 may be configured to be secured to the housing 1200 by a resistance interfit or a mechanical interlock, for example. In use, because the collection chamber 1202 does not contain the priming and activating mechanism, e.g., constant force springs and a priming tool, the device 1200 may be easier to replace and/or clean. Once the collection chamber 1202 is filled up with exudates, the user can replace the filled collection chamber 1220 by inserting a new chamber into the housing chamber 1210 and repeating the priming and activating steps as described elsewhere. In use, the device 1200 may be oriented so that the housing inlet 1220 is located inferiorly relative to the rest of the device 1200. In this orientation, any exudate aspirated into the collection chamber is less likely to reach the openings 1216 and 1218 of the collection chamber 1204 and fill the suction chambers 1206 and 1208 with exudate. In some examples, filter structures may be provided in the suction chambers 1206 and 1208 and/or the collection chamber 1204 to resist or block entry of non-gaseous material into the suction chambers 1206 and 1208.

Figure 13A:
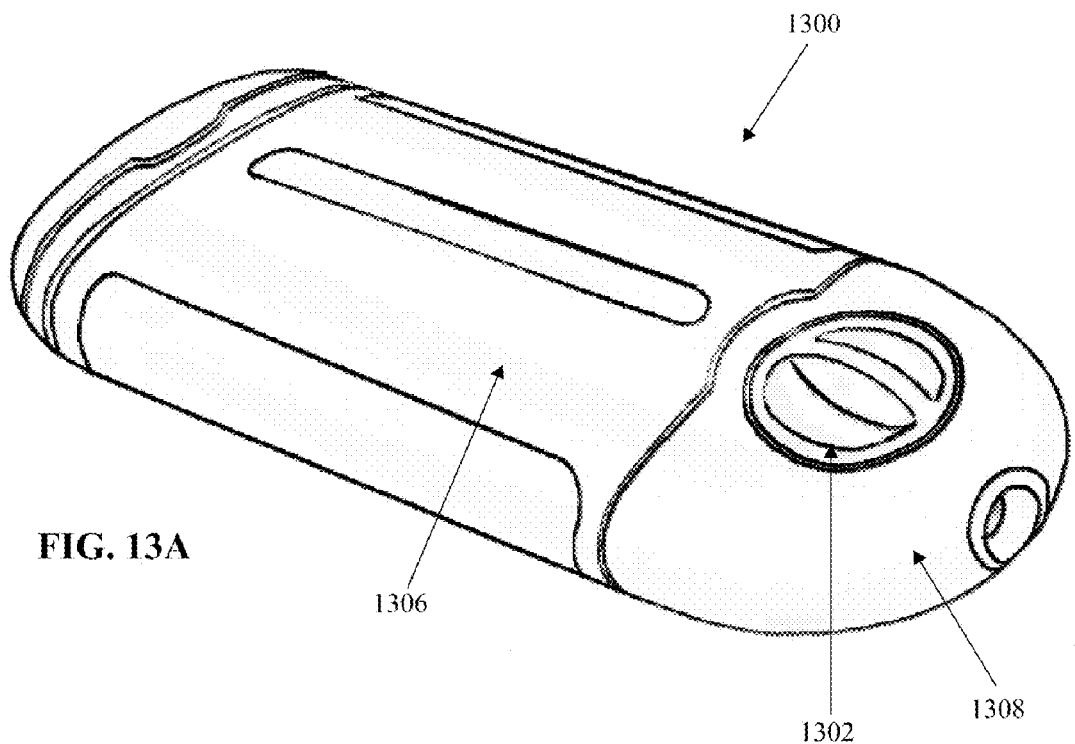
FIG. 13A is a perspective view of another embodiment of a reduced pressure therapy device with a rotary activation interface.
Figure 13B:
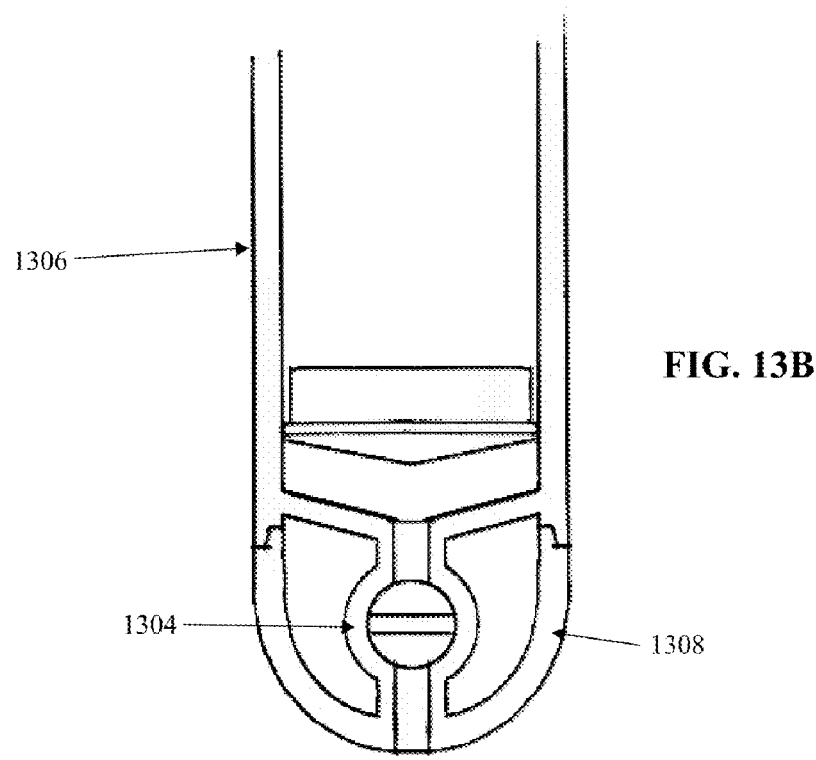
FIG. 13B is a cross-sectional superior view of the device in FIG. 13A.

In some embodiments, the reduce pressure therapy device 1300 may comprise a multi-position actuator, such as a slider or rotary control knob 1302, as illustrated in FIGS. 13A and 13B. In some embodiments, the rotary knob 1302 may be coupled to a valve 1304 which may be configured with at least two positions: an "open" position and a "closed" position. The device 1300 may be primed by changing the knob 1302 to the "open" position which permits fluid communication through the control valve 1304 to expel any air out of the collection chamber 1306 during priming. When the knob 1302 is placed at a "closed" position, the fluid communication is blocked to resist inflow of air or other materials into the collection chamber 1306. The device 1300 may then be attached to a sealant layer and the activated by turning the knob 1302 to permit transmission of the reduced pressure in the collection chamber 1306. In some examples, a low-profile knob may reduce the risk or avoid an inadvertent activation and/or release of the device compared to devices comprising push buttons. As mentioned elsewhere, the knob and its associated mechanism may also be configured with additional positions or states. For example, the knob may also have a separate priming position which permits the air or gas in the chamber 1304 of the device 1300 to be expelled during the priming procedure without causing pressure buildup. In other examples, however, a continuous one-way valve may be provided to vent any pressure buildup in the collection chamber. In some other examples, the knob and/or the valve mechanism may be configured to be single-use, which may reduce the risk of re-using a non-sterile device. In still other examples, the device may be configured to be primed when the device chamber is not attached to the knob housing 1308 and therefore does not require any passageway to expel the gas. Besides changing the fluid communication, the knob mechanism may also be configured to provide release position which permits detachment of the device chamber 1304 and the knob housing 1306.

Figure 14A:
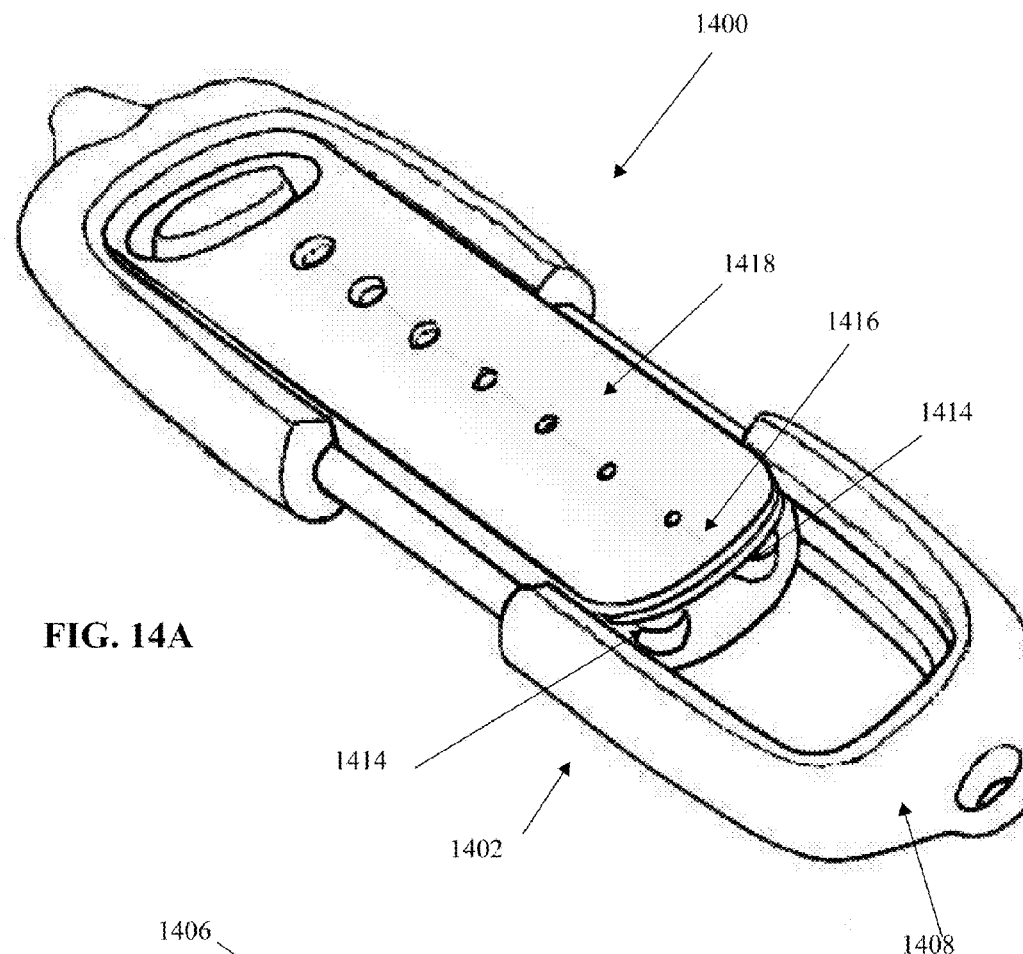
FIG. 14A is a perspective view of another embodiment of a reduced pressure therapy device with an actuator having a rack and pinion.
Figure 14B:
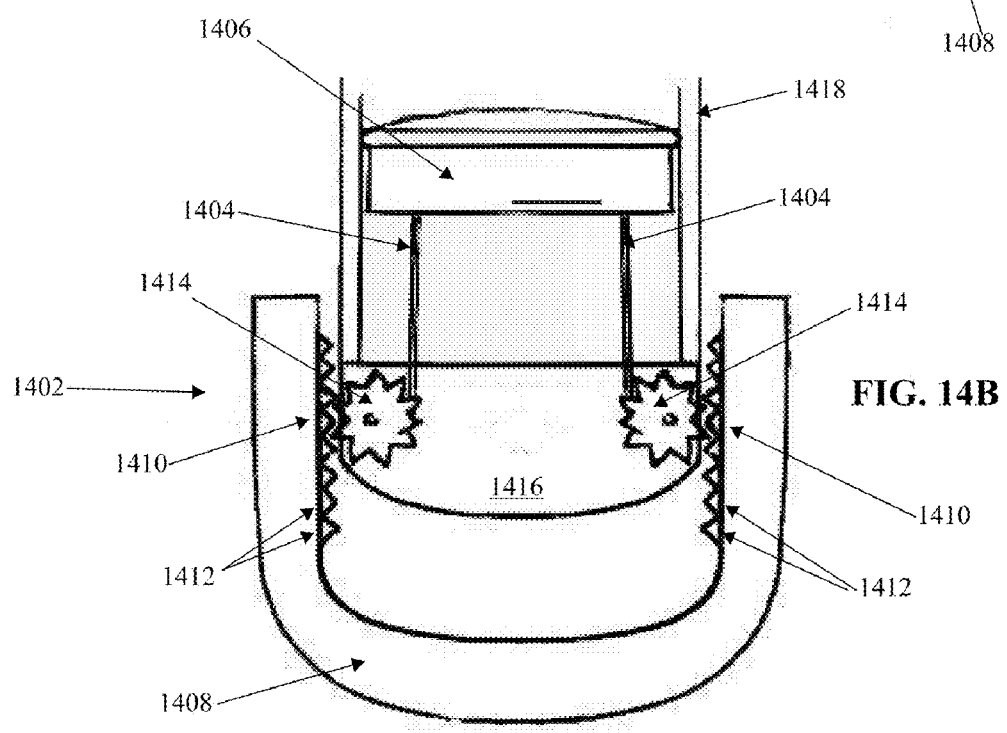
FIG. 14B is a cross-sectional view of the device from FIG. 14A.

As depicted in FIGS. 14A and 14B, in some embodiments, the therapy device 1400 may comprises a rack and pinion mechanism 1402 configured to charge the constant force springs 1404 and to position the sliding seal 1406. In this depicted embodiment, the device 1400 comprises a recharging handle 1408, providing two sets of rails 1410 with rack teeth 1412. Two sets of pinions 1414 are mounted near the proximal end 1416 of the suction apparatus body 1418. The number of rails and pinions in any particular example may vary, depending upon the number of springs. The pinions 1414 are coupled to the constant force springs 1404 which are connected to a sliding seal 1408. The circular motion of the pinions 1414 will drive the motion of the springs 1404 to charge the springs 1404 with potential energy.

The rack and pinion charging mechanism 1402 may be provided in addition to or in lieu of a priming tool charging mechanism. In some examples, when an inadequate seal or connection is made and air enters the closed system, the recharging handle 1410 may be pulled away from the proximal end 1416 of the suction apparatus 1418 and then pushed back towards the proximal end 1416 to recharge the springs 1404. In some examples, the rails and the pinions may be configured to engage in only one direction and not the other, to permit repeat manipulation of the charging mechanism 1402 to increase the magnitude of charging. A device configured with one-way movement of the rack and pinion mechanism may also permit retraction of the seal and springs without requiring that the rack and pinion handle correspondingly retract. Once the device 1400 is re-charged and the dressing seal and/or connections are rechecked, the device 1400 may be reactivated to generate a reduced pressure.

Figure 15B:
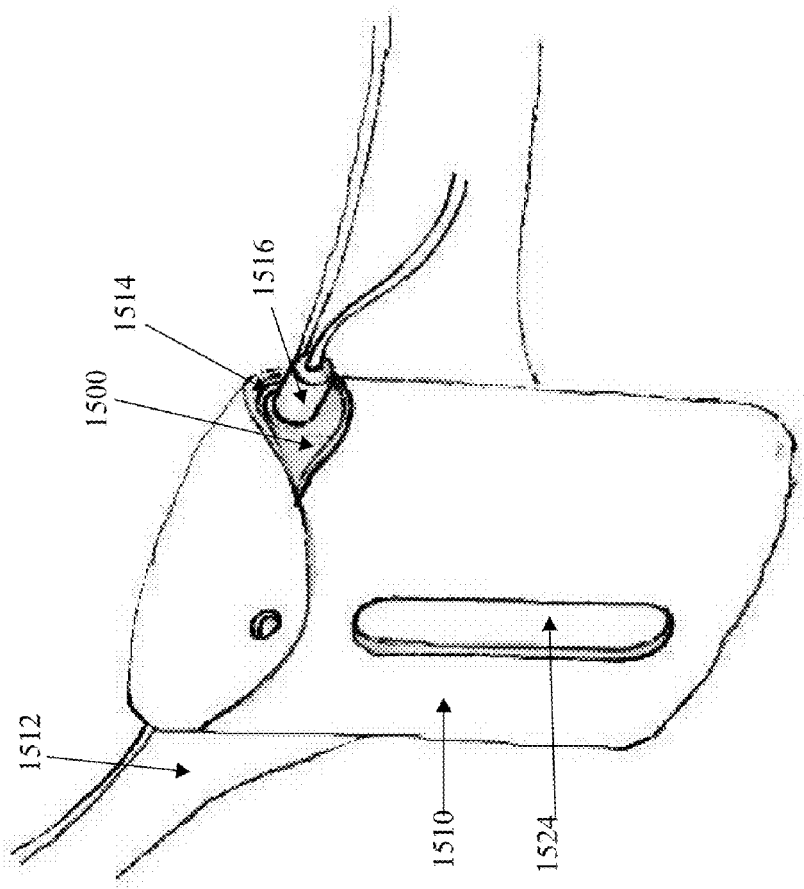
FIG. 15B the device of FIG. 15A held in a carrying case with an attachment strap.
Figure 15A:
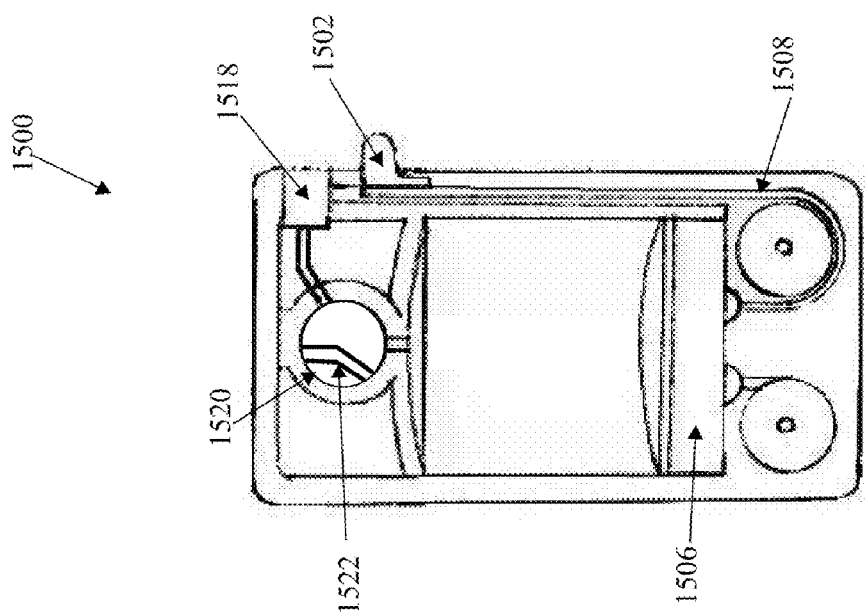
FIG. 15A is perspective view of another embodiment of a reduced pressure therapy device.

FIGS. 15A and 15B depict another embodiment of a reduced pressure therapy device 1500, comprising a slidable lever 1502 that is provided on the body 1504. The slidable lever 1502 is coupled to the sliding seal 1506 using a flexible element 1508 that is configured with sufficient column strength to push the seal 1506 when the flexible element 1508 is pushed using the lever 1502, yet sufficiently flexible bend along the passageway containing the element 1508. The flexible element 1508 permits the lever 1502 to move in a different direction than the seal 1506, which may or may not permit more compact device designs. In alternate embodiments, the flexible element may be configured to pull, rather than push, the seal to a primed position using a slidable lever. In some examples, both a priming tool mechanism and the slidable lever mechanism may be provided for priming the device. As the seal 1506 moves in response to suction of air or exudates, the flexible element 1508 will in turn cause movement of the lever 1502. In some examples, the position of the lever 1502 may be used as an indicator of the remaining potential energy in the device 1500, and in some instances, indicia on the body 1404 near the path of the lever 1502 may be provided to indicate the remaining energy or fill capacity.

In other embodiments, the reduced pressure tissue therapy device may be configured as a portable device that may be carried by the patient or carried the patient's ambulation assistance device (e.g., wheelchair or walker). In other embodiments, the tissue therapy device is designed such that it may be secured to the patient (e.g. limb or torso). The tissue therapy device may be attached to the patient by any suitable means for securing the device to the patient known to those skilled in the art. In some embodiments, the device may be secured through the use of adhesive tape. In other embodiments, the device may be secured to the patient through the use of a strap, a hook-and-loop fasteners such as VELCRO®, an elastic band, a cuff, an adhesive bandage, or any other suitable mechanisms for securing the device. In other embodiments, the device comprises a detachable clip. In yet other embodiments, the device further comprises a holster or other type of pocket structure to hold the suction apparatus.

As illustrated in FIG. 15B, the reduced pressure therapy device 1500 may be kept in a pouch 1510 or other holder that can be further attached to a belt or a wrap 1512, for example. The pouch 1510 may comprise an opening 1514 through which an extension tube 1516 of the device 1500 can extend. The pouch 1510 may also comprise a viewing opening or window 1524 which have a pouch location that corresponds to a viewing window of the device 1500, for example. As may be seen in FIGS. 15A and 15B, the suction inlet 1518 need not be coaxial with the movement axis of the seal 1506. Furthermore, the control valve 1520 of the device 1500 may also comprise a non-linear valve conduit 1522 that need not pass through the rotation axis (if any) of the valve 1520.

In some embodiments, the tissue therapy device may be held or encased in soft or resilient materials, e.g., a dense foam. In some instances, use of foams or other soft or resilient materials may increase comfort during use, and may reduce the risk of injury to the device or the user when the device is accidentally bumped, or from pressure points that may occur with long-term use. FIGS. 16A to 16E illustrate one example of such a device 1600. In some examples, the soft covering 1602 is integrally formed with the device 1600, while in other embodiments, the device 1600 may be removable and re-encased in the soft casing 1602. In some examples, the device 1600 and the soft casing 1602 may have different outer shapes or colors, which may permit changing of ornamentation to mask the nature of the device 1600, which may improve patient confidence using the device in public and/or patient compliance with the device 1600. In another example, an oval casing may be configured to engage a box-like device to eliminate any corners. Moreover, the greater surface area of such casing may reduce the risk of causing focal pressure points or regions as a result of securing the tissue therapy device directly to a user's body. To reduce potential bulkiness, the casing 1602 need not fully encase the device 1600 and may have one or more openings 1604. Openings 1606 may also be provided to access to chamber windows or actuators of the device 1600, or to remove a collection chamber from the device 1600. The device 1600 may also comprise an internal frame 1608 to support components of the device 1600 such as the valve or spring posts (not shown) for example.

Figure 16A:
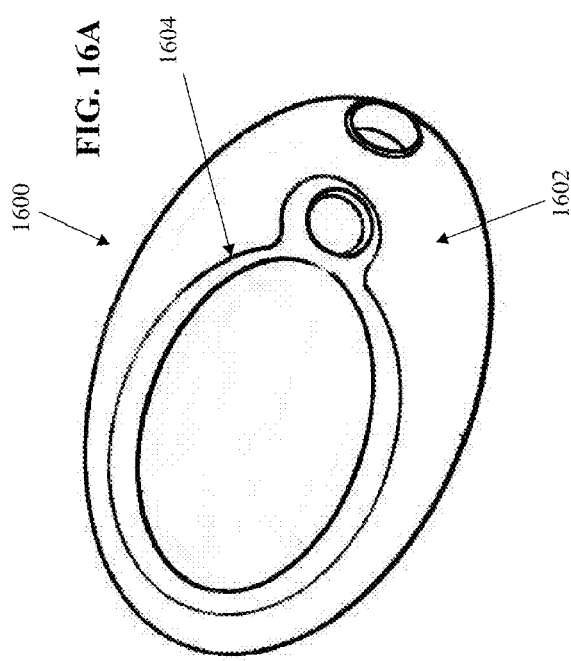
FIG. 16A is a perspective view of another embodiment of a reduced pressure therapy device.
Figures 16B, 16C, 16D:
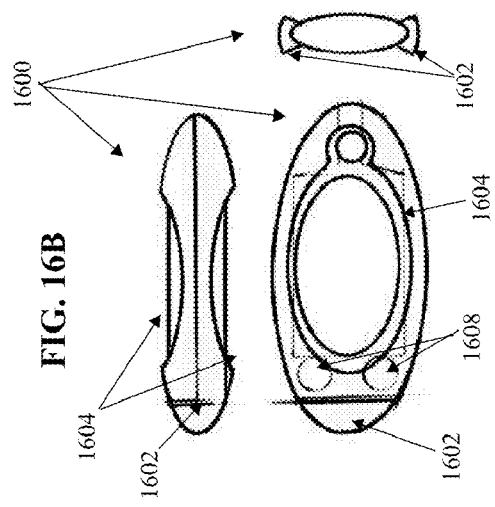
FIG. 16B is a superior view of the device of FIG. 16A.
FIGS. 16C and 16D are side and end elevational views, of the device from FIG. 16A.
Figures 16E, 16F:
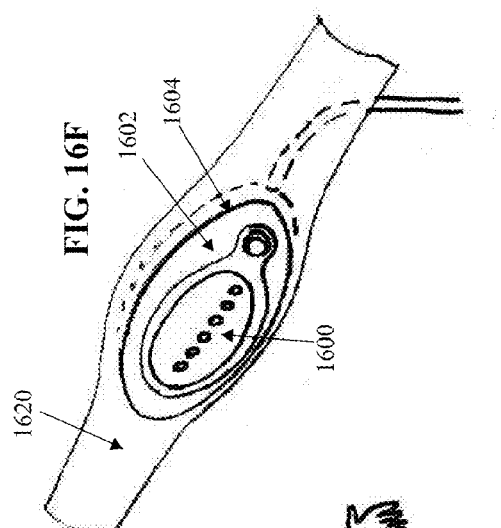
FIG. 16E is a perspective view of a device holder.
FIG. 16F is a schematic perspective view of the device holder used with the device.
Figure 16G:
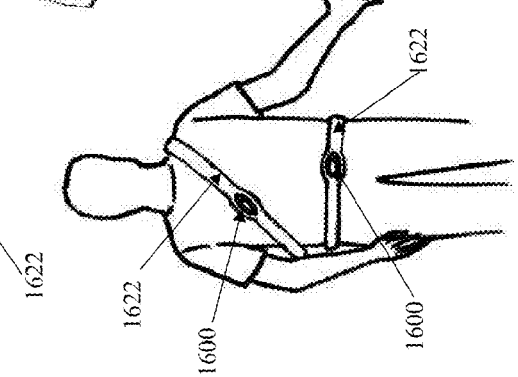
FIG. 16G is a schematic illustration of embodiments for wearing or securing the device from FIG. 16A to a user's body.

In one further embodiment, the encased therapy device 1600 may be configured to attach to a strap 1620 which may permit the encased device 1600 to snap into a cavity 1622 of the strap. Alternatively, zippers or other fastener mechanisms may be used to secure the device 1600 into the cavity 1622. In some examples, a soft casing 1602 is not used or provided, and the materials about the cavity 1622, if not at least a portion or all of the strap, comprises soft materials. The strap may comprise a closed loop of elastic material, or may comprise an open loop with a buckle, clasp or other fastening mechanism that may be used to close the loop. As depicted in FIG. 16E, the strap 1620 may be worn in a variety of ways to secure the device to the user, including the waist or across the torso. In still other embodiments, the device is not secured against the user and may be carried as a loose shoulder strap.

Figure 17A:
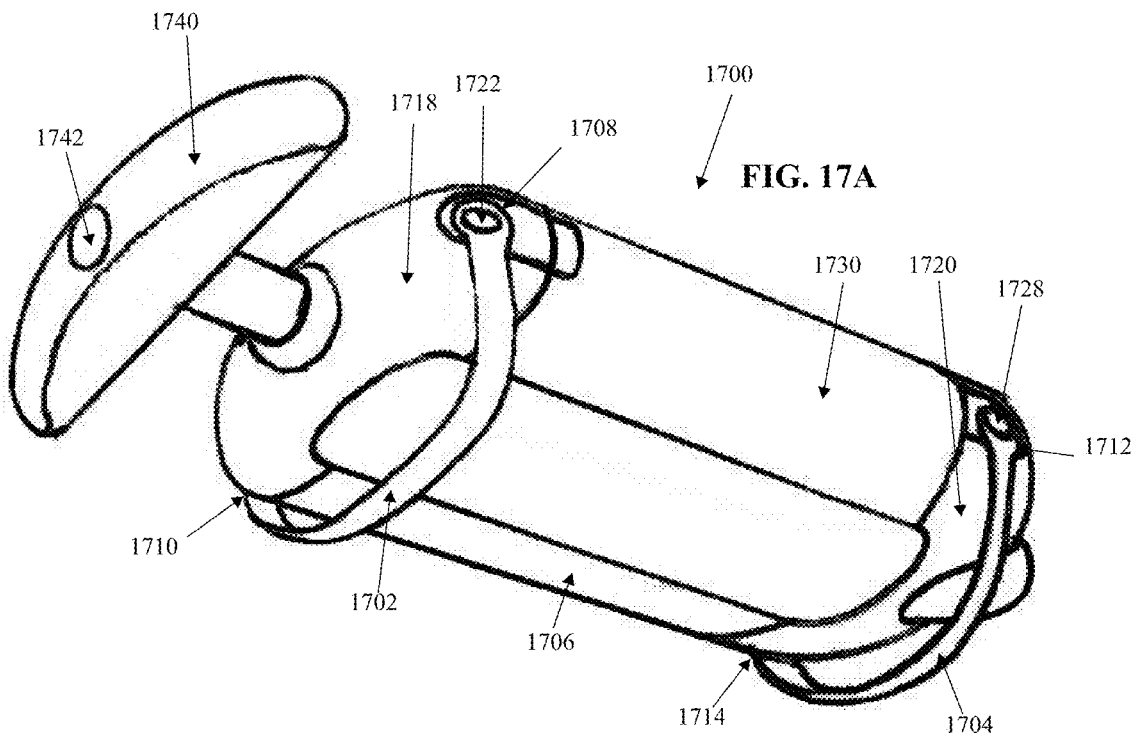
FIGS. 17A and 17B are perspective views of exemplary embodiments of an attachment mechanism for the reduced pressure therapy device.
Figure 17B:
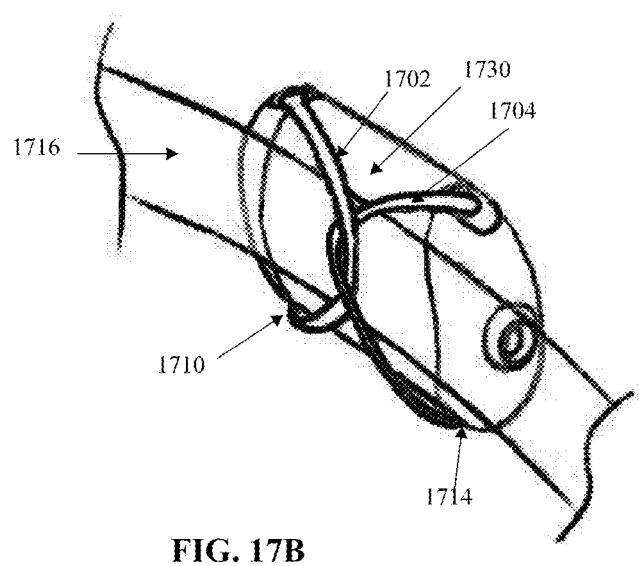

FIGS. 17A and 17B illustrate another example of an attaching mechanism for a suction apparatus 1700, comprising at least one elastomeric band 1702 and 1704 attached to the body 1706 of the suction apparatus 1700. Bands of various sizes, i.e., length, width, thicknesses, cross-sectional shapes and a variety of materials can be included in the therapy device kit to suit different needs. For example, larger bands may be provided for attachment around the limbs or torso. These larger bands may be removed by the user and replaced with shorter bands provided for attachment to a belt, strap or sash. The ends 1708, 1710, 1712 and 1714 of the bands 1702 and 1704 may be configured to be releasably attachable to the body 1706 of the device 1700, which may permit crossing or interlocking of the bands 1702 and 1704, as shown in FIG. 17B. In some instances, as illustrated in FIG. 17B, the two elastomer bands 1702 and 1704 may be crossed over when coupled to the body 1704 of the device 1700 for use with a belt or wrap 1716 that can be worn by the user. In FIGS. 17A and 17B, while each end 1708, 1710, 1712 and 1714 of their respective bands 1702 and 1704 are be coupled to attachment sites 1722 and 1728 on the same end cap structure 1718 and 1720 of the body 1704, in other examples, at least one band may have ends coupled to different end cap structures. The attachment sites 1722, 1724, 1726 and 1728 are located on the sides of the end cap structures 1718 and 1720, but in other embodiments may be located on the end surfaces or the top or bottom surfaces of the end cap structures or the collection chamber 1730. In some instances, it may be beneficial to use at least one band 1702 and 1704 to keep attach the end cap structures 1718 and 1720 together when the when the collecting chamber 1730 is removed from the device 1700.

Figure 18:
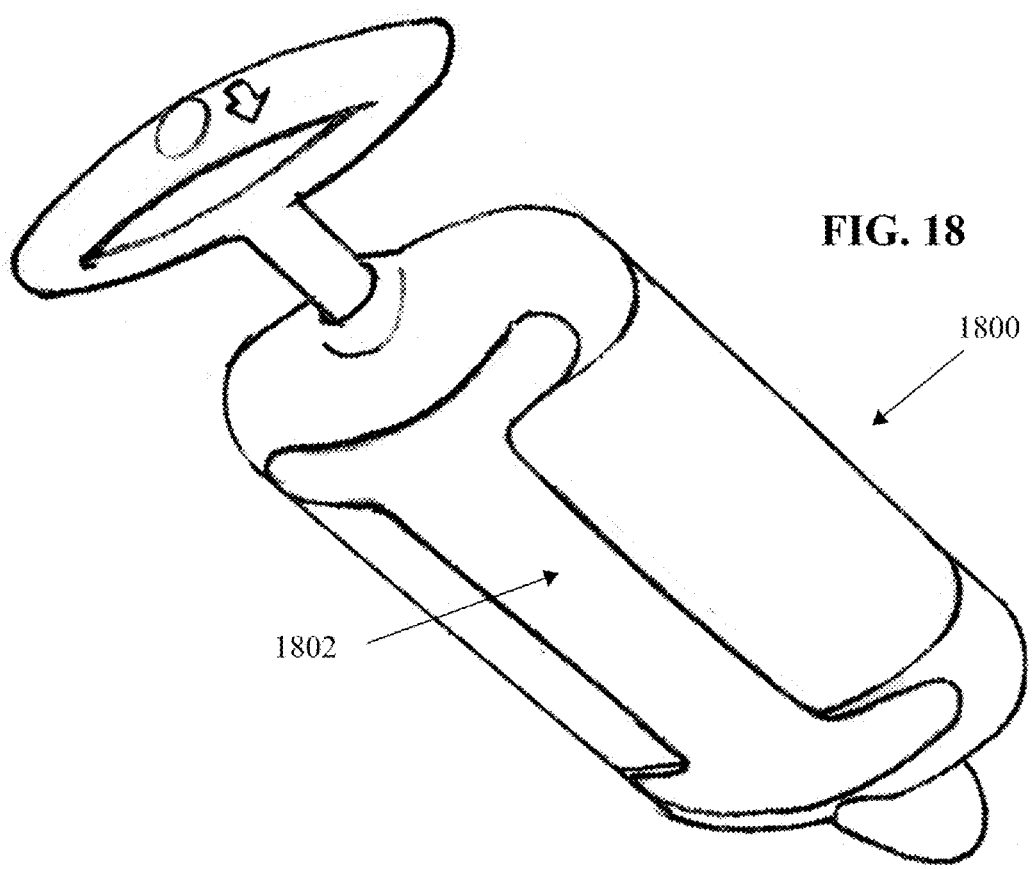
FIG. 18 is schematically illustrates another embodiment of an attachment mechanism of a reduced pressure therapy device comprising an elastomer strap.

Although the bands 1702 and 1704 in the embodiment illustrated in FIGS. 17A and 17B have a generally elongate configuration, other configurations are also contemplated, including I-shaped, H-shaped or X-shaped bands. In some examples, a single band structure may be coupled to more than two or even all of the attachment sites. In FIG. 18A, for example, the device 1800 comprises a H-shaped strap 1802. In some examples, a H-shaped strap 1802 may result in less interference with the surface 1804 of the device 1800, which may facilitate the application of adhesive labels, writing or other indicia onto the device 1800. In some examples, this strap configuration may permit multiple ways for a belt or a wrap to pass through the strap and may provide flexibility to the user on how to wear or secure the device. Referring back to FIG. 17, the body 1704 of device 1700 may have fewer or a greater number of attachment sites 1722, 1724, 1726 and 1728 than four, and not every attachment site needs to be used. In other embodiments, multiple attachment structures or openings may be provided on the band so that the cross-sectional area between the band and the body of the device can be adjusted. In still other embodiments, the attachment sites on the body of the device may be configured to slide, rotate and/or pivot. The structure of bands may be uniform or non-uniform along any dimension of the bands, e.g. a band may have a greater width in a central segment of the band compared to the end segments.

Figure 19A:
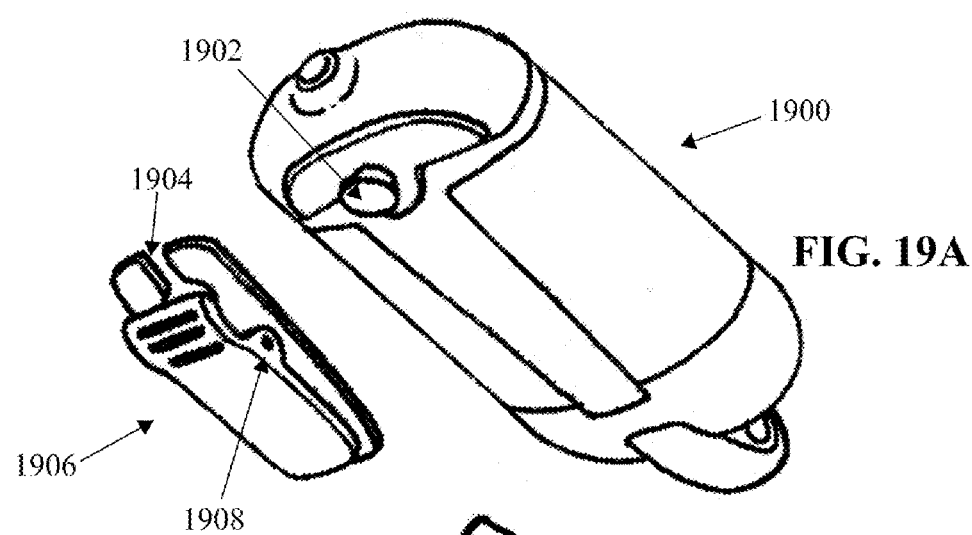
FIG. 19A schematically illustrates another embodiment of a reduced pressure therapy device comprising a detachable and rotatable clip.
Figure 19B:
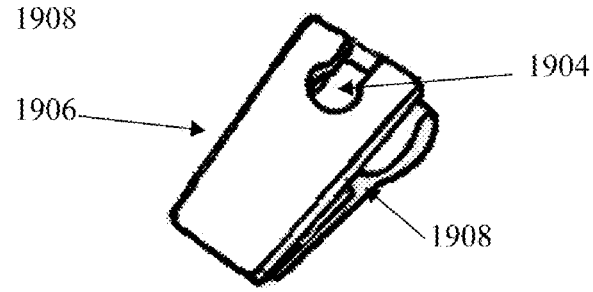
FIG. 19B is a posterior perspective view of the clip in FIG. 19A.
Figure 20:
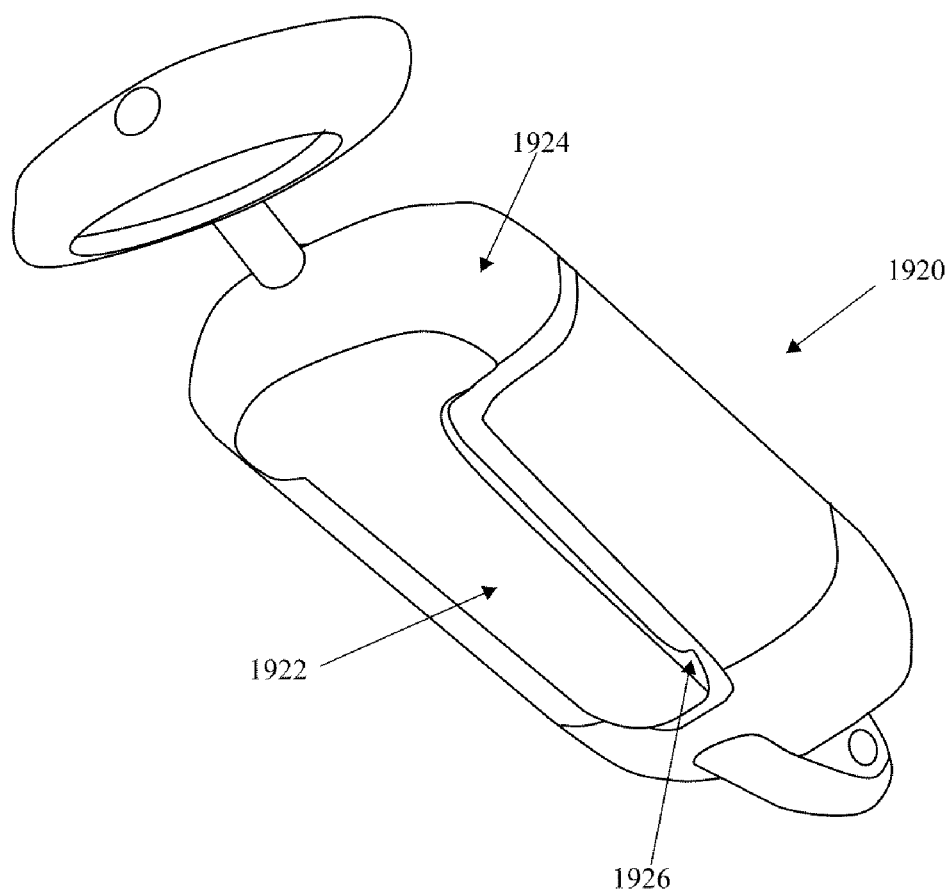
FIG. 20 is a perspective view of another embodiment of a reduced pressure therapy device comprising an integrated clip.

In yet another embodiment of a reduced pressure therapy device 1900 in FIG. 19A, the device 1900 comprises an attachment site with a mounting post or stud 1902 that may be coupled to slotted opening 1904 of the a clip 1906, as shown in FIG. 19B. Referring back to FIG. 19A, in certain embodiments, the clip 1906 and the post 1902 are configured to permit rotation of the device 1900 with respect to the clip 1906. The clip attachment site may be located anywhere on the body of the device. In other examples, the clip mechanism may be releasably attached to the device 1900 using any of a variety of other interfaces, including but not limited to where the attachment site on the body of the device comprises an opening, recess or groove and the clip comprises a complementary post or other structure configured to couple to the opening, recess or groove. The clip may have any of a variety of lengths or widths, and in some examples, multiple clips with different configurations may be in a kit containing the device. Although the clip 1904 in FIG. 19A is articulated with a spring biased pivot mechanism 1908, in some the clip may have a generally fixed configuration and comprise a rigid or semi-rigid material. Also, in other embodiments, the clip structure may be integrally formed with the body of the device. In FIG. 20, for example, the reduced pressure therapy device 1920 comprises an integrally formed, unarticulated clip 1922 that is attached to one of the end caps 1924 of the device 1920. The distal end 1926 of the clip 1922 may have an increased thickness, which may resist inadvertent separation of the clip 1922 from the belt or strap to which it may be clipped.

Referring back to FIG. 17A, in some examples, the device 1700 may comprise a priming tool 1740 with a locking actuator 1742. The actuator 1742 may be configured deform or displace a locking structure of the tool 1740 or to otherwise unlock the tool 1740 to permit its movement. The unlocked movement may include axial and/or rotational displacement. The locking actuator 1742 may be configured to resist, for example, inadvertent activation of the device 1700 or withdrawal of the priming tool 1740.

In some embodiments, the suction apparatus may comprise a window or viewing region which permits visual assessment of the pressure level and/or the exudates without removal or opening of the device. FIG. 21A illustrates one example of a non-circular suction device 2000 comprising a longitudinally oriented window 2002 located on a surface 2004 of the device 2000. The non-circular seal may be viewable through the window 2002 and the seal may comprise seal indicia which may be viewed with respect to body indicia or window indicia 2010 to assess the position of the seal and/or the remaining amount of potential energy remaining in the device 2000. An exudate volume scale or set of indicia may also be provided about the window. In some examples, by tilting the device and utilizing gravity, the amount of exudate contained in the device 2000 may be assessed using the volume scale. In some further examples, more than one window region may be provided. Referring still to the device 2000 in FIG. 21A, a proximal window 2012 may be provided along a different circumferential region from the first window 2002 with respect to the longitudinal movement axis of the seal 2006. When the seal 2006 is in a proximal region, indicia or a different surface of the seal 2006 not visible when the seal 2006 is distal to the proximal region may be visible at the proximal window 2012, and may be used to indicate that the potential energy in the device 2000 has been depleted, that the device has not been charged, and/or that the device has failed. In other examples, a distal window (not shown) may also be provided to indicate that the device has been primed. The region of the seal configured to be visible at the distal window may or may not be circumferentially aligned with the proximal window of the device (if any). In some examples, the proximal window and/or the distal window has a dimension as measured along the movement axis of the seal that is less than the dimension of the seal along the movement axis if the seal. In some specific examples, the dimension of the proximal and distal window as measured along the movement axis is 50% or less than the dimension of the seal along the movement axis if the seal.

Although the window(s) of the reduced pressure therapy device may be circular, ovoid, square, rectangular or otherwise polygonal (with sharp angles or rounded angles), and each window may be limited to one surface of the device, in other examples, the windows may have any of a variety of shapes and may span two or more surfaces of the device. In FIG. 21B, for example, the device 2020 comprises a window 2022 with a longitudinal region 2024 that is contiguous with a transverse proximal region 2026 and a transverse distal region 2028. As illustrated in FIG. 21B, the proximal and distal regions 2026 and 2028 may be configured to span a superior surface 2030 of the device 2020 as well as the side surfaces 2032 and 2034. The longitudinally configured portions of the windows need not have a uniform width, and the proximal and distal regions of the window (if any) need not have the same configuration. FIG. 21C, for example, depicts a device 2040 comprising a window 2042 with a longitudinal region 2044 that tapers distally and also comprises a proximal region 2046 but not a distal region.

In some embodiments, a method of applying reduced pressure therapy to an area of damaged tissue is provided, comprising: affixing a sealant layer around an area of tissue to be treated; creating a sealed enclosure around the area of the tissue with the sealant layer; priming a suction apparatus by positioning a reciprocating member contained in the suction apparatus to an extended position where the effective collecting volume of the suction apparatus is about zero; creating a fluid communication between the sealed enclosure and the suction apparatus; and activating the suction apparatus by drawing back the reciprocating member to a retracted position thereby forcefully expanding the volume of the air originally located within the sealed wound enclosure and generating a reduced pressure level within the sealed enclosure.

Figure 22:
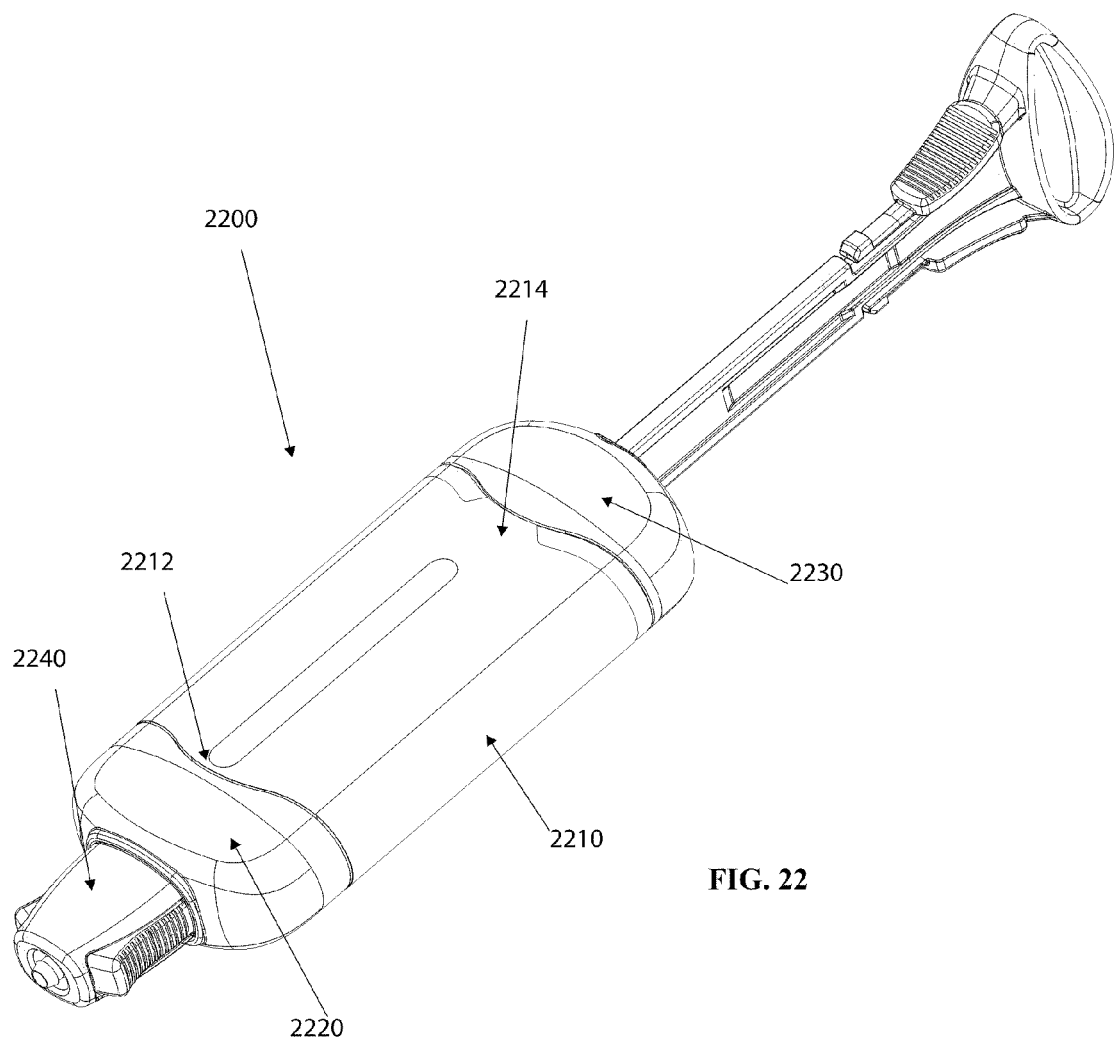
FIG. 22 is perspective view of one embodiment of a suction apparatus.
Figure 23A:
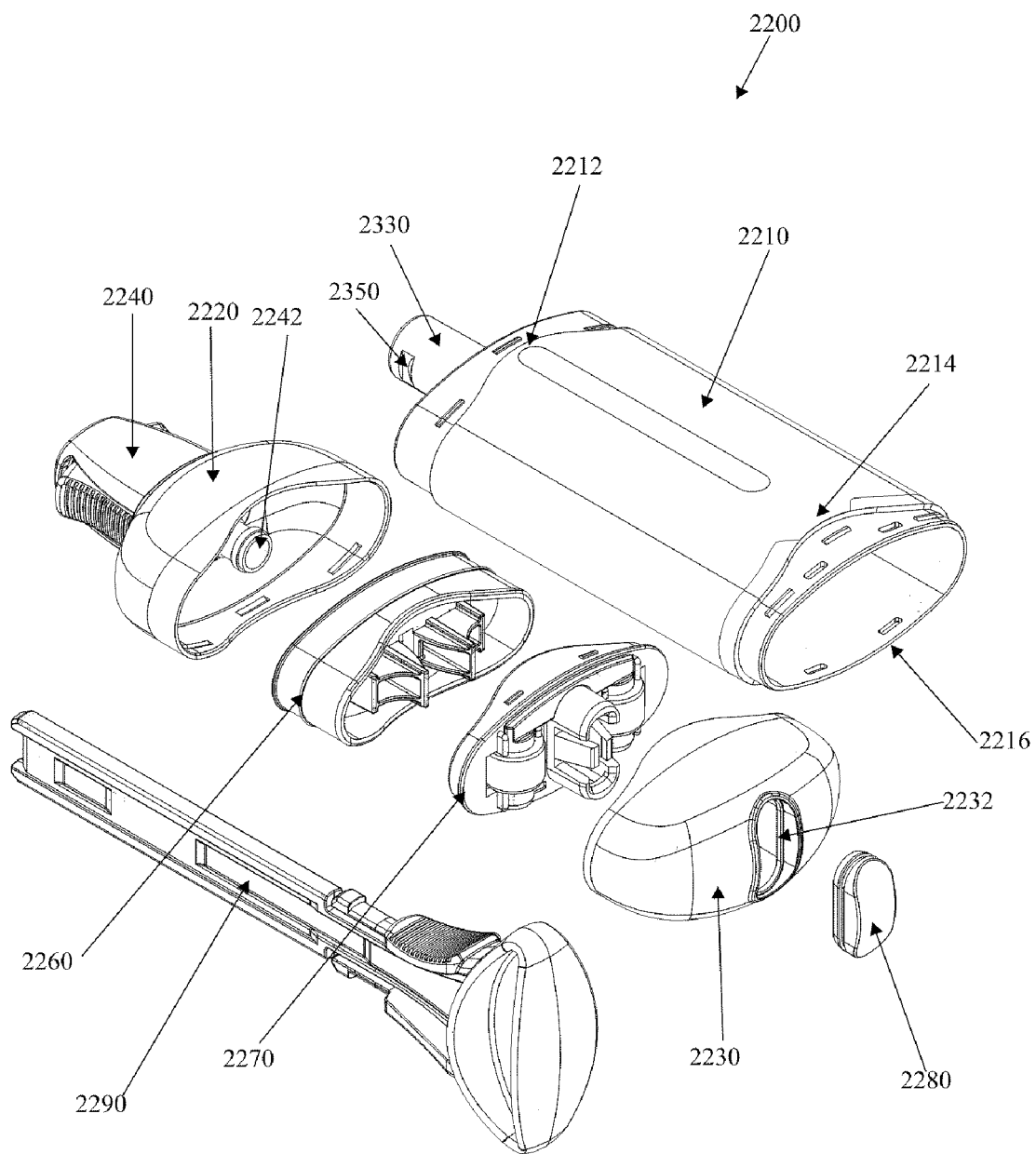
FIGS. 23A and 23B are posterior and anterior perspective component views of the embodiment from FIG. 22.
Figure 23B:
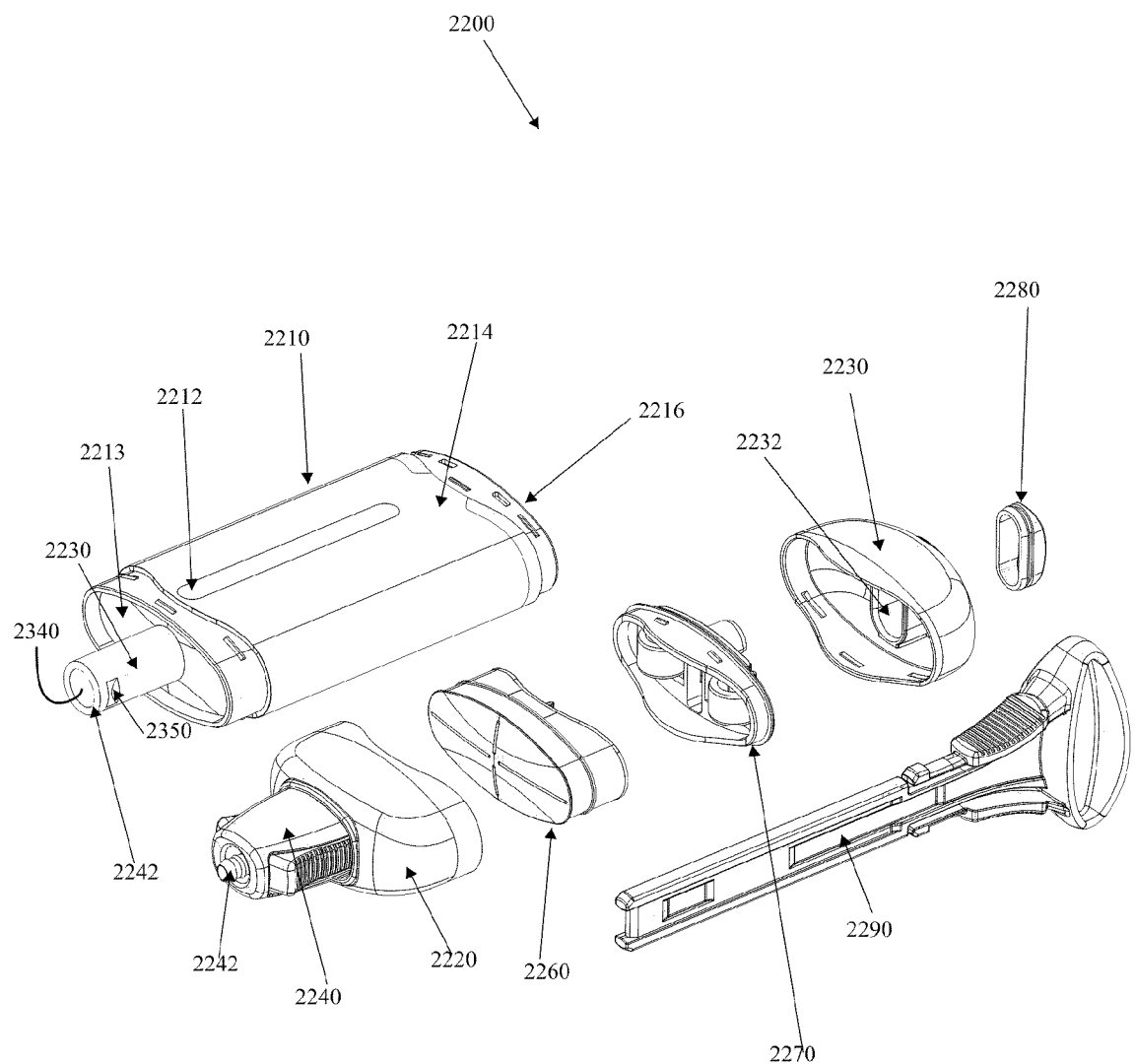

Another embodiment of a suction apparatus 2200 is illustrated in FIGS. 22, 23A and 23B. Suction apparatus 2200 comprises a suction chamber 2210 having a distal end 2212 and a proximal end 2214, a front cap 2220 and a rear cap 2230. The front cap 2220 and the rear cap 2230 may be configured to be detachably secured to the distal end 2212 and the proximal end 2214 of the suction chamber 2210, respectively. The proximal end 2212 and/or the distal end 2214 of the suction chamber 2210 may also comprise notches 2360 and 2370, respectively, which may be configured to facilitate coupling to the rear cap 2230 and/or front cap 2220 of the device 2200, respectively. Notches 2372 or apertures may also be provided for attaching the spring assembly 2270 to the suction chamber 2210. A fitting housing 2240 may be coupled to the front cap 2220, enclosing a fitting 2242 that may be configured to connect the suction chamber 2210 with another component of the therapy system (e.g., an extension tube or an attachment port on a sealant layer). The suction chamber may be fabricated from a rigid polymer adapted to maintain the external shape of the suction chamber shape under reduced pressure. In some embodiments, the entire body of the suction chamber may be transparent, thereby permitting visual inspection the quantity and quality of wound exudates contained therein. In other embodiments, the suction chamber may comprise a non-transparent body but with an inspection window.

As mentioned above, the fitting housing 2240 may be configured to removably detach from to the front cap 2220, while in other examples, the fitting housing may be integrally formed with the front cap 2220 or otherwise configured not to be detached once joined. A piston assembly may be movably located within the suction chamber 2210. The piston assembly 2260 may be coupled to a spring assembly secured to the rear cap 2230 of the suction apparatus 2200. In other embodiments, the spring assembly 2270 may also be secured about the proximal opening 2216 of the suction chamber 2210. An opening 2232 may be provided in the rear cap 2230 to permit insertion of a priming tool 2290 which is configured to prime the suction apparatus 2200. Once the suction apparatus 2200 is primed and activated, the priming tool 2290 may be removed, and the opening 2232 on the rear cap 2230 may be closed by a rear cap seal 2280. The rear cap seal 2280 may be any type of seal that may prevent entry of undesired contaminants or other environmental agents (e.g. water during showering) into the suction chamber 2210. In other examples, the rear cap seal may be attached to the rear cap by a tether. In still other examples, the rear cap seal may be configured with a passageway or slit and comprises a deformable material that permits insertion and/or removal of the priming tool and reseals upon removal of the priming tool. In the latter embodiments, the rear cap seal need not be removed before priming or inserted back into the opening after removal of the priming tool.

Figure 24A:
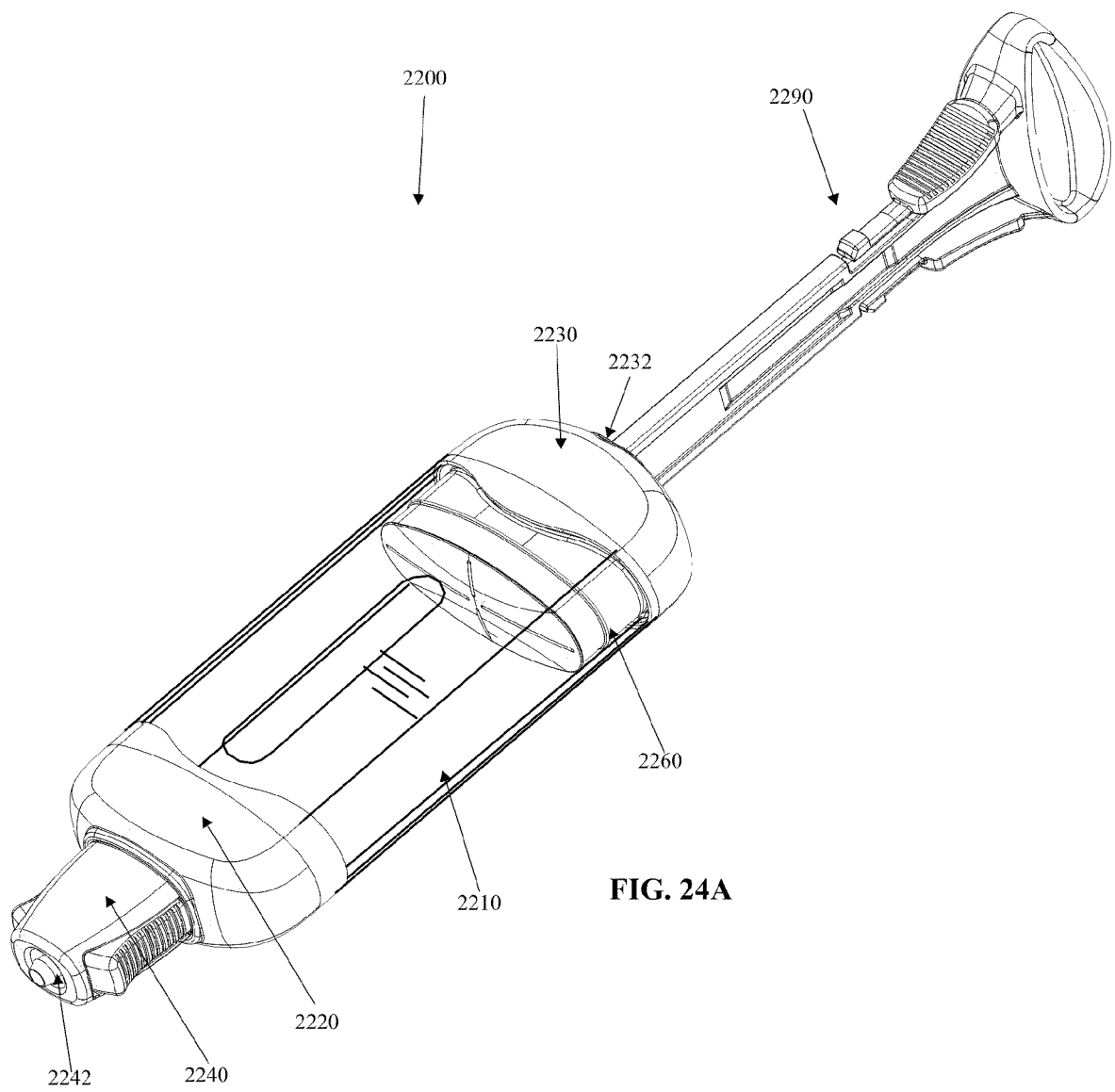
FIG. 24A depicts another embodiment of a reduced pressure therapy device comprising a clear collection chamber wherein the device is not primed.
Figure 24B:
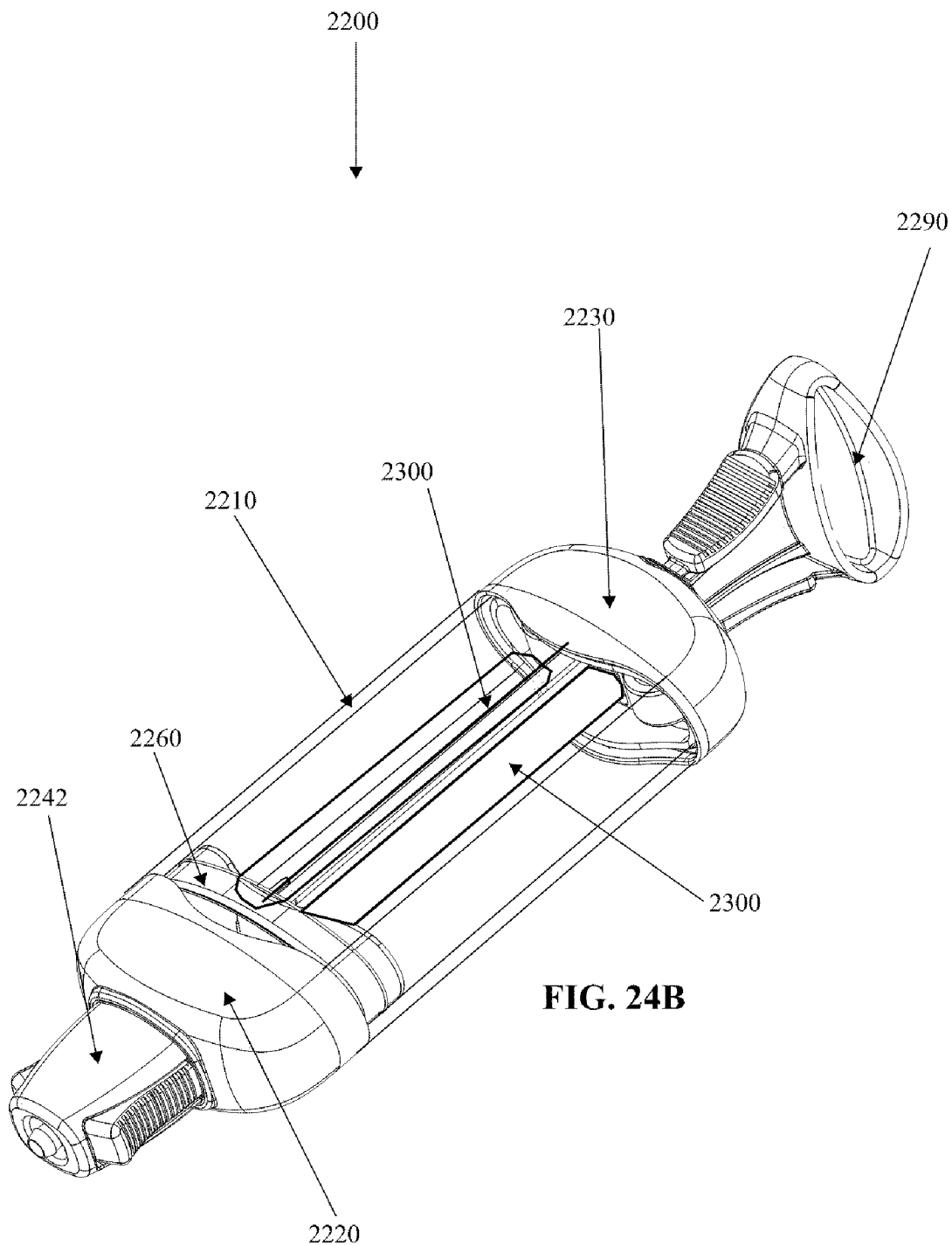
FIG. 24B depicts the device of FIG. 24A in a primed configuration.
Figure 24C:
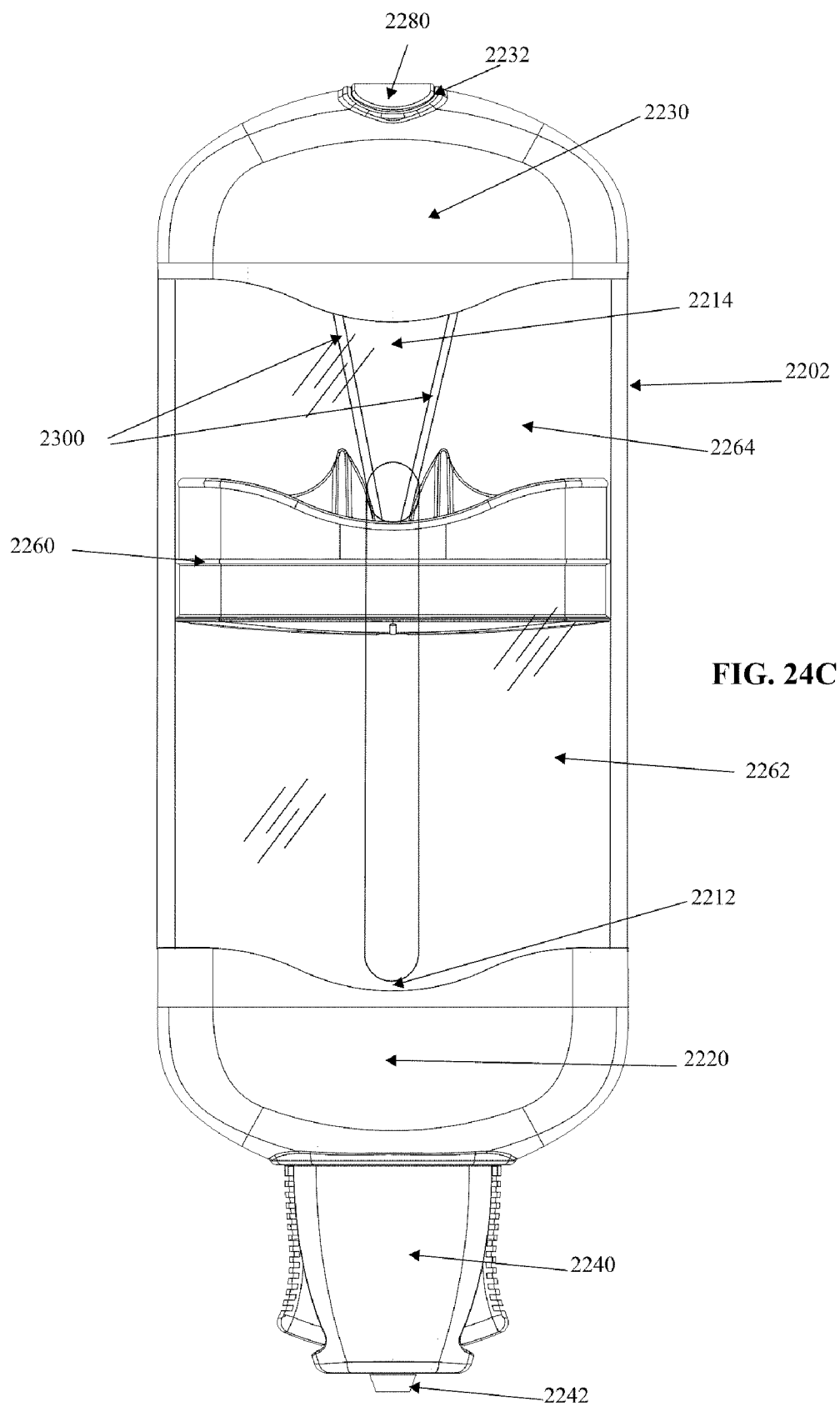
FIGS. 24C and 24D or superior and side elevational views of the device in FIGS. 24A and 24B in an activated and partially expended state.
Figure 24D:
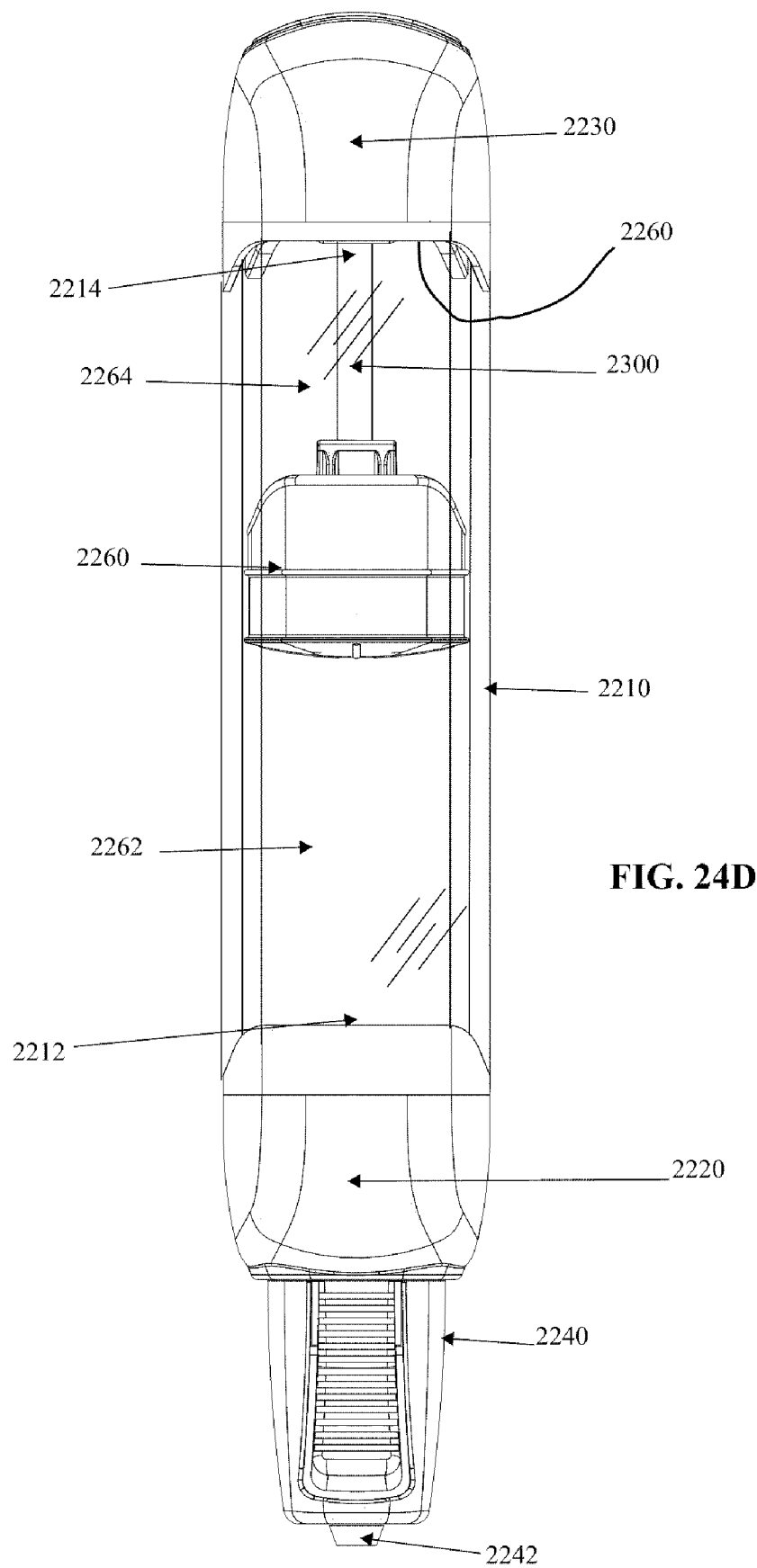

FIG. 24A is a perspective view of the embodiment of the suction apparatus 2200 in a configuration before priming and comprising a collection chamber 2210 made of a translucent or optically clear material, with the piston assembly 2260 in a proximal position and the priming tool 2290 inserted into the opening 2232 of the rear cap 2230 but not yet displacing the piston assembly 2260. To prime the suction apparatus 2200, the priming tool 2290 may by further inserted through the opening 2232 of the rear cap 2230 to push the piston assembly 2260 into the suction chamber 2210. Depending upon the particular configuration, the priming tool may be pushed until the piston assembly contacts the distal end wall until it is adjacent the distal end wall of the suction chamber, until the springs are maximally extended, and/or mechanical interference between the priming tool and the rear cap resist further insertion. FIG. 24B depicts the suction apparatus 2200 in the primed configuration. The priming tool 2290 has pushed the piston assembly 2260 into a distal position and has extended the springs 2300 coupling the piston assembly 2260 to the spring assembly 2270 and generated potential energy within the springs 2300. Upon removal of the priming tool 2290, the springs 2300 are able to exert a proximal directed force onto the piston assembly 2260, which is capable of generating reduced pressure in the suction chamber 2210 and transmitting the reduced pressure to a sealed wound enclosure coupled to the device 2200. FIGS. 24C and 24D are superior and side elevational views of the device from FIG. 24A in an activated state and with the springs 2300 having partially expended the potential energy from the fully primed configuration. As can be seen when the piston assembly 2260 is in a partially expended position, the suction chamber 2210 may be subdivided by the piston assembly 2260 into a collection chamber 2262 and a working chamber 2264, where the collection chamber 2262 is the space between the piston assembly 2260 and the distal end wall 2213 of the suction chamber 2210, and the working chamber 2264 is the space between the proximal end 2214 of the suction chamber 2210 and the piston assembly 2260 which contain the springs 2300. When the suction apparatus is in the primed configuration, the volume of the collection chamber may be about zero, or sometimes less than about 5 cc. In some instances, upon activation of the primed device, the collection chamber may increase in volume up to about 3%, sometimes about 5% and other times about 10% or even about 20% until the force exerted by the springs 2300 is counterbalanced by the force generated by the reduced pressure in the collection chamber 2310.

Figure 25A:
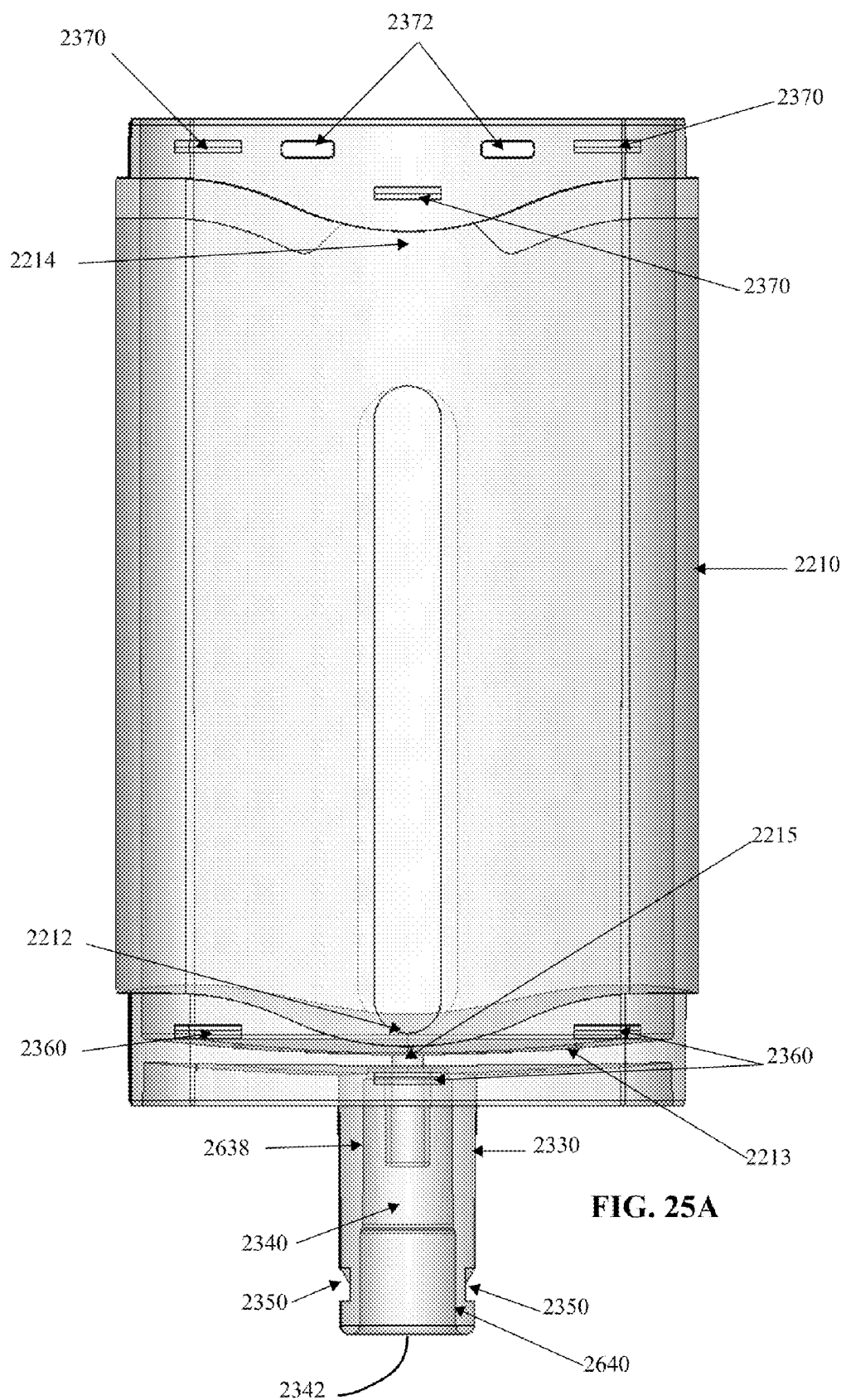
FIG. 25A is a superior elevational view of the suction chamber.
Figure 25B:
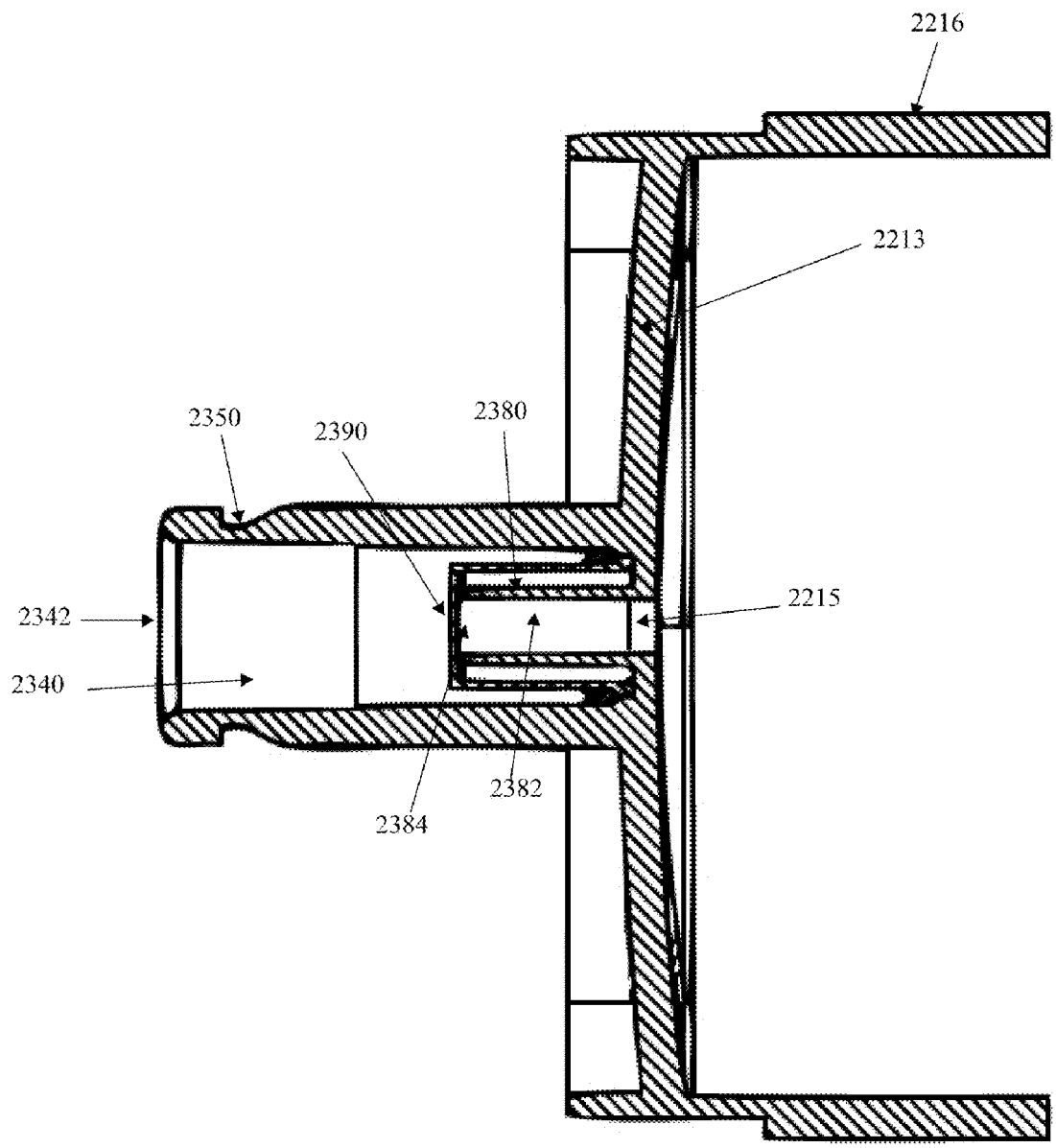
FIG. 25B is a cross-sectional view of the distal end of the suction chamber.

FIG. 25A provides a detailed superior view of the suction chamber 2210 and FIG. 25B provides a cross-sectional view of the distal portion of the suction chamber 2210 from FIG. 25A. As may be seen in the perspective views in FIGS. 22 to 24B, the suction chamber 2210, may comprise a non-circular cross-sectional shape with respect to a transverse plane to the movement axis of the piston assembly, which in some configurations lies between the distal end 2212 and proximal end 2214 of the suction chamber 2210. In other examples, the cross-sectional shape of the suction chamber may have any of a variety of other types of geometric configurations (e.g., cylindrical, rectangular, etc.). As mentioned previously, the distal end wall 2213 of the suction chamber 2210 may further comprise a distal opening to permit communication with the suction chamber. The distal end wall 2213 of the suction chamber 2210 may further comprise a conduit 2330 or other extension structure. The conduit 2330 comprises a conduit lumen 2340 with a conduit opening 2342 which are in fluid communication with the collection chamber 2310 of the suction chamber via the distal opening 2215 of the distal end wall 2213. The conduit 2330 may comprise any of a variety of notches 2350, grooves or flanges, which may facilitate attachment of the conduit 2330 to one or more components associated with the fitting housing 2240.

Although a user-controlled valve may be provided in some embodiments to open or close fluid communication with the suction chamber, in some examples, the fluid communication may be controlled automatically by the coupling and/or decoupling of the device components. For example, the conduit 2330 of the device 2200 may also comprise an inner conduit 2380 located in the main conduit lumen 2340, the inner conduit 2380 comprising an inner conduit lumen 2382 and an inner conduit opening 2384. Referring to FIG. 25B, a chamber slit seal 2390 may be located about the inner conduit opening 2384. In its base configuration, the chamber slit seal 2390 may be configured with a normally closed configuration to block fluid communication through the conduit 2330. In some examples, a chamber slit seal 2390 may be opened by inserting a structure through the seal to deform it and maintain the patency of the opening formed in the seal. As will be explained in greater detail below, in other examples, such as the slit seal 2390 in FIG. 25B, the slit seal 2390 may be configured to be pushed over, around, and/or down toward the base of the inner conduit 2380 when a complementary structure is inserted into the main conduit lumen 2340.

Figure 26A:
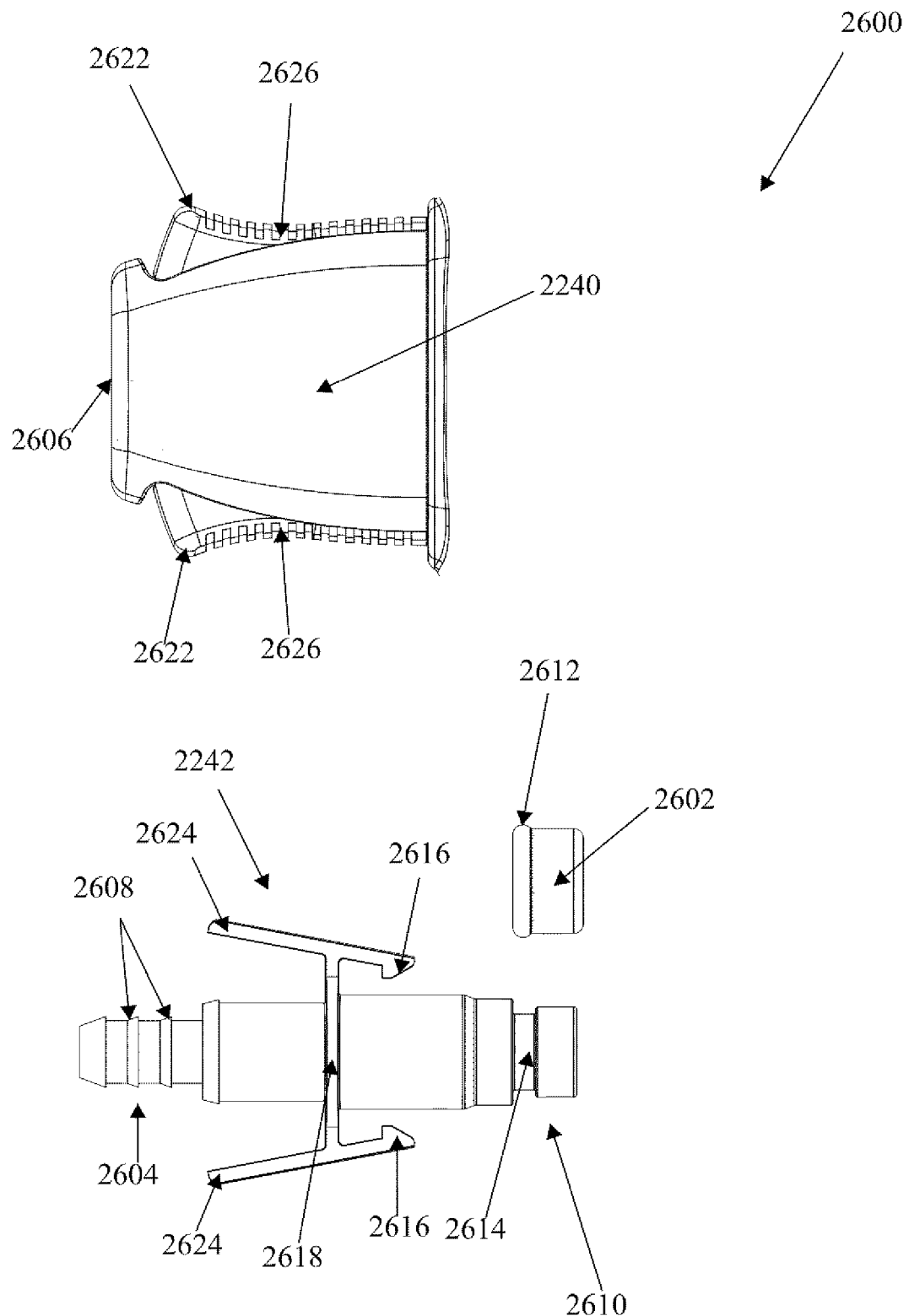
FIG. 26A is a component view of a fitting assembly.

FIG. 26A is a top component view of a fitting assembly 2600, comprising the fitting housing 2240, a fitting 2242 and a fitting slit seal 2602. As mentioned previously, the fitting housing 2240 may be configured to permanently or detachably couple to the front cap 2220 of the device 2200, or may be integrally formed with the front cap. In the embodiment shown in FIG. 26A, fitting 2610 comprises a connector section 2604 that is accessible through an opening 2606 in the fitting housing 2240 and permits a complementary fit with the connector of another component. For example, connector section 2604 may be coupled to a connector of an extension tube or the attachment port of a sealing layer with a snap fit or an interference fit. In the specific example in FIG. 26A, the connector section 2604 comprises multiple flanges 2608 which may be used to provide a resistance fit with tubing, but may also be used with a complementary connector to form a complementary interfit.

Figure 26B:
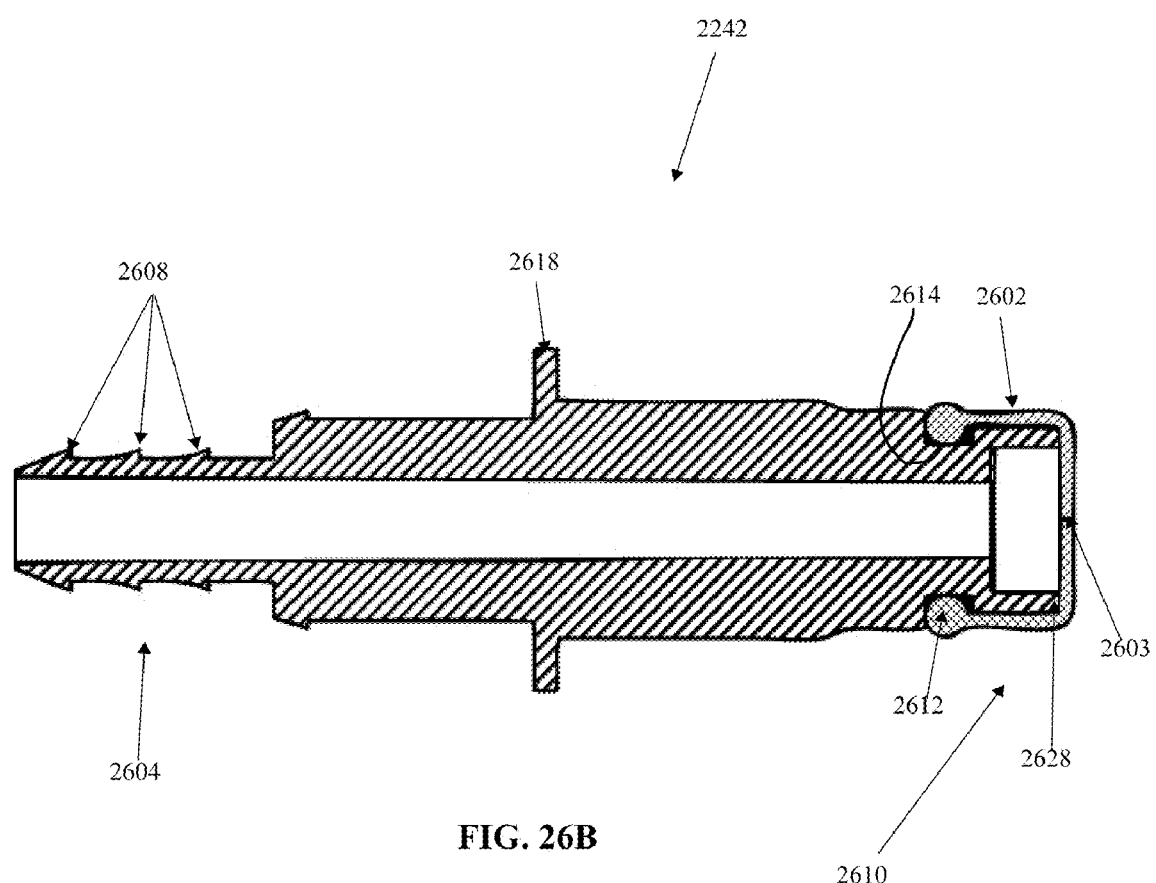
FIG. 26B is a cross-sectional view of the fitting of the fitting assembly from FIG. 26A.

Referring to FIGS. 26A and 26B, the fitting 2242 may also comprise a chamber connector 2610 with a fitting slit seal 2602. When the device is assembles, the chamber connector 2610 may be located within the front cap 2220 of the device 2200, but the particular location may vary with the particular embodiment. The fitting slit seal 2602 may comprise a distal ring 2612 with an inner profile configured to engage a groove 2614 on the chamber connector 2610 of the fitting 2242. The outer profile of the seal 2602 and/or the distal ring 2612 may be configured to seal against the inner surface main conduit lumen 2340. The fitting slit seal 2602 may also comprise a slit that provides a deformable passageway through the seal 2602. Thus, in some embodiments, the fitting slit seal 2602 may be configured to both form an airtight seal between the chamber connector 2610 and the conduit lumen 2340 of the suction chamber 2210 and also to control fluid communication through the fitting assembly 2600. FIG. 26B illustrates a side cross sectional view of fitting 2610 coupled to the fitting slit seal 2612 at the fitting's proximal end.

Referring back to FIG. 26A, fitting assembly 2600 may also comprise an interlocking structure that comprises at least one resilient tab 2616 that is disposed on and project outwardly from a base member 2618 coupled or integrally formed with the fitting 2242. When the fitting assembly 2600 is coupled to the suction chamber 2210, the tabs 2616 are configured to engage complementary recesses (2350 in FIGS. 25A and 25B) on the conduit 2330 of the suction chamber 2210. An interlocking mechanism may resist or prevents inadvertent decoupling of the fitting 2242 from the suction chamber 2210. The fitting housing 2240 may further comprise one or more release structures or buttons 2622 that are coupled to or interface with the levers 2624 of the projecting tabs 2618. Depressing the buttons 2622 will release the interlocking mechanism by displacing the tabs 2616 from the notches 2350 on the suction chamber 2210 and permit decoupling of the fitting 2242 and fitting housing 2240 from the front cap 2220 and the suction chamber conduit 2330. The release buttons 2622 may comprise one or more textured gripping surfaces 2626 that may facilitate manual connection or disconnection of the fitting 2242.

Figure 27A:
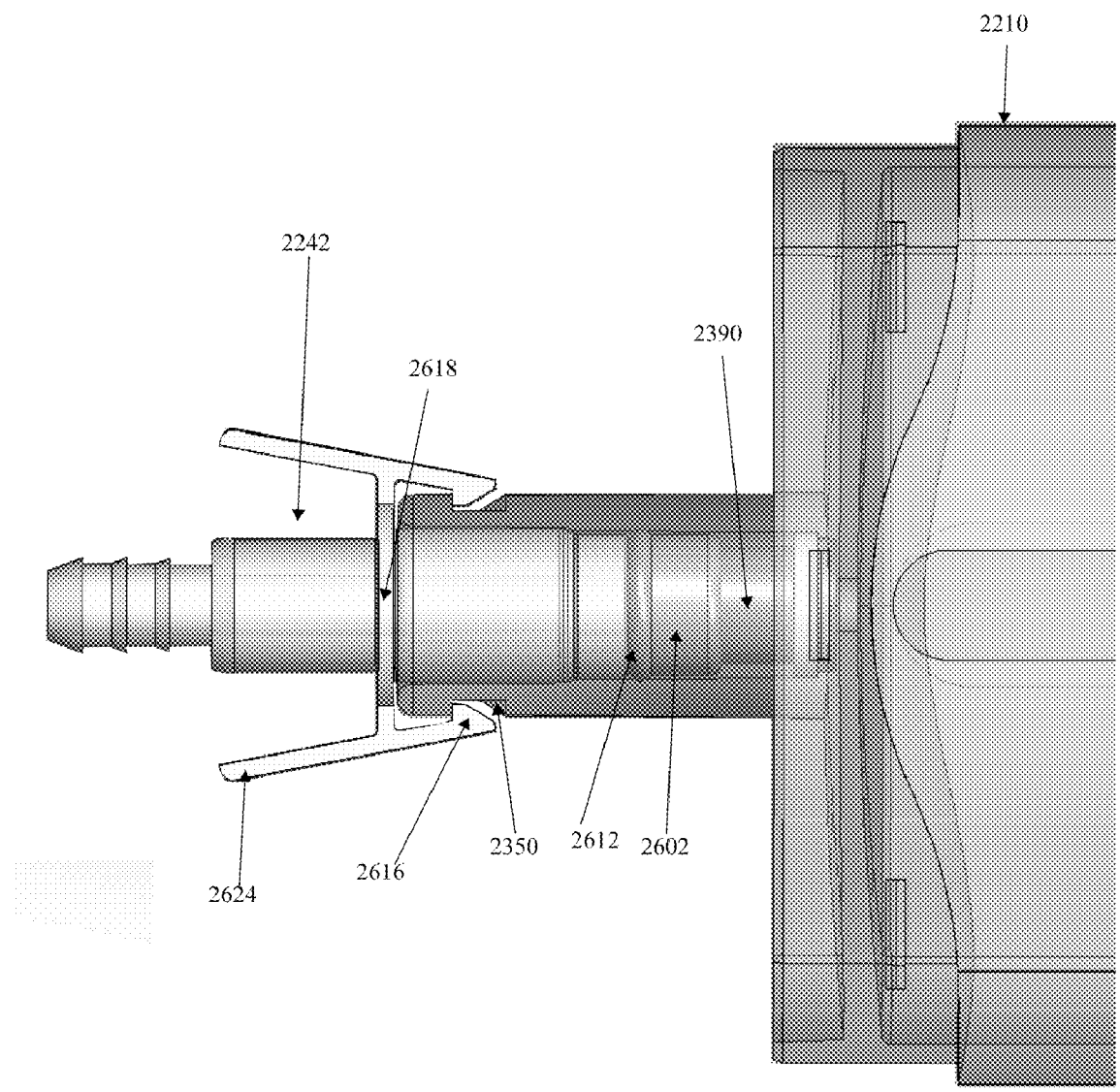
FIG. 27A is a schematic cut-away view of one embodiment of a connecting mechanism between a fitting and a suction chamber connector.
Figure 27B:
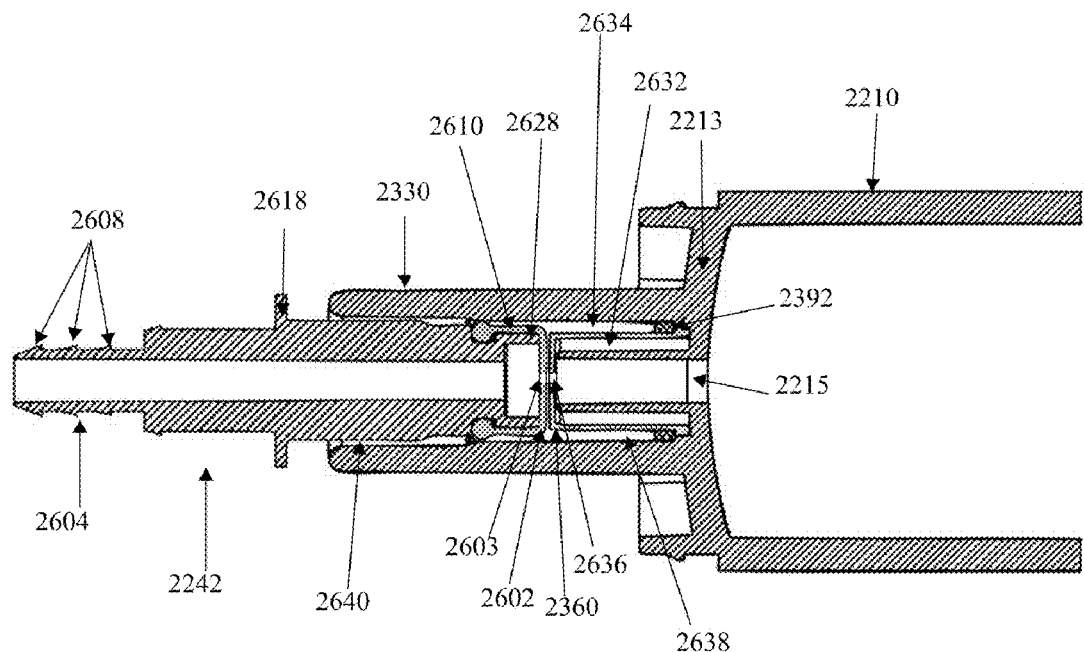
FIGS. 27B and 27C are cross-sectional views of the connecting mechanism from FIG. 27A.
Figure 27C:
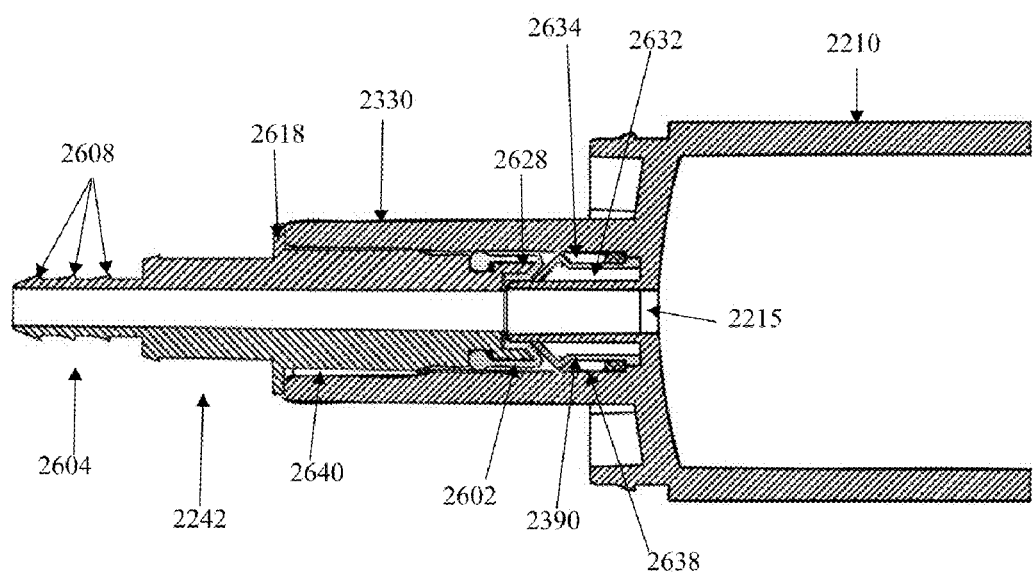

FIG. 27A is a schematic superior cut-away view of the suction chamber 2210 and the fitting 2242 of the fitting assembly 2600 when the fitting 2242 is fully inserted into the conduit 2330. As illustrated, the tabs 2616 projecting from the base member 2618 of the fitting 2242 form an interfit with the notches 2350 on the surface of the suction chamber conduit 2330. FIGS. 27B and 27C are side cross sectional views of a portion of the suction chamber 2210 and the fitting 2242, before and after the fitting 2242 has been fully seated into the conduit 2330. FIGS. 27B and 27C further illustrate the connecting mechanism between chamber slit seal 2390 on the inner conduit 2380 and fitting slit seal 2602 of the fitting 2242. In FIG. 27B, when fitting 2242 is inserted into the conduit 2330, the fitting slit seal 2602 initially contacts chamber slit seal 2390, which is mounted on a seal base 2392. As illustrated in FIG. 27C, further insertion causes the edge 2628 of the chamber connector 2610 to exert a force along the perimeter 2660 of the chamber slit seal 2390. An inner gap 2632 and/or an outer gap 2634 about the chamber slit seal 2390 provide space for the chamber slit seal 2390 to deform or compress away from the edge 2628 of the chamber connector 2610. This results in the enlargement of the opening or slit 2636 of the chamber slit seal 2390 as it is pushed proximally away from the inner conduit opening 2384. In some examples, the inner and outer gaps 2632 2634 may also reduce the frictional resistance of the chamber slit seal 2390 against the inner conduit 2380 or the surface of the conduit lumen 2340, respectively. As the fitting 2242 is further inserted into the conduit lumen 2340, the exposed inner conduit 2380 penetrates through the slit 2603 of the fitting slit seal 2602, thereby opening fluid communication from the suction chamber 2210, through the distal opening 2215 of the suction chamber 2210, through the inner conduit 2380 and through the fitting 2242. In the embodiment depicted in FIGS. 27A to 27C, the tabs 2616 and the notches 2350 of the locking mechanism may be used to provide rotational alignment of the between the fitting slit seal 2602 and the chamber slit seal 2390, if needed. This may be useful where the slits of the seals 2602 and 2390 are single linear slits. In other configurations where the slits are multiple radial slits, rotational alignment may or may not affect the patency of the fluid communication.

When fitting 2242 is decoupled from the suction chamber conduit 2330, of the withdrawal of the inner conduit 2380 from the fitting slit seal 2602 results in closure of the fluid passageways to the sealed wound and may limit air entry into the wound during decoupling. As the fitting 2242 is further separated, the edge 2628 of the chamber connector 2610 is withdrawn and the chamber slit seal 2380 is able to elastically revert back to a closed position to seal the suction chamber 2210. In some embodiments, chamber slit seal 2380 is able to elastically revert back to a closed position with the aid of a coaxially mounted coil spring. Although both seals 2602 and 2390 are closed, the outer surface of the fitting slit seal 2602 continues to form a seal with the conduit lumen 2340 until further separation occurs. As may be seen in FIGS. 2527B and 27C, the conduit lumen 2340 of suction chamber 2210 has a non-uniform diameter along it longitudinal length, and may comprise a proximal segment 2638 having a reduced diameter relative to the distal segment 2640. The transition in diameter between the proximal and distal segments 2638 and 2640 may be gradual or stepped. The conduit lumen 2340, for example, comprises at least one step transition region 2642 between the segments 2638 and 2640. In some examples, step transition region may provide different tactile feedback compared to gradual transitions.

The slit seal may be fluid impervious and may be fabricated from any of suitable resilient materials, such as, but not limited to, synthetic elastomer, silicone rubber, or natural rubber. The seal material may be compatible with wound exudates that may be collected by the suction chamber during a reduced pressure treatment. The seal material may be sterilized by treatment of radiation, steam, ethylene oxide or other suitable techniques known to those skilled in the art.

Turning to FIGS. 28A and 28B now, the spring assembly 2270, which is mounted at the proximal end of the suction chamber and covered by the chamber rear cap, comprises a spring carrier 2820 and a U-shaped spring retainer 2810 containing two bushings 2830 mounted on the two vertical rails 2812 of the spring retainer 2810. Two substantially constant force springs (not shown in this figure) may each comprise a coiled body coupled to and wrapped around bushing 2830 and a free end distally extended and attached to the piston assembly. The springs may or may not be constant force springs. The spring attachment mechanism will be discussed in greater detail below. The spring carrier 2820 comprises a central opening 2824 and two side openings 2826. The central opening 2824 is configured to permit passage of the priming tool to access and displace the piston assembly. The side openings 2826 are configured to house the bushings 2830 and the springs when the spring retainer 2810 is coupled to the spring carrier 2820. As shown in this figure, multiple ridges 2821 may be located adjacent the side openings 2826 to limit the movement of the bushings 2830 and springs coiled around bushings 2830, thereby reducing deflections or deformations of the springs during operation of the suction apparatus. The spring carrier 2820 may also comprise resilient tabs 2822 that may slidably engage one or more grooves on the priming tool shaft, which may reduce angular deviations of the priming tool with respect to the longitudinal movement axis of the seal. The spring carrier 2820 may also comprises two interlocking structures 2823 configured to releasably lock the priming tool in place after the suction apparatus is primed. The interlocking mechanism will be described in detail later. Fixation structures 2828 may be provided to form a snapfit or other type of interfit with complementary structures on the suction chamber.

FIGS. 29A and 29B are component views of the piston assembly 2260 that comprises a piston seal 2910 and a piston 2920. The piston assembly 2260 may be configured to traverse between the distal end and the proximal end of the suction chamber while maintaining a substantially airtight seal. As mentioned previously, the piston assembly 2260 provides an airtight separation the suction chamber between a collection chamber and a working chamber. In the depicted embodiment, the piston seal 2910 has a non-circular, elliptical cross-sectional shape with respect to its movement axis in the suction chamber, but in other embodiments, other shapes as described herein may be used. The piston seal 2910 may comprise a side wall 2911 and a distal end wall 2912. The side wall 2911 of the piston seal 2910 further comprises a distal perimeter ridge 2914 and a proximal perimeter ridge 2916, the dimensions of which may be larger than that of the side wall 2911 of piston seal 2910. The ridges 2914 and 2916 may be configured to be in a sliding contact with the interior surface of the suction chamber. They may provide a sealed contact while limiting sliding friction. The exterior surfaces of the piston seal and/or the interior surfaces of the suction chamber may comprise a friction-reducing lubricant or a lubricious coating material.

The piston seal 2910 may be detachably coupled to the piston 2920 or in some embodiments, the piston seal 2910 and the piston 2910 may be integrally formed. In the depicted embodiment, the piston 2920 may comprise an elliptical frame with a side wall 2924. The distal portion of side wall 2920 may comprise a recess 2926 and a raised edge or flange 2928 configured form a complementary interfit with the piston seal 2910. The proximal perimeter edge 2930 of side wall 2922 may have a complementary shape to the distal edge 2829 of the spring carrier 2820. In the depicted embodiment, both the proximal edge 2930 of the piston side wall 2922 and the distal perimeter edge 2829 of the spring carrier have a curved, non-planar configuration. As mentioned previously, the seal and/or seal mount (e.g. piston 2920) may have a variable longitudinal length along its perimeter. In some instances, an increased longitudinal dimension may provide additional stability to the seal along a dimension of the seal. In some examples, the side length along a section of the perimeter of the piston 2920 may be related to the transverse dimension intersecting a) that side length of the perimeter and b) the central movement axis of the seal and/or piston. In the example in FIG. 29A, the lateral longitudinal surface of the piston 2920 may have a longitudinal length 2932, based upon the increased width 2934 of the piston 2920 relative to the height 2936 of the suction chamber 2210 (corresponding to the increased width and reduced height of the suction chamber 2210). In comparison, the superior longitudinal surface of the piston 2920 may have a longitudinal length 2938 that is smaller than the longitudinal length 2932 of the lateral longitudinal surface from the reduced height 2936 of the piston 2920.

Figure 29C:
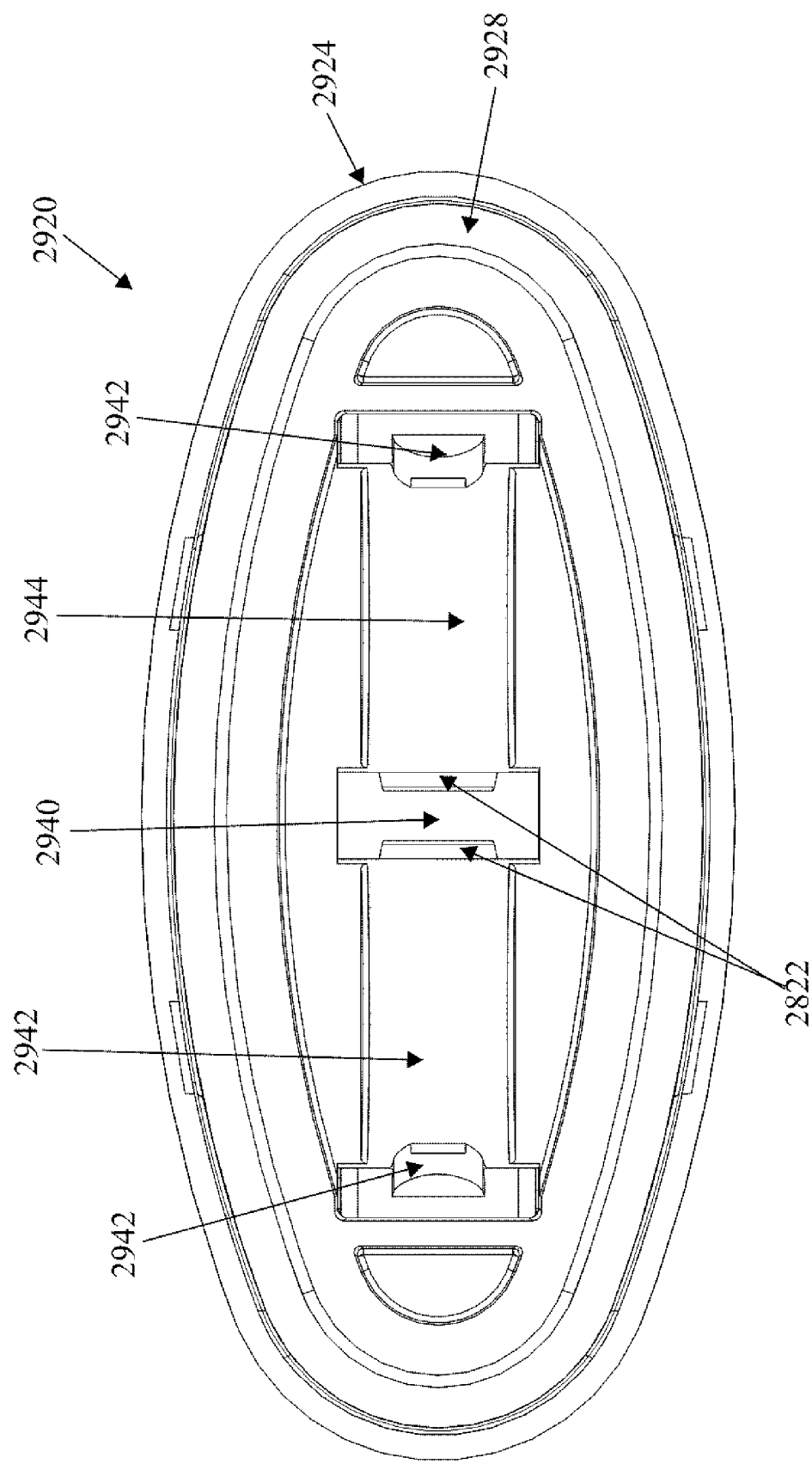
FIG. 29C is a front elevational view of the piston assembly.
Figure 30:
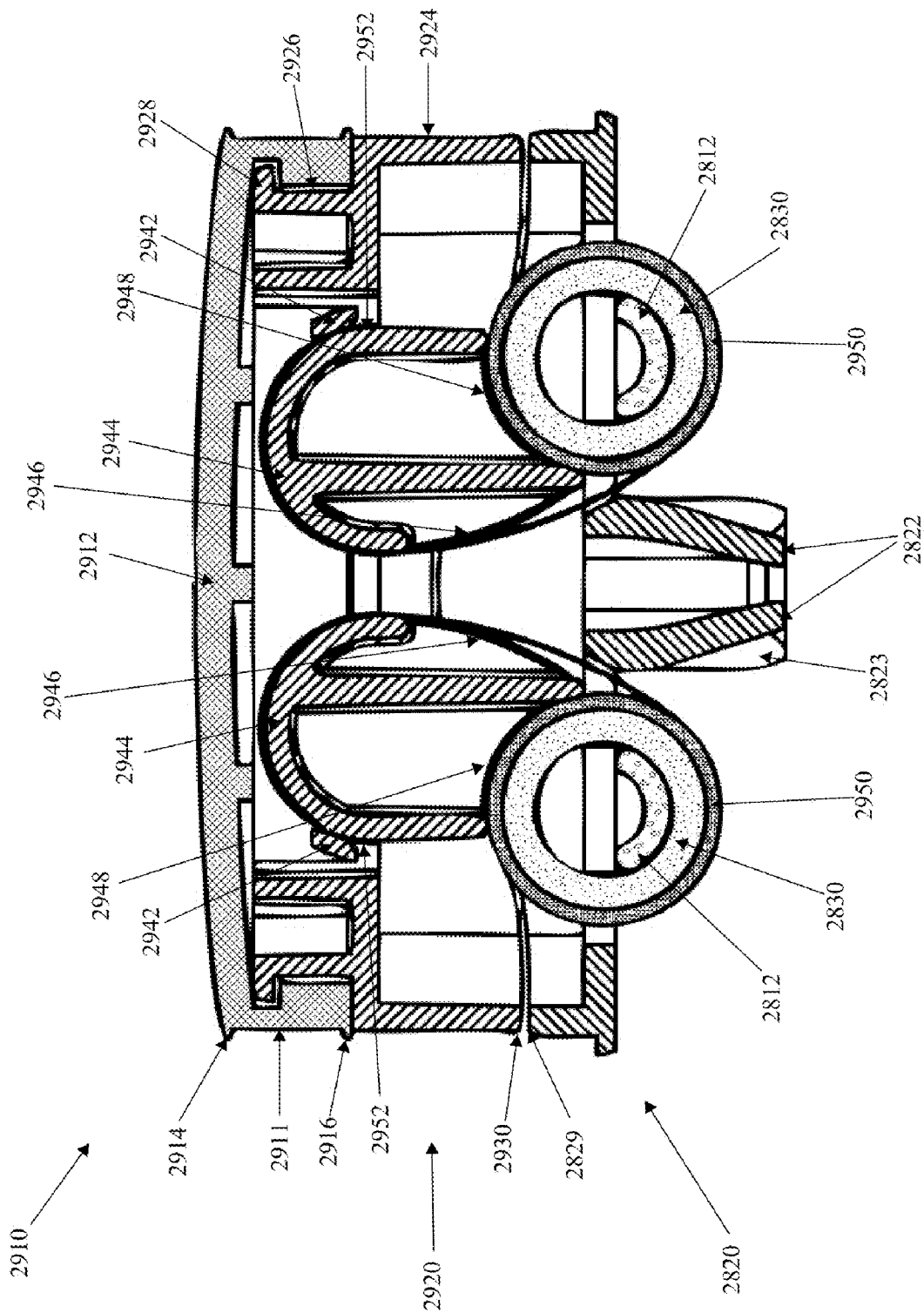
FIG. 30 is a cross sectional view of one embodiment of a piston assembly coupled to a spring assembly.

Referring to FIGS. 29A, 29B and 30, the piston 2920 may also comprise a central opening 2940 which may be aligned with the central opening 2824 of spring carrier 2820. The piston central opening 2940 may be configured to provide passage of the distal ends of the constant force springs. FIG. 29C provides a frontal elevational view of the piston 2920. The distal regions 2952 of the constant force springs 2950 (depicted only in FIG. 30) may extend through the central opening 2940 and are coupled to a pair of spring retaining structures 2930 disposed on the front surface of piston 2920. In this particular embodiment, the retaining structures 2930 are configured to be inserted into apertures provided on the springs and may or may not maintain their coupling using residual spring force that may be present in the springs in the retracted configuration. The retaining structure and the springs may have any of a variety of other coupling configurations, however (e.g. the retaining structures may comprise posts which block displacement of T-shaped spring ends). Between the central opening 2940 and the retaining structures 2942 are curved support surfaces 2944 which are configured to push against the springs. In some examples, the length of the curved support surfaces 2944 between the central opening 2940 and the retaining structures 2930 may be at least one or one and a half times the width of the springs, while in other examples may be two or three times or four times the width of the springs. In some examples, the curved support surfaces 2944 provide a substantial surface area to distribute the pushing forces and may reduce the risk of damage to the springs. Referring back to FIG. 29A, the piston 2920 may further comprise convex supports 2946 adjacent to the central opening 2940, which may also support the springs as the springs converge into the central opening 2940. The convex supports 2946 may have a curved length of at least about the width of the springs, but in other examples may be at least two or three times the width of the springs. Referring to FIGS. 29A and 30, the convex supports 2926 may also comprise a concave region 2948, which may accommodate the coils of the spring and the spring carriers 2830 when the piston assembly 2260 is in a retracted configuration. Although the piston assembly 2260 and the spring assembly 2270 depicted in FIGS. 28A to 29B utilized two springs, in other examples, one spring, three springs, four springs, or five or more springs may be used. The number of springs, the type of springs, and the width and length of the springs may be varied, and in other examples, non-spring bias members may be used (e.g. sealed pneumatic shocks).

Figure 31B:
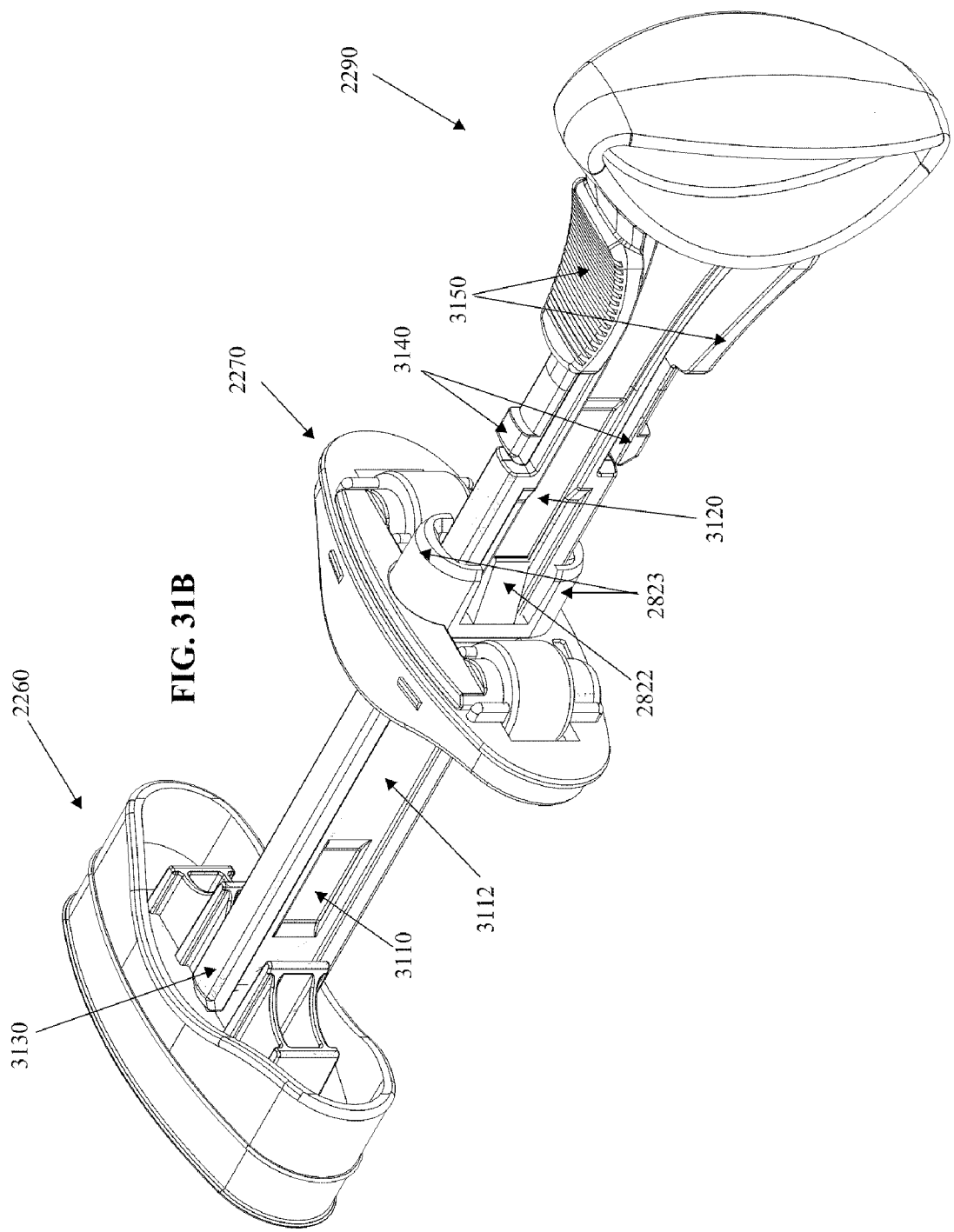
Figure 31C:
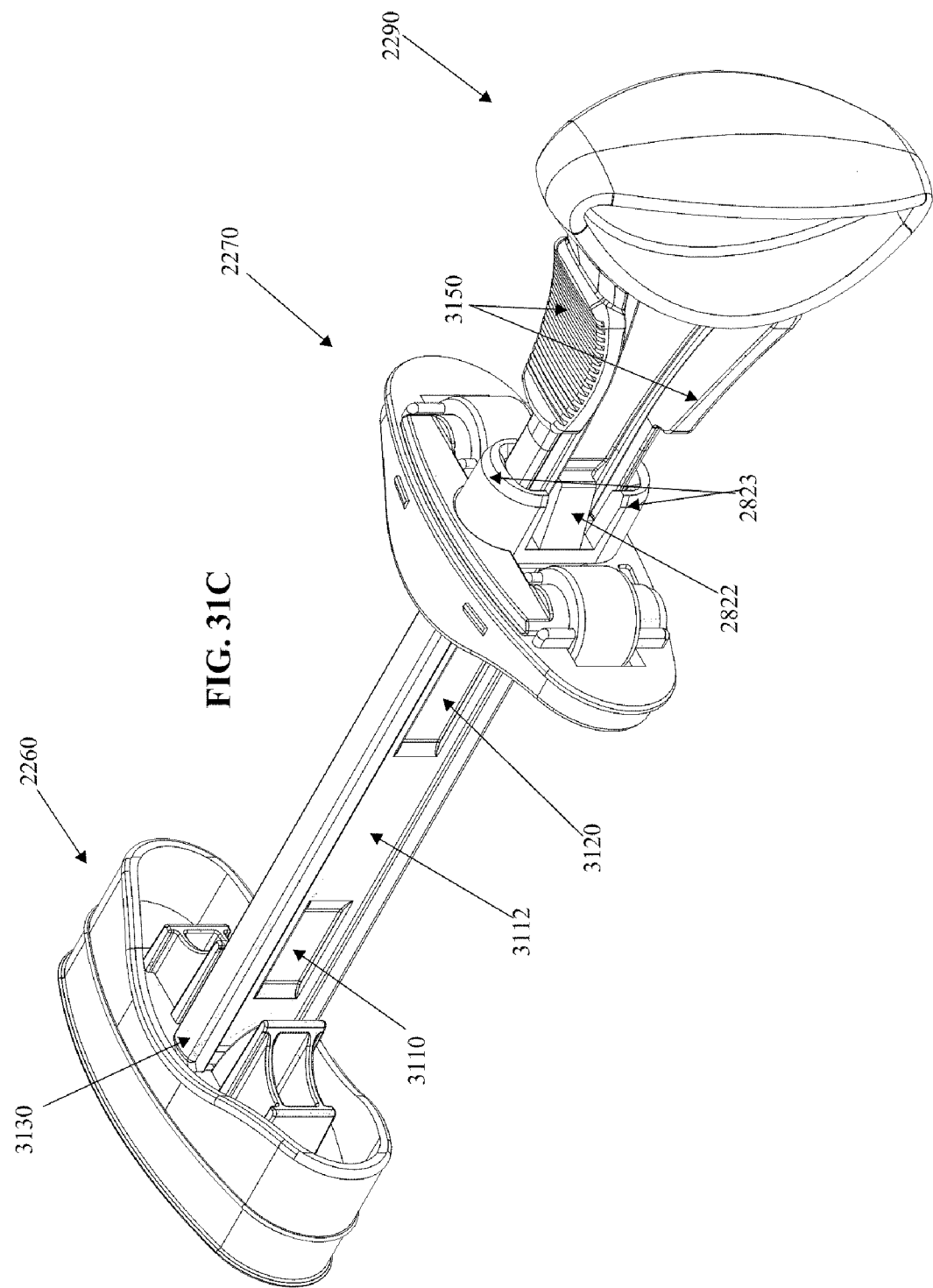

FIGS. 31A to 31C schematically illustrate one example of a priming procedure of the suction apparatus 2200 with a priming tool 2290 from FIGS. 23A and 23B, where the springs have not been shown to better illustrate the interactions between the piston assembly 2260, spring assembly 2270 and the priming tool 2290. The priming tool 2290 comprises a tool shaft 3100 with a distal recess 3110 and a proximal recess 3120 on each side of the shaft 3100. Located between the recesses 3110 and 3120 is a non-recessed portion of the shaft 3100. The distal end 3130 of the priming tool 2290 is has a cross sectional shape and size that is able to pass through the central opening 2824 of the spring assembly 2270 to contact the piston 2920 of the piston assembly 2260. During the priming procedure, the priming tool 2290 may be pushed against the piston 2920 but is not configured to couple or attach to the piston 2920. In other embodiments, however, the distal end 3130 of the priming tool 2290 and the piston 2920 may be configured to form a complementary interlocking fit or interference fit. Before priming, the springs will pull and maintain the piston assembly 2260 into a proximal or retracted position against the spring assembly 2270. As the priming tool 2290 is inserted into the suction apparatus, the resilient tabs 2822 on the spring assembly 2270 will slidably engage the distal recess 3110 on the tool shaft 3100. As the priming tool 2290 is further inserted, the user may receive tactile feedback of increased resistance as the tabs 2822 are resiliently displaced out of the distal recesses 3110. Further insertion may provide additional tactile feedback from increased frictional resistance by the tabs 2822 against the non-recessed portion 3112 of the shaft 3100. As the priming tool 2290 is further inserted, the piston assembly 2260 is separated from the spring assembly 2270 and the constant force springs or bias members attaching the assemblies 2260 and 2270 will elongate and generate potential energy. As piston assembly 2260 is further displaced distally, the tabs 2822 will then engage the proximal recess 3120 on the prime tool shaft 3100. The position and length of the of the non-recessed portion 3112 and the recesses 3110 and 3120 of the shaft 3100 may be configured to provide the user with tactile feedback indication, or may be provided to resist ejection of the priming tool 2290 out of the suction apparatus. For example, if the wound or fluid communication to the wound is incompletely sealed, or if there is an excessive volume of air or exudates the wound, upon activation of the suction apparatus, the piston assembly 2260 may retract suddenly. The non-recessed portion 3112 of the priming tool 2290 may provide at least partial retention of the tool 2290 so that the user can reprime the suction apparatus. The recesses 3110 and 3120 may be configured with ramped proximal and distal surfaces movement of the tabs 2822 in and out of the recesses 3110 and 3120.

Upon full priming of the suction apparatus, latches 3140 located on the prime tool shaft 3110 may engage the interlocking structures 2823 on the spring assembly 2270 to locks the priming tool 2290 into place, as depicted in FIG. 31C. The priming tool 2290 may be left in the locked configuration in the suction apparatus, and may even be stored and/or distributed in a primed poison. The locking mechanism also permits the suction apparatus to be primed without requiring that the suction apparatus be already coupled to the sealant layer. Thus, the user need not be concerned about uncoupling the suction apparatus or unsealing the sealant layer during the priming procedure, and may handle or orient the suction apparatus in any manner, e.g. abutting the connector surface of the suction apparatus against a table or wall to provide leverage when pushing the priming tool.

To activate the primed suction apparatus, the user may depress the release buttons 3150 located at the proximal end of the prime tool 2290. Pressing the release buttons 3150 disengage the latches disengages latches 3140 from the interlocking structures 2823, thereby permitting the removal of the priming tool 2290 out of the suction chamber. The release buttons 3150 may also comprise one or more textured gripping structures or materials to facilitate latch release. Although the embodiment depicts in FIGS. 31A to 31C comprises a priming tool 2290 with two latches 3140 and two release buttons 3150, in other embodiments, a different number latches and/or buttons may be provided, or a different configuration of a locking mechanism may be provided (e.g. a locking pin that may be inserted and removed by the user).

As described previously, once the priming tool 2290 is proximally withdrawn, the piston assembly will be retracted by the charged constant force springs. Such movement will expand the combined volume of the space below the piston assembly and the sealed wound enclosure, and reduce the pressure level therein. Where there has been an inadvertent leak in the system or excessive air or exudates in the wound, the priming tool 2290 may be used to reprime the device. In these embodiments, the method for using the suction apparatus may further comprise resealing the wound and/or reseating one or more connectors of the reduced pressure therapy device, and repositioning the slidable seal or piston assembly to the extended or primed position and reactivating the device.

In some embodiments, the method of treating an area of damaged tissue may comprise affixing a sealant layer around an area of tissue to be treated; creating a sealed enclosure around the area of the tissue with the sealant layer, inserting a collection chamber into a housing chamber and priming the collection chamber; creating a fluid communication between the collection chamber and the sealed wound enclosure; activating the collection chamber to create a reduced pressure level within the sealed wound enclosure; if the collection chamber is filled up with wound exudates, terminating the fluid communication between the collection chamber and the wound seal and releasing the collection chamber from the wound site; withdrawing the collection chamber from the housing chamber and replacing it with a new collection chamber; and repeating the steps as appropriate to continue a reduced pressure treatment.

Although the embodiments herein have been described in relation to certain examples, various additional embodiments and alterations to the described examples are contemplated within the scope of the invention. Thus, no part of the foregoing description should be interpreted to limit the scope of the invention as set forth in the following claims. For all of the embodiments described above, the steps of the methods need not be performed sequentially. Accordingly, it is not intended that the invention be limited, except as by the appended claims.

What is claimed:

1. A reduced pressure treatment system, comprising:
a flexible polyurethane cover comprising a first side, a second side, and an opening therethrough;
a hydrocolloid adhesive located on the first side of the cover;
a flexible port attached to the second side of the cover, the port comprising a tubing connector and lumen in communication with the opening of the cover;
a tube attached to the port at the tubing connector;

an elongate activation key;

a chamber adapted to create a reduced pressure, said chamber having a distal end wall with an inlet opening, a proximal opening, and a rigid non-circular side wall between the seal end wall and the proximal opening; and a seal located within the chamber, the seal comprising a perimeter that forms a vacuum-resistant seal with the rigid non-circular side wall of the chamber and is configured to slide along a longitudinal axis of the chamber while creating said reduced pressure and to removably receive the distal end of an elongate activation key;

a proximal end cap attached about the proximal opening of the vacuum chamber, the proximal end cap comprising an activation key opening, and a spring attachment site; and at least one coiled ribbon spring located in the chamber, the spring comprising a distal end attached to the seal and a proximal end attached to the spring attachment site of the proximal end cap.

2. A reduced pressure treatment system, comprising:

a flexible cover comprising a first side, a second side, and an opening there through;

an adhesive located on the first side of the cover;

a port attached to the second side of the cover, the port comprising a lumen in communication with the opening of the cover;

a tube attached to the port;

a chamber comprising an inlet opening and a rigid side wall; and a seal mechanism located within the chamber, the seal mechanism comprising a perimeter that forms a vacuum-resistant seal with the rigid side wall of the chamber and is configured to slide along a longitudinal axis of the chamber while creating reduced pressure and to removably receive an activation element; and a spring mechanism located in the chamber and attached to the seal mechanism.

3. The system of claim 1, wherein the cover comprises a permeable polyurethane cover.

4. The system of claim 1, wherein the adhesive comprises a hydrocolloid.

5. The system of claim 1, wherein the port comprises an elastomeric material.

6. The system of claim 4, wherein the port comprises a flat, elastomeric base.

7. The system of claim 1, wherein the port is a flexible port.

8. The system of claim 1, wherein the spring mechanism comprises a ribbon spring.

9. The system of claim 1, wherein the spring mechanism comprises a substantially constant force spring.

10. The system of claim 1, wherein the spring mechanism comprises two ribbon springs.

11. The system of claim 1, wherein the chamber further comprises a distal end wall and a proximal opening.

12. The system of claim 10, wherein the inlet opening of the chamber is located on the distal end wall.

13. The system of claim 10, wherein the rigid side wall of the chamber comprises a non-circular cross-sectional shape.

14. The system of claim 12, wherein the non-circular cross-sectional shape is an oval shape.

15. The system of claim 10, further comprising an end cap attached to the proximal opening of the chamber.

16. The system of claim 14, wherein the end cap comprises an activation opening.

17. The system of claim 15, wherein spring mechanism is attached to the end cap.

18. The system of claim 1, wherein the seal mechanism comprises a rigid structure and a soft sealing structure attached to the rigid structure.

19. The system of claim 17, wherein spring mechanism is attached to the rigid structure.

20. The system of claim 9, wherein the each of the two ribbon springs comprises an inner surface, an outer surface and edges therebetween.

21. The system of claim 19, wherein a flat surface of each ribbon spring faces a flat surface of the other ribbon spring.

22. The system of claim 20, each ribbon spring intersects a line located across a maximum dimension of the seal mechanism.

23. The system of claim 20, wherein the ribbon springs have opposite coil orientations.

24. The system of claim 1, further comprising a lubricant on the rigid side wall of the chamber.

25. The system of claim 1, wherein the seal mechanism is further configured to removably receive an activation element.

26. The system of claim 24, further comprising an activation element configured to be removably inserted into the chamber to displace the seal mechanism.

27. The system of claim 25, wherein the activation element is configured to releasably lock the position of the seal mechanism.

28. A system for treating a wound of a patient, comprising:

a sealable wound covering comprising a flexible sealant layer and an integrally formed attachment port having a lumen that passes through the port; and a non-electrically powered, reduced pressure generating assembly capable of being activated to apply said reduced pressure, comprising:

a suction chamber with a longitudinal axis and an initial non-circular cross-sectional shape transverse to the longitudinal axis and an internal volume of 250 cc or less, said chamber capable of being primed prior to activation, and capable of maintaining its initial non-circular cross-sectional shape after activation;

a piston assembly configured to slide inside the suction chamber along the longitudinal axis and having a non-circular cross-sectional shape transverse to the longitudinal axis;

at least one substantially constant force spring coil coupled to the piston assembly and configured to reduce pressure in the suction chamber by at least 50 mmHg; and a connector tube configured to releasably attach the chamber to the sealable wound covering at the attachment port, to permit fluid communication between the wound and the reduced pressure generating apparatus through the sealable wound covering.

29. The system of claim 28, wherein the suction chamber is adapted to collect exudate fluids from the wound.

30. The system of claim 28, wherein said piston assembly divides said internal volume of said suction chamber into a variable-volume fluid collection chamber and a variable-volume working chamber, said reduced pressure generating assembly having a removable elongate priming tool for priming the assembly by reducing the volume of the fluid collection chamber and expanding the volume of the working chamber prior to activation, and an activating device to cause the assembly to apply reduced pressure to the wound by expanding the volume of the fluid collection chamber through discharging potential energy stored in said at least one spring coil.

31. The system of claim 28, wherein the system is silent during application of the reduced pressure to the wound.

32. The system of claim 28, wherein said system further comprises a pressure gauge for indicating the level of reduced pressure being applied by the system after activation.

33. The system of claim 28, wherein said suction chamber comprises a viewing window to visually assess, after activation, at least one of the reduced pressure levels being applied by said assembly and the exudate fluids being collected in said fluid collection chamber.

34. The system of claim 28, wherein said assembly comprises an indicator to indicate the status of assembly's capacity to continue to generate said reduced pressure.

35. The assembly of claim 28, wherein said suction chamber maintains its initial non-circular cross-sectional shape over a range of collection volumes of exudate.

* * * * *